United States Patent
Chin et al.

(10) Patent No.: US 11,690,380 B2
(45) Date of Patent: *Jul. 4, 2023

(54) ANTIMICROBIAL GUANIDINIUM AND THIOURONIUM FUNCTIONALIZED POLYMERS

(71) Applicants: International Business Machines Corporation, Armonk, NY (US); AGENCY FOR SCIENCE, TECHNOLOGY AND RESEARCH, Singapore (SG)

(72) Inventors: Willy Chin, Singapore (SG); James L. Hedrick, Pleasanton, CA (US); Nor Lizawati Ibrahim, Singapore (SG); Ashlynn L. Z. Lee, Singapore (SG); Robert J. Ono, San Jose, CA (US); Qingxing Xu, Singapore (SG); Yi Yan Yang, Singapore (SG)

(73) Assignees: Coral Bay II, LLC, New York, NY (US); Agency For Science, Technology And Research, Singapore (SG)

( * ) Notice: Subject to any disclaimer, the term of this patent is extended or adjusted under 35 U.S.C. 154(b) by 560 days.

This patent is subject to a terminal disclaimer.

(21) Appl. No.: 16/686,111

(22) Filed: Nov. 16, 2019

(65) Prior Publication Data

US 2020/0085059 A1 Mar. 19, 2020

Related U.S. Application Data

(60) Continuation of application No. 15/645,838, filed on Jul. 10, 2017, now Pat. No. 10,779,539, which is a division of application No. 14/715,690, filed on May 19, 2015, now Pat. No. 9,854,806.

(51) Int. Cl.
| | |
|---|---|
| A01N 47/44 | (2006.01) |
| C08G 64/42 | (2006.01) |
| C08G 18/38 | (2006.01) |
| C08G 64/02 | (2006.01) |
| C08G 18/48 | (2006.01) |
| C08G 18/66 | (2006.01) |
| C08G 18/73 | (2006.01) |
| C08G 18/75 | (2006.01) |
| C08G 64/30 | (2006.01) |

(52) U.S. Cl.
CPC ......... *A01N 47/44* (2013.01); *C08G 18/3819* (2013.01); *C08G 18/3831* (2013.01); *C08G 18/4833* (2013.01); *C08G 18/6681* (2013.01); *C08G 18/73* (2013.01); *C08G 18/755* (2013.01); *C08G 64/0241* (2013.01); *C08G 64/30* (2013.01); *C08G 64/42* (2013.01)

(58) Field of Classification Search
None
See application file for complete search history.

(56) References Cited

U.S. PATENT DOCUMENTS

| | | | |
|---|---|---|---|
| 6,464,971 B1 | 10/2002 | Matthews et al. | |
| 7,169,814 B2 | 1/2007 | Rothbard et al. | |
| 7,862,807 B2 | 5/2011 | Goodman et al. | |
| 7,939,621 B2 | 5/2011 | Cooley et al. | |
| 8,586,705 B2 | 11/2013 | Krippner et al. | |
| 2013/0274173 A1 | 10/2013 | Cheng et al. | |
| 2016/0257782 A1* | 9/2016 | Coady | C08G 64/025 |

FOREIGN PATENT DOCUMENTS

EP 2338923 A1 6/2011

OTHER PUBLICATIONS

Timin et al. (Colloid Polym Sci, 293, 1667-1674, 2015) Synthesis and application of silica hybrids grafted with new guanidine-containing polymers as highly effective adsorbents for bilirubin removal.*
Ong et al. (Journal of Controlled Release 152 (2011) 120-126) Rational design of biodegradable cationic polycarbonates for gene delivery.*
USPTO, Final Office action, U.S. Appl. No. 15/645,838, dated Mar. 20, 2020.
USPTO, Non-final Office action, U.S. Appl. No. 16/686,109, dated Apr. 6, 2020.
Cooley, et al., "Oligocarbonate Molecular Transporters: Oligomerization-Based Syntheses and Cell-Penetrating Studies", J. Am. Chem. Soc. 2009, 131, 16401-16403; Published on Web Oct. 27, 2009.
Edward, et al., "Organocatalytic Synthesis of Quinine-Functionalized Poly(carbonate)s", Biomacromolecules 2012, 13, 2483-2489; Published: Jul. 31, 2012.
Gabriel, et al., "Synthetic Mimic of Antimicrobial Peptide with Nonmembrane-Disrupting Antibacterial Properties", Biomacromolecules 2008, 9, 2980-2983; Published on Web Oct. 14, 2008.
Geihe, et al., "orgDesigned guanidinium-rich amphipathic oligocarbonate molecular transporters complex, deliverand release siRNA in cells", Proceedings of the National Academy of Sciences of the United States of America, vol. 109, No. 33 (Aug. 14, 2012), pp. 13171-13176.
Locock, et al., "Guanylated Polymethacrylates: A Class of Potent Antimicrobial Polymers with Low Hemolytic Activity", Biomacromolecules 2013, 14, 4021-4031; Published: Oct. 7, 2013.

(Continued)

*Primary Examiner* — Tigabu Kassa

(57) ABSTRACT

Antimicrobial cationic polycarbonates and polyurethanes have been prepared comprising one or more pendent guanidinium and/or isothiouronium groups. Additionally, antimicrobial particles were prepared having a silica core linked to surface groups comprising a guanidinium and/or isothiouronium group. The cationic polymers and cationic particles can be potent antimicrobial agents against Gram-negative microbes, Gram-positive microbes, and/or fungi.

23 Claims, 18 Drawing Sheets

(56) References Cited

OTHER PUBLICATIONS

Pratt, et al., "Exploration, Optimization, and Application of Supramolecular Thiourea-Amine Catalysts for the Synthesis of Lactide (Co)polymers", Macromolecules 2006, 39, 7863-7871; Published on Web Oct. 18, 2006.

Pratt, et al., "Tagging alcohols with cyclic carbonate: a versatile equivalent of (meth)acrylate for ring-opening polymerization", Chem. Commun., 2008, 114-116.

USPTO, Non-final Office action, U.S. Appl. No. 14/715,690, dated Aug. 12, 2016.

USPTO, Non-final Office action, U.S. Appl. No. 15/645,838, dated Nov. 1, 2019.

USPTO, Final Office action, U.S. Appl. No. 14/715,690, dated Jan. 9, 2017.

Zhou, et al., "Synthesis and Characterization of Novel Aliphatic Poly(carbonate-ester)s with Functional Pendent Groups", Macromol. Rapid Commun. 2005, 26, 1309-1314.

USPTO, final Office action, U.S. Appl. No. 16/686,109, dated Sep. 4, 2020.

\* cited by examiner

ANTIMICROBIAL GUANIDINIUM AND THIOURONIUM FUNCTIONALIZED POLYMERS

This invention was made under a joint research agreement between International Business Machines Corporation and the Agency For Science, Technology and Research.

BACKGROUND

The present invention relates to antimicrobial guanidinium and thiouronium functionalized polymers, and more specifically to guanidinium and thiouronium functionalized polycarbonates and polyurethanes having broad spectrum antimicrobial properties.

Over the last few decades, the emergence of drug-resistant pathogens, especially Gram-negative bacteria such as *Pseudomonas aeruginosa* (*P. aeruginosa*), has become increasingly prevalent and confounds numerous control efforts, consequently becoming a public health concern. There are no effective and safe antibiotics available for treating such infections. A treatment in clinic is often based on polymixin antibiotics via injection. Polymixins cause severe harmful side-effects (nephrotoxicity and neurotoxicity) when administered by injection. On the other hand, polymixins are not effective against Gram-positive bacteria. Therefore, a need exists to develop novel antimicrobial compounds that exhibit reduced propensity towards resistance development and potency against both Gram-positive and Gram-negative bacteria.

Effective and unconventional antimicrobial agents based on peptides and synthetic polymers have been developed in the last decade that have broad-spectrum antimicrobial activity. However, high manufacturing cost and poor in vivo stability have limited their use. Much effort has been directed towards the development of less costly synthetic polymers.

Several membrane-active peptides and proteins such as the HIV-1 TAT peptide or the amphipathic alpha- and theta-defensins exhibit stronger cell-membrane interaction with arginine compared to lysine. This is attributed in part to the ability of the guanidinium side chain of arginine residues to form stable multi-dentate hydrogen bonds with phosphate head groups on the lipid-based bacterial membrane. Recently, guanidinium-functionalized synthetic polymers were shown to be effective antimicrobial agents having favorable hemolytic selectivity. However, the guanylated polymers have several deficiencies: i) they are non-degradable, which limits in vivo application, ii) they are prepared using a heavy metal (e.g., ruthenium) catalyst, which presents cytotoxic issues typically associated with catalyst residues, and iii) the guanylated polymers are relatively inactive against Gram-negative bacteria (e.g., *E. coli*), leading to a narrow spectrum of bioactivity for potential clinical applications.

A need exists for effective, broad-spectrum, biodegradable guanidinium-and isothiouronium-functionalized antimicrobial polymers of low cytotoxicity.

SUMMARY

Accordingly, an antimicrobial cationic polymer is disclosed, comprising a cationic subunit of formula (A-1):

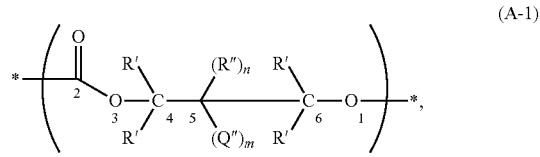

wherein
atoms 1-6 are backbone atoms of the cationic polymer,
m is 1 or 2,
n is 0 or 1, wherein when m is 2, n is 0,
each R' is an independent monovalent radical selected from the group consisting of hydrogen and alkyl groups comprising 1 to 6 carbons,
R" is a monovalent radical selected from the group consisting of hydrogen and alkyl groups comprising 1 to 6 carbons, and
each Q" is an independent group comprising a guanidinium and/or an isothiouronium group.

Also disclosed is a method of killing a microbe, comprising contacting the microbe with an above-described cationic polymer.

Further disclosed is a method of forming an above-described cationic polymer, comprising:
forming an initial polymer by organocatalyzed ring opening polymerization of a cyclic carbonate monomer of formula (M-1):

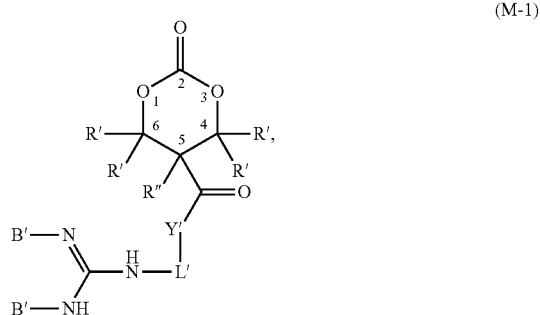

wherein
ring atoms are numbered 1 to 6,
each B' is an independent acid-labile protecting group,
L' is a divalent hydrocarbon radical comprising 2 to 30 carbons,
each R' is an independent monovalent radical selected from the group consisting of hydrogen and alkyl groups comprising 1 to 6 carbons,
R" is a monovalent radical selected from the group consisting of hydrogen and alkyl groups comprising 1 to 6 carbons, and
Y' is *—O—* or *—N(H)—*; and
treating the initial polymer with a protic acid, thereby forming the cationic polymer.

Additionally disclosed is an antimicrobial particle, comprising:
a core comprising silica; and
a plurality of independent surface groups covalently linked to the core, wherein one or more of the surface groups comprises one or more cationic subunits of formula (A-2):

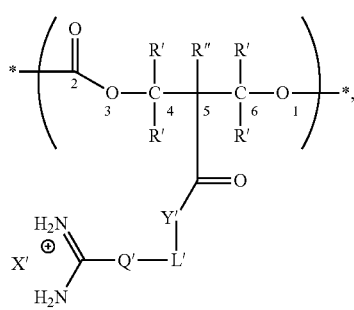

(A-2)

wherein
atoms 1-6 are backbone atoms of the surface groups,
L' is a divalent hydrocarbon radical comprising 2 to 30 carbons,
Q' is *—N(H)—* or *—S—*,
each R' is an independent monovalent radical selected from the group consisting of hydrogen and alkyl groups comprising 1 to 6 carbons,
R" is a monovalent radical selected from the group consisting of hydrogen and alkyl groups comprising 1 to 6 carbons,
X' is a negative-charged counterion, and
Y' is *—O—* or *—N(H)—*.
Further disclosed is a method of killing a microbe, comprising contacting the microbe with an above-described particle.
Also disclosed is an antimicrobial composition comprising the cationic polymer of claim 1 and at least one other chemical component. Examples of antimicrobial compositions include soaps, shampoos, skin lotions, skin creams, cosmetics, mouthwashes, wound care agents, deodorants, surface cleaning agents, and laundry detergents.
Additionally disclosed is an antimicrobial cationic polycarbonate, comprising:
a cationic repeat unit of formula (A-4):

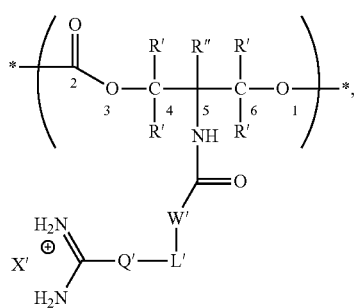

(A-4)

wherein
atoms 1-6 are backbone atoms of the cationic polycarbonate,
L' is a divalent hydrocarbon radical comprising 2 to 30 carbons, Q' is *—N(H)—* or *—S—*,
R' is a monovalent radical selected from the group consisting of hydrogen and alkyl groups comprising 1 to 6 carbons,
R" is a monovalent radical selected from the group consisting of hydrogen and alkyl groups comprising 1 to 6 carbons,
X' is a negative-charged counterion, and
W' is a single bond, *—O—*, or *—N(H)—*.
Further disclosed is an antimicrobial cationic polyurethane, comprising:
a cationic repeat unit according to formula (U-1):

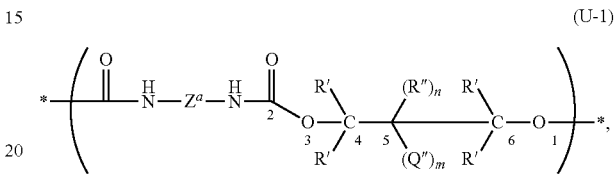

(U-1)

wherein
m is integer having a value of 1 or 2,
n is 0 or 1, wherein when m is 2, n is 0,
each R' is an independent monovalent radical selected from the group consisting of hydrogen and alkyl groups comprising 1 to 6 carbons,
R" is a monovalent radical selected from the group consisting of hydrogen and alkyl groups comprising 1 to 6 carbons,
$Z^a$ is a divalent hydrocarbon radical comprising 2 to 20 carbons, and
each Q" is an independent group comprising a guanidinium and/or isothiouronium group.

The above-described and other features and advantages of the present invention will be appreciated and understood by those skilled in the art from the following detailed description, drawings, and appended claims.

DETAILED DESCRIPTION

Figure 1:
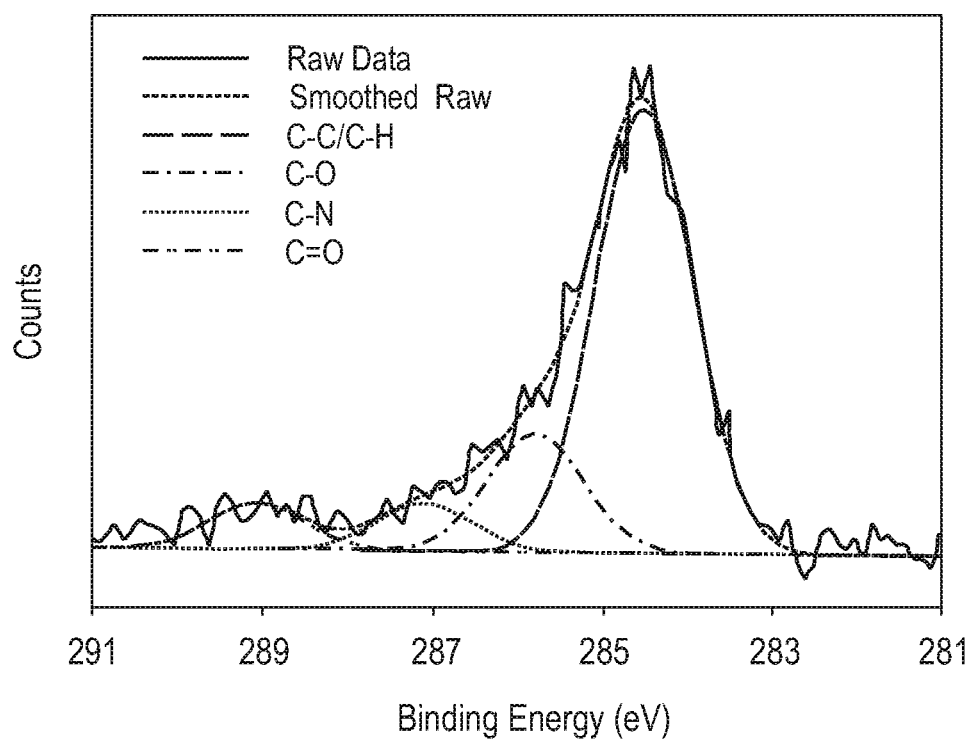
FIG. 1 is an x-ray photoelectron spectroscopy (XPS) carbon is core level spectrum of APSi-C2G. The deconvoluted peaks at 283-286, 284-288, 285-289 and 288-290 eV are attributed to the functional groups of C—C/C—H, C—O, C—N and C=O.

The antimicrobial cationic polymers disclosed herein comprise a cationic repeat unit having a side chain that comprises a protonated form of a guanidine and/or an isothiourea group (i.e., a guanidinium and/or an isothiouronium group, respectively). These cationic groups are directly or indirectly covalently linked to the polymer backbone and are ionically associated with a negative-charged counterion X'. Preferably, X' is a free ion not directly or indirectly covalently linked to the polymer backbone. The polymer backbone portion of the cationic repeat unit preferably comprises a carbonate group and/or a carbamate group (urethane). The cationic polymer can be a polycarbonate, polyurethane, or combination thereof comprising pendent guanidinium and/or isothiouronium groups. The cationic polymers can be highly water-soluble or possess amphiphilic properties conducive to micelle formation in aqueous media. The cationic polymers alone can be potent antimicrobial agents (i.e., when the counterion X' is not an anionic antimicrobial agent). Moreover, the cationic polymers can be active antimicrobial agents when the polymers contain no quaternary amine groups (i.e., an amine comprising a positive-charged nitrogen covalently bonded only to carbons). The cationic polymers can be highly active against Gram-positive microbes (e.g., *Staphylococcus aureus* (*S. aureus*)), Gram-negative microbes (e.g., *Escherichia coli* (*E. coli*), *Pseudomonas aeruginosa* (*P. aeruginosa*)), and fungi (e.g., *Candida albicans* (*C. albicans*)). Additionally, the cationic polymers can be biocompatible, biodegradable, non-hemolytic, and non-cytotoxic at concentrations above the minimum inhibitory concentration (MIC). The cationic polymers are therefore attractive for a wide range of consumer products such as, for example, cosmetics, skin lotions, and antibiotic drugs.

In some instances, the cationic polymers are capable of forming ionic complexes (loaded complexes) with anionic materials (e.g., genes, drugs), making them potentially useful as carriers for delivery of various therapeutic agents.

The term "biodegradable" is defined by the American Society for Testing and Materials as degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

A "biocompatible" material is defined herein as a material capable of performing with an appropriate host response in a specific application.

"Restricted metals" herein include ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. In an embodiment, the chemical formulas of the components used to prepare the water-soluble versions of the cationic polymers contain none of the above restricted metals. Preferably, each one of the foregoing restricted metals has a concentration below detection limits in the water-soluble versions of the cationic polymer. No restriction is placed on the concentration of boron, silicon, or any individual alkali metal in the cationic polymers.

No restriction is placed on the polymer skeletal structure of the cationic polymers. Exemplary non-limiting polymer skeletal structures include linear polymers, branched polymers, star polymers, mykto-arm star polymers, crosslinked polymers, ladder polymers, cyclic polymers, comb polymers, dendritic polymers, and graft polymers. The foregoing polymer types can comprise a homopolymer, random copolymer, or block copolymer chain comprising the cationic repeat unit.

The cationic polymers can comprise non-stereospecific and/or stereospecific repeat units. A stereospecific repeat unit i) has a non-superposable mirror image and ii) comprises one or more asymmetric tetravalent carbons (i.e., tetrahedral sp$^3$ carbons). Each asymmetric tetravalent carbon is assigned an R or S symmetry based on Cahn-Ingold-Prelog (CIP) symmetry rules. For example, a stereospecific repeat unit having one asymmetric tetravalent carbon can be present substantially as the R stereoisomer or substantially as the S stereoisomer, meaning the stereoisomer can be present in a stereoisomeric purity of 90% to 100%, 94% or more, or more particularly 98% to 100%. In another example, if the stereospecific repeat unit has two asymmetric tetravalent carbons, the stereospecific repeat unit can be present as the R,R stereoisomer, substantially as the R,S stereoisomer, substantially as the S,S stereoisomer, or substantially as the S,R stereoisomer.

In a preferred embodiment, the cationic polymer is a linear polymer comprising the cationic repeat unit. Herein, a linear polymer has one branch having two peripheral ends (i.e., dangling ends, as the two ends of a segment of a rope). The one branch can comprise one or more polymer chain segments covalently linked together at respective polymer chain ends by way of any suitable linking group, which can include a single bond. Each polymer chain segment of a linear polymer can comprise a homopolymer, random copolymer, or block copolymer chain comprising one or more repeat units. At least one of the polymer chain segments comprises a cationic repeat unit comprising a pendent hydrosalt of a guanidine and/or isothiourea group.

A hydrosalt of a guanidine functional group comprises a positive-charged protonated form of the guanidine group that is ionically associated with a negative-charged counterion represented herein as X'. A positive-charged protonated guanidine group is referred to herein as a guanidinium group.

A hydrosalt of an isothiourea functional group comprises a positive-charged protonated form of the isothiourea group that is ionically associated with a negative-charged counterion represented herein as X'. A protonated isothiourea group is referred to herein as an isothiouronium group.

A hydrosalt of a guanidine group is represented herein by the structure:

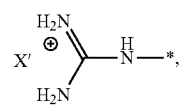

wherein X' is a negative-charged counterion. Herein, a bond with an asterisk is referred to as a starred bond. Starred bonds are not methyl groups. An atomic center having a starred bond indicates the atomic center is covalently linked to another portion of the chemical structure. In the above structure, the nitrogen is covalently linked to another portion of the side chain of the cationic repeat unit.

A hydrosalt of an isothiourea group is represented herein by the structure:

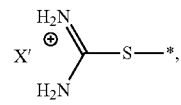

wherein X' is a negative-charged counterion. The sulfur is covalently linked to another portion of the side chain of the cationic repeat unit.

It should be understood that the positive charge is delocalized over the three heteroatoms of the respective cationic group (i.e., the three nitrogens of the guanidinium group, or the two nitrogens and sulfur of the isothiouronium group).

Herein, each negative-charged counterion X' of the cationic polymer is an independent ion. Each X' is also a "free ion", meaning X' is not covalently linked directly or indirectly to the backbone of the cationic polymer. "Directly covalently linked to the backbone" means covalently linked by way of one covalent bond to a nearest atomic center of the backbone. "Indirectly covalently linked to the backbone" means covalently linked to a nearest atomic center of the backbone by way of two or more covalent bonds and one or more intervening atomic centers.

The cationic polymers comprise a cationic subunit of formula (A-1):

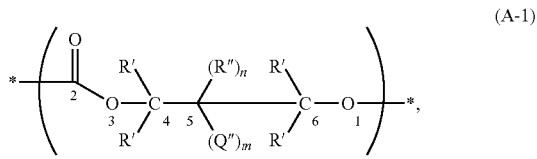

(A-1)

wherein
atoms 1-6 are backbone atoms of the cationic polymer,
m is 1 or 2,
n is 0 or 1, wherein when m is 2, n is 0,
each R' is an independent monovalent radical selected from the group consisting of hydrogen and alkyl groups comprising 1 to 6 carbons,
R" is a monovalent radical selected from the group consisting of hydrogen and alkyl groups comprising 1 to 6 carbons, and
each Q" is an independent group comprising a guanidinium and/or an isothiouronium group.

The cationic subunit can be a repeat unit of the cationic polymer (e.g., as in a polycarbonate) or a portion of a repeat unit of the cationic polymer (e.g., as in a polyurethane repeat unit described further below). The cationic subunits of formula can independently be stereospecific or non-stereospecific.

More specific cationic subunits have a structure in accordance with formula (A-2):

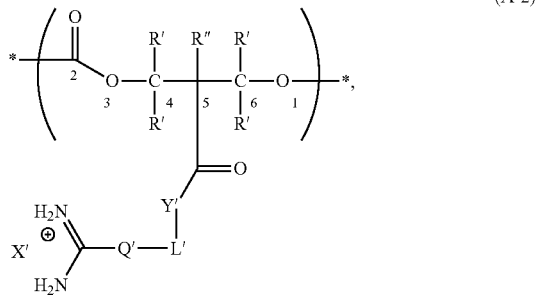

(A-2)

wherein
atoms 1-6 are backbone atoms of the cationic polymer,
L' is a divalent hydrocarbon radical comprising 2 to 30 carbons,
Q' is *—N(H)—* or *—S—*,
each R' is an independent monovalent radical selected from the group consisting of hydrogen and alkyl groups comprising 1 to 6 carbons,
R" is a monovalent radical selected from the group consisting of hydrogen and alkyl groups comprising 1 to 6 carbons,
X' is a negative-charged counterion, and
Y' is *—O—* or *—N(H)—*.

Exemplary non-limiting L' groups include 1,2-ethylene, 1,2-propylene, 1,3-propylene, 1,2-butylene, 1,3-butylene, 1,4-butylene, 1,2-pentylene, 1,3-pentylene, 1,4-pentylene, 1,5-pentylene, 1,2-cyclohexylene, 1,3-cyclohexylene, 1,4-cyclohexylene, 1,2-phenylene, 1,3-phenylene, and 1,4-phenylene.

In an embodiment, L' is an alkylene group of formula (A-3):

(A-3)

wherein n is an integer having a value of 2 to 6. In another embodiment, L' is 1,2-ethylene.

Exemplary non-limiting R' groups include methyl, ethyl, propyl, butyl, pentyl, and hexyl. In an embodiment, each R' is hydrogen.

Exemplary non-limiting R" groups include methyl, ethyl, propyl, butyl, pentyl, and hexyl. In an embodiment, R" is methyl or ethyl.

Non-limiting exemplary negative-charged counterions X' include halides (e.g., fluoride, chloride, bromide, iodide), hydroxide, alkyl and aryl carboxylates (e.g., trifluoroacetate, pentafluorobenzoate), hydrogen carbonate, alkyl and aryl sulfonates (e.g., methanesulfonate, p-toluenesulfonate), methyl sulfate, hydrogen sulfate, nitrate, dihydrogen phosphate, dialkyl and diaryl phosphates, and alkyl and aryl phosphonates. In an embodiment, X' is trifluoroacetate.

Other cationic subunits can have a structure according to formula (A-4):

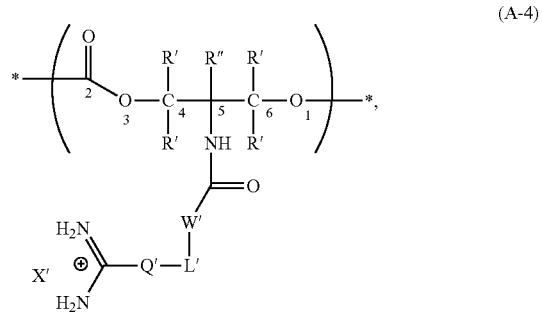

(A-4)

wherein
wherein atoms 1-6 are backbone atoms of the cationic polymer,
L' is a divalent hydrocarbon radical comprising 2 to 30 carbons, Q' is *—N(H)—* or *—S—*, R' is a monovalent radical selected from the group consisting of hydrogen and alkyl groups comprising 1 to 6 carbons, R" is a monovalent radical selected from the group consisting of hydrogen and alkyl groups comprising 1 to 6 carbons, X' is a negative-charged counterion, and W' is a single bond, *—O—* or *—N(H)—*.

Subunits of formula (A-4) can be cationic repeat units or a portion of a cationic repeat unit of the cationic polymer. In an embodiment, W' is *—O—*, R" is hydrogen, one R' is methyl, and the remaining R' groups are hydrogen. Serinol and/or threoninol provide useful starting materials for the formation of cationic subunits of formula (A-4). Subunits of formula (A-4) can independently be stereospecific or non-stereospecific.

The cationic polymer can comprise the cationic subunits singularly or in combination. In an embodiment, the cationic polymer is a cationic polycarbonate comprising cationic subunits of formula (A-2) and/or (A-4), and atoms 1-6 of formulas (A-2) and (A-4) are backbone atoms of the cationic polycarbonate.

Guanidinium- and isothiouronium-functionalized polycarbonates

More specific linear antimicrobial cationic polymers have a structure in accordance with formula (B-1):

$$Z'—P'—Z''  \quad (B\text{-}1),$$

wherein

Z' is a monovalent first end group comprising 1 to 40 carbons,

Z" is a monovalent second end group selected from the group consisting of hydrogen and groups comprising 1 to 40 carbons, and P' is a polymer chain comprising an above-described cationic subunit, wherein the subunit comprises i) a backbone portion, which is a segment of the P' backbone and ii) a side chain portion covalently linked to the backbone portion, the side chain portion comprising one or more guanidinium and/or isothiouronium groups ionically associated with respective independent negative-charged counterions X'.

P' can be a homopolymer, random copolymer, or block copolymer chain comprising the cationic subunit. Z' can be a residue of an initiator used to prepare P' by ring opening polymerization. Z" can be an endcap group. In an embodiment, P' is a polycarbonate chain comprising cationic repeat units of formula (A-2) and/or formula (A-4).

Another more specific linear cationic polymer has a structure in accordance with formula (B-2):

$$Z^b—P^b—C'—P^b—Z^b  \quad (B\text{-}2),$$

wherein each $P^b$ is an independent polymer chain comprising an above-described cationic subunit, wherein the cationic subunit comprises i) a backbone portion, which is a segment of the $P^b$ backbone and ii) a side chain portion covalently linked to the backbone portion, the side chain portion comprising one or more guanidinium and/or isothiouronium groups ionically associated with respective independent negative-charged counterions X', C' is a divalent linking group (core group) comprising 2 to 25 carbons, wherein C' comprises two heteroatoms independently selected from the group consisting of nitrogen, oxygen, and sulfur, wherein the heteroatoms are covalently linked to respective polymer chains $P^b$, and each $Z^b$ is an independent monovalent end group selected from the group consisting of hydrogen and groups comprising 1 to 40 carbons.

Cationic polymers of formula (B-2) are also referred to herein as 2-armed linear polymers, due to the separation of polymer chains $P^b$ by core group C'. Preferably, each of the two heteroatoms of C' are oxygen (*—O—*). C' can be a residue of a diol initiator used to form $P^a$ and $P^b$ by organocatalyzed ring opening polymerization.

Each $P^b$ can be a homopolymer, a random copolymer, or a block copolymer chain comprising an above-described cationic subunit. In another embodiment, each $P^b$ has the same chemical structure. In another embodiment, each $Z^b$ is hydrogen and each $P^b$ has a terminal hydroxy group.

The cationic polymer can further comprise a non-charged repeat unit, referred to herein as diluent repeat unit. The diluent repeat unit can be used, for example, to adjust the amphiphilic properties (i.e., hydrophobic/hydrophilic balance) of the cationic polymer. Preferably, the diluent repeat unit is formed by ring opening polymerization of a diluent cyclic carbonate monomer, described in more detail below. Diluent repeat units can independently be stereospecific or non-stereospecific.

Preparation of Cationic Polymers

Preferably, the cationic polymers that are polycarbonates are prepared by organocatalyzed ring opening polymerization (ROP) of a cyclic carbonate monomer bearing a pendent protected guanidine group, referred to herein for brevity as the "guanidine monomer". The ROP produces an initial polymer containing a protected guanidine group. Subsequent deprotection of the initial polymer using a protic acid forms an antimicrobial cationic polymer bearing pendent guanidinium groups. The protic acid can have one or more protons, which can be donated to form a hydrosalt of a guanidine and/or an isothiourea group. In this instance, the negative-charged counterion X' is a conjugate base of a protic acid. Exemplary protic acids include hydrochloric acid, hydrobromic acid, sulfuric acid, phosphoric acid, trifluoroacetic acid, methanesulfonic acid, and p-toluenesulfonic acid.

The ROP reaction mixture comprises the guanidine monomer, a nucleophilic initiator for the ROP, an organocatalyst, a solvent, and, optionally, an accelerator.

The guanidine monomer can have a structure according to formula (M-1):

(M-1)

[Chemical structure showing a cyclic carbonate with positions 1-6, substituents R', R", and a side chain with B'—N, B'—NH, H—N—L', and Y=O groups]

wherein
ring atoms are numbered 1 to 6,
each B' is an independent acid-labile protecting group,
L' is a divalent hydrocarbon radical comprising 2 to 30 carbons,
each R' is an independent monovalent radical selected from the group consisting of hydrogen and alkyl groups comprising 1 to 6 carbons,
R" is a monovalent radical selected from the group consisting of hydrogen and alkyl groups comprising 1 to 6 carbons, and
Y' is *—O—* or *—N(H)—*.

It should be understood that the following tautomers of the protected guanidine group are equivalent.

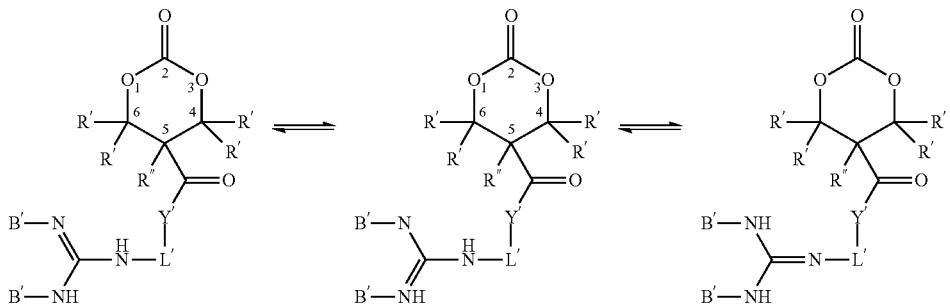

Ring opening polymerization of the protected guanidine monomer of formula (M-1) produces a protected repeat unit of formula (M-2):

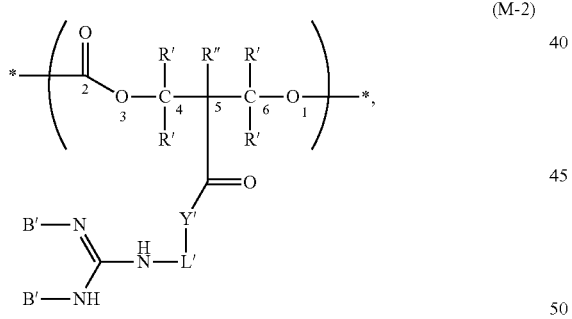

(M-2)

wherein
each B' is an independent acid-labile protecting group,
L' is a divalent hydrocarbon radical comprising 2 to 30 carbons,
each R' is an independent monovalent radical selected from the group consisting of hydrogen and alkyl groups comprising 1 to 6 carbons,
R" is a monovalent radical selected from the group consisting of hydrogen and alkyl groups comprising 1 to 6 carbons,
Y' is *—O—* or *—N(H)—*.

Exemplary protecting groups B' for a guanidine nitrogen include benzyloxycarbonyl (Bnoc), tert-butyloxycarbonyl (tBoc, also referred to as "Boc"), and fluorenyloxycarbonyl (Fmoc) as shown below.

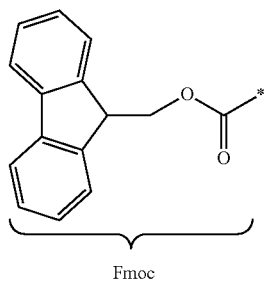

Bnoc            tBoc (Boc)

-continued

Fmoc

The Bnoc protecting group can be removed by acidolysis or catalytic hydrogenation. The Boc protecting group can be removed by acidolysis. The Fmoc protecting group can be removed by base, typically a secondary amine. Preferably, B' is a Boc group. The Boc-protected guanidine nitrogen can be deprotected by treatment with a fluorinated carboxylic acid. Preferably, the fluorinated carboxylic acid is trifluoroacetic acid.

Preferred guanidine monomers have structures according to formula (M-3):

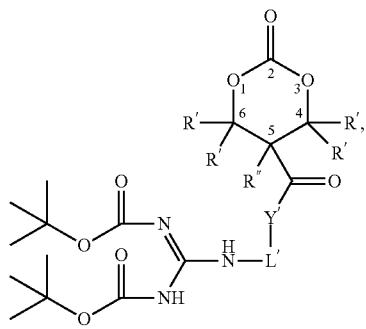
(M-3)

wherein

L' is a divalent hydrocarbon radical comprising 2 to 30 carbons, each R' is an independent monovalent radical selected from the group consisting of hydrogen and alkyl groups comprising 1 to 6 carbons, R" is a monovalent radical selected from the group consisting of hydrogen and alkyl groups comprising 1 to 6 carbons, Y' is *—O—* or *—N(H)—*.

Other protected guanidine monomers can have a structure according to formula (M-4):

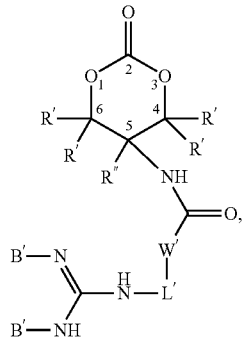
(M-4)

wherein each B' is an independent acid-labile protecting group,

L' is a divalent hydrocarbon radical comprising 2 to 30 carbons, each R' is an independent monovalent radical selected from the group consisting of hydrogen and alkyl groups comprising 1 to 6 carbons, R" is a monovalent radical selected from the group consisting of hydrogen and alkyl groups comprising 1 to 6 carbons, W' is a single bond, *—O—*, or *—N(H)—*.

Ring opening polymerization of guanidine monomers of formula (M-4) produces a repeat unit of formula (M-5):

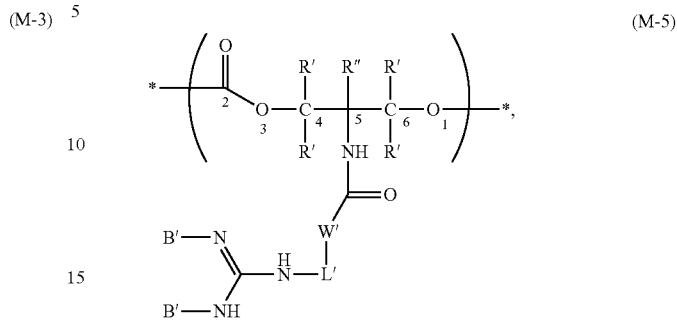
(M-5)

wherein each B' is an independent acid-labile protecting group,

L' is a divalent hydrocarbon radical comprising 2 to 30 carbons, each R' is an independent monovalent radical selected from the group consisting of hydrogen and alkyl groups comprising 1 to 6 carbons, R" is a monovalent radical selected from the group consisting of hydrogen and alkyl groups comprising 1 to 6 carbons, W' is a single bond, *—O—*, or *—N(H)—*.

Exemplary non-limiting Boc-protected guanidine monomers include those of Scheme 1, where n is an integer of 1 to 6.

Scheme 1.

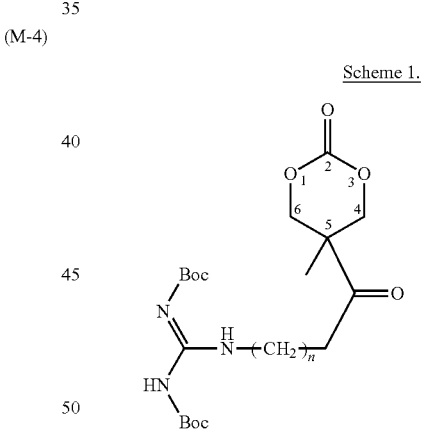

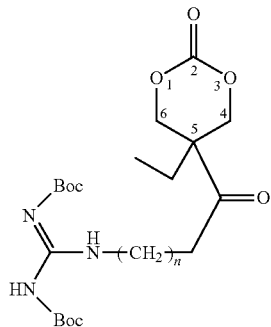

-continued

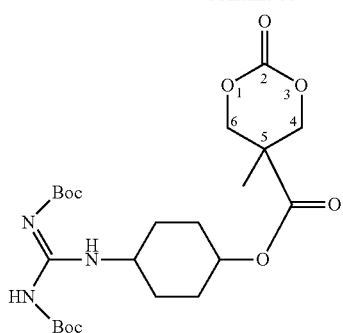

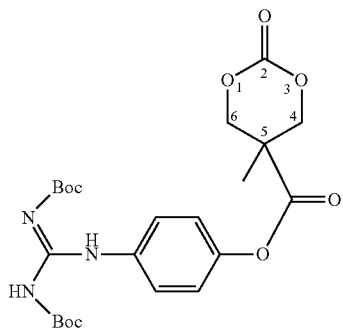

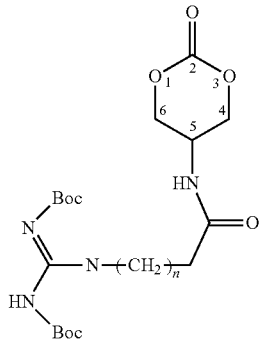

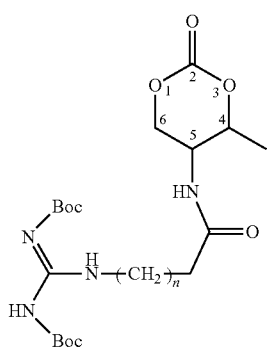

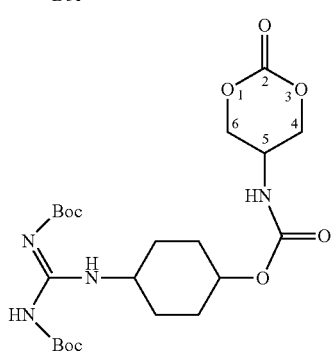

-continued

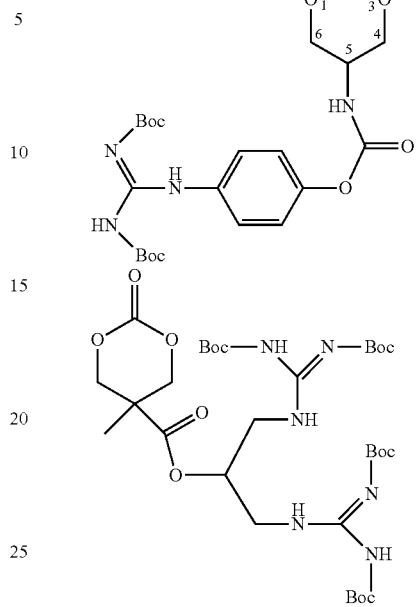

The guanidine monomers can independently be stereospecific or non-stereospecific.

A second method of preparing the cationic polymers comprises polymerizing by organocatalyzed ROP a cyclic carbonate monomer bearing a pendent leaving group, which is capable of undergoing a nucleophilic substitution reaction with thiourea to form an isothiouronium group ionically associated with X', wherein X' is an anionic form of the leaving group (X' is also a conjugate base of a protic acid). The cyclic carbonate monomer bearing the pendent leaving group is referred to herein as the "electrophilic monomer". Organocatalyzed ROP of the electrophilic monomer produces an initial polymer comprising an electrophilic repeat unit. The electrophilic repeat unit comprises a side chain bearing the leaving group. Treatment of the initial polymer with thiourea produces the antimicrobial cationic polymer bearing pendent isothiouronium groups.

The electrophilic repeat unit can be stereospecific or non-stereospecific.

More specific electrophilic monomers are cyclic carbonates having a structure according to formula (M-6):

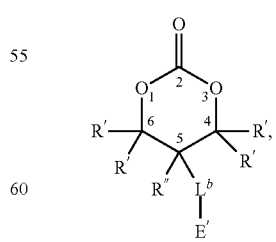

(M-6)

wherein
the ring atoms are shown numbered 1 to 6,
$L^b$ is a divalent linking group comprising 1 or more carbons, E' is a substituent capable of undergoing a nucleophilic substitution reaction with thiourea to form an isothiouronium group, each R' is an independent monovalent radical selected from the group consisting of hydrogen and alkyl groups comprising 1 to 6 carbons, and R" is a monovalent radical selected from the group consisting of hydrogen and alkyl groups comprising 1 to 6 carbons.

Other more specific electrophilic monomers have a structure in accordance with formula (M-7):

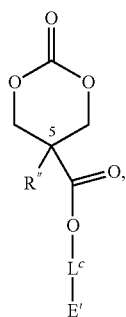

(M-7)

wherein
ring atom 5 is labeled,
$L^c$ is a divalent linking group comprising 2 to 30 carbons,
E' is a substituent capable of undergoing a nucleophilic substitution reaction with thiourea to form an isothiouronium group, and
R" is a monovalent radical selected from the group consisting of hydrogen, halogens, and alkyl groups comprising 1 to 6 carbons.

Ring opening polymerization of electrophilic monomers of formula (M-7) produces an initial polymer comprising an electrophilic repeat unit according to formula (M-8):

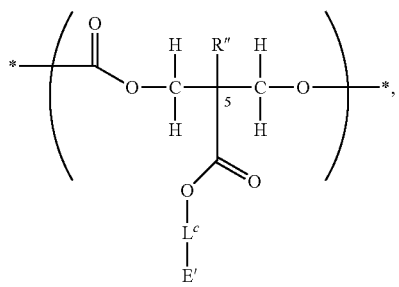

(M-8)

wherein
backbone atom 5 is labeled,
$L^c$ is a divalent linking group comprising 2 to 30 carbons,
E' is a substituent capable of undergoing a nucleophilic substitution reaction with thiourea to form an isothiouronium group, and
R" is a monovalent radical selected from the group consisting of hydrogen, halogens, and alkyl groups comprising 1 to 6 carbons.

Other more specific electrophilic monomers have a structure according to formula (M-9):

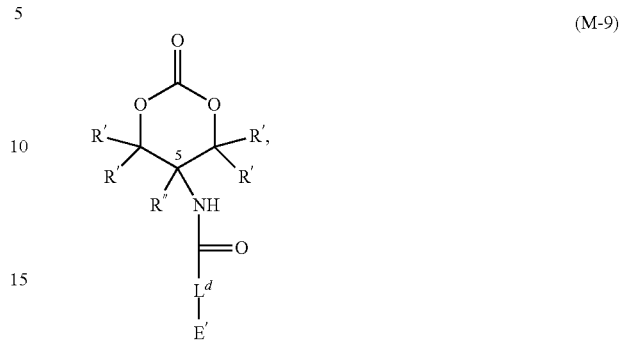

(M-9)

wherein
ring atom 5 is labeled,
$L^d$ is a divalent linking group comprising 2 to 30 carbons,
E' is a substituent capable of undergoing a nucleophilic substitution reaction with thiourea to form an isothiouronium group,
each R' is an independent monovalent radical selected from the group consisting of hydrogen, halogens, methyl, and ethyl, and
R" is a monovalent radical selected from the group consisting of hydrogen, halogens, and alkyl groups comprising 1 to 6 carbons.

Ring opening polymerization of electrophilic monomers of formula (M-9) produces an initial polymer comprising an electrophilic repeat unit of formula (M-10):

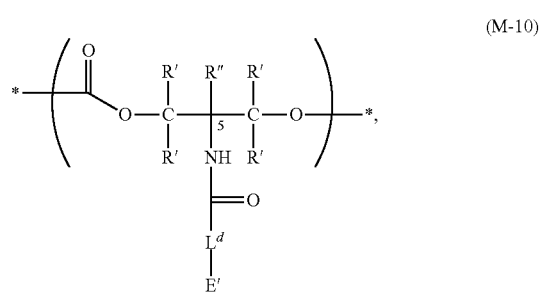

(M-10)

wherein
backbone atom 5 is labeled,
$L^d$ is a divalent linking group comprising 2 to 30 carbons,
E' is a substituent capable of undergoing a nucleophilic substitution reaction with thiourea to form an isothiouronium group,
each R' is an independent monovalent radical selected from the group consisting of hydrogen, halogens, methyl, and ethyl, and
R" is a monovalent radical selected from the group consisting of hydrogen, halogens, and alkyl groups comprising 1 to 6 carbons.

Even more specific electrophilic monomers include the cyclic carbonate monomers of Scheme 2.

Scheme 2.
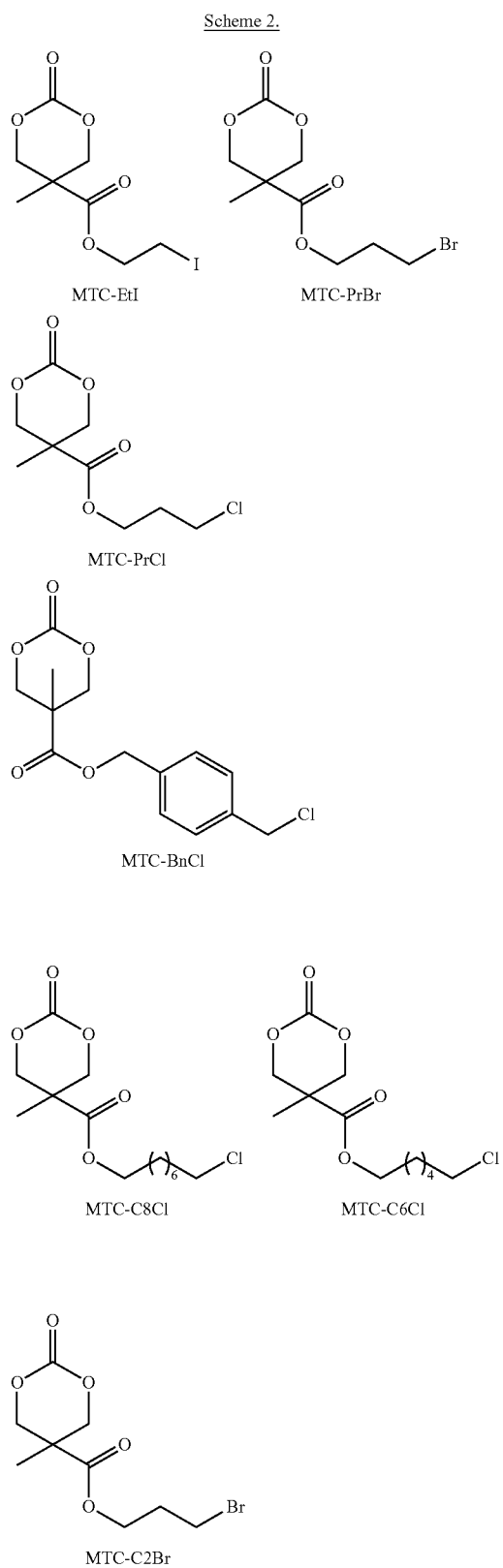
Scheme 3.
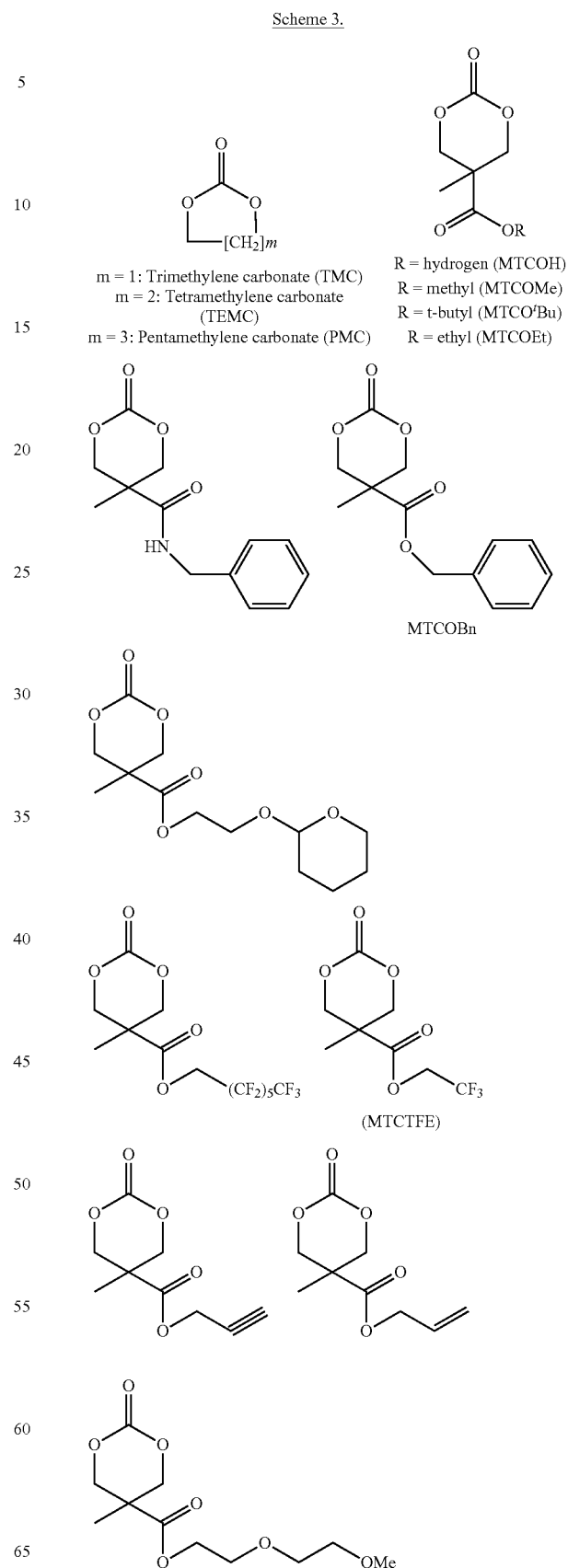
Other cyclic carbonate monomers can serve as diluent comonomers. Exemplary non-limiting diluent cyclic carbonate comonomers include the compounds of Scheme 3.

23
-continued

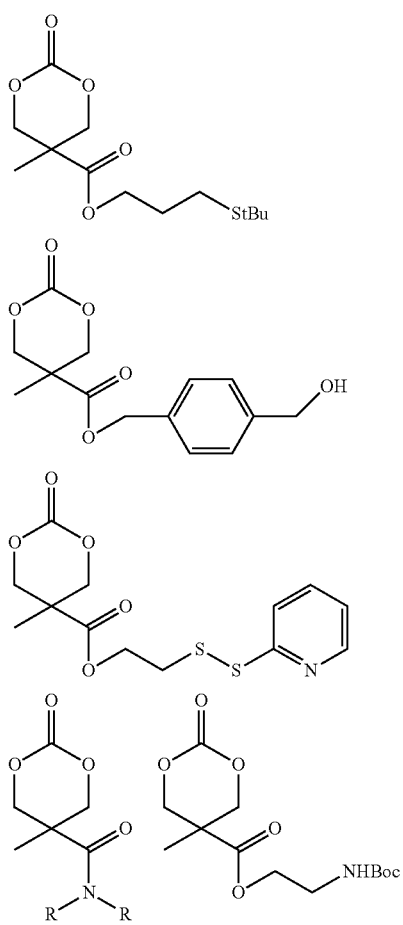

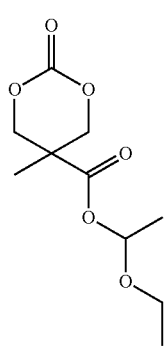

MTCOEE

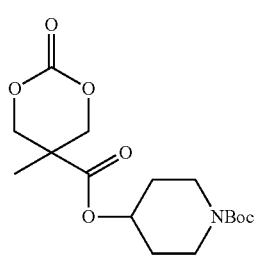

24
-continued

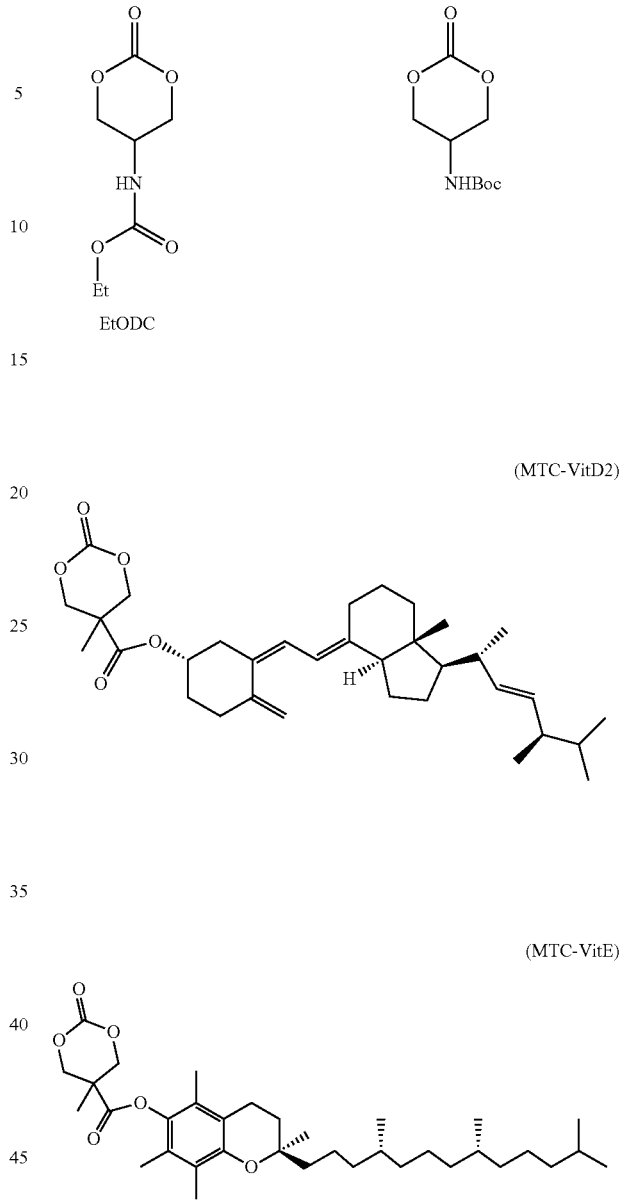

(MTC-VitD2)

(MTC-VitE)

Cyclic ester comonomers can serve as diluent comonomers. Exemplary diluent cyclic ester comonomers include the compounds of Scheme 4.

Scheme 4.

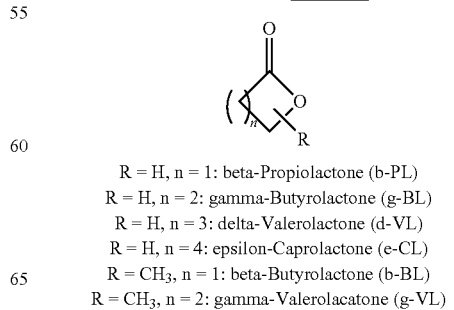

R = H, n = 1: beta-Propiolactone (b-PL)
R = H, n = 2: gamma-Butyrolactone (g-BL)
R = H, n = 3: delta-Valerolactone (d-VL)
R = H, n = 4: epsilon-Caprolactone (e-CL)
R = CH$_3$, n = 1: beta-Butyrolactone (b-BL)
R = CH$_3$, n = 2: gamma-Valerolacatone (g-VL)

-continued

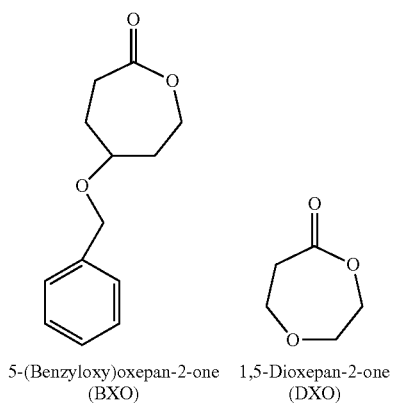

5-(Benzyloxy)oxepan-2-one (BXO)   1,5-Dioxepan-2-one (DXO)

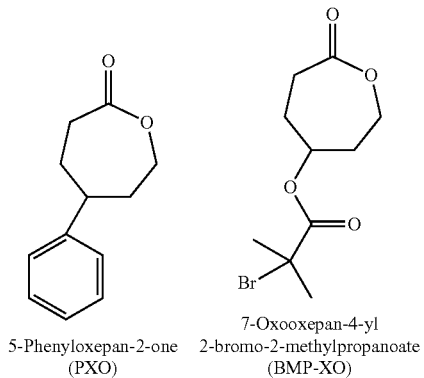

5-Phenyloxepan-2-one (PXO)   7-Oxooxepan-4-yl 2-bromo-2-methylpropanoate (BMP-XO)

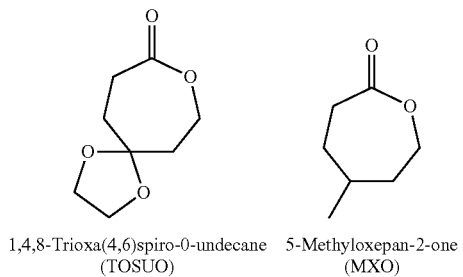

1,4,8-Trioxa(4,6)spiro-0-undecane (TOSUO)   5-Methyloxepan-2-one (MXO)

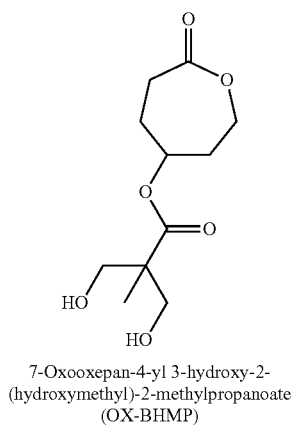

7-Oxooxepan-4-yl 3-hydroxy-2-(hydroxymethyl)-2-methylpropanoate (OX-BHMP)

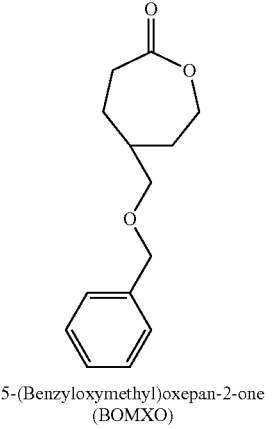

5-(Benzyloxymethyl)oxepan-2-one (BOMXO)

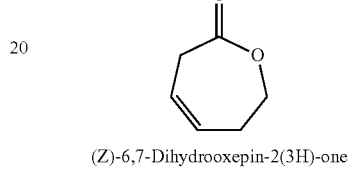

(Z)-6,7-Dihydrooxepin-2(3H)-one (DHXO)

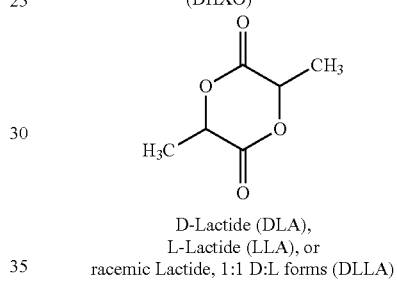

D-Lactide (DLA), L-Lactide (LLA), or racemic Lactide, 1:1 D:L forms (DLLA)

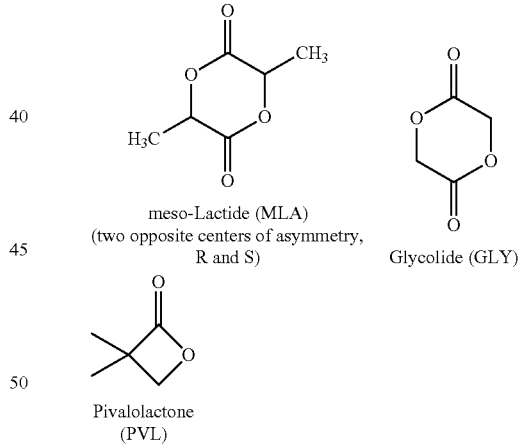

meso-Lactide (MLA) (two opposite centers of asymmetry, R and S)   Glycolide (GLY)

Pivalolactone (PVL)

When cyclic ester diluent comonomers are used, the resulting cationic polymers are referred to as polyestercarbonates.

The above cyclic carbonyl monomers can be purified by recrystallization from a solvent such as ethyl acetate or by other known methods of purification, with particular attention being paid to removing as much water as possible from the comonomer. The comonomer moisture content can be from 1 to 10,000 ppm, 1 to 1,000 ppm, 1 to 500 ppm, and most specifically 1 to 100 ppm, by weight of the monomer.

ROP Initiators

The ROP reaction mixture comprises an initiator. The initiator becomes a chain fragment that is covalently linked to a repeat unit of the ring opened polymer chain. Initiators for ring opening polymerizations generally include nucleophilic groups such as alcohols, primary amines, secondary amines, thiols, and combinations thereof. The initiator can comprise one or more active nucleophilic initiator groups. The initiator can be polymeric or non-polymeric. For example, the initiator can be a polyether having a terminal alcohol, polyether having a terminal amine group, or a polymer having a terminal thiol group.

More particularly, the initiator for the ring opening reaction is an alcohol. The alcohol initiator can be any suitable alcohol, including mono-alcohol, diol, triol, or other polyol. The alcohol can be multi-functional comprising, in addition to one or more hydroxyl groups, a halide, an ether group, an ester group, an amide group, or other functional group. Exemplary alcohols includes methanol, ethanol, propanol, butanol, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol and other aliphatic saturated alcohols, cyclopentanol, cyclohexanol, cycloheptanol, cyclooctanol and other aliphatic cyclic alcohols; phenol, substituted phenols, benzyl alcohol, substituted benzyl alcohol, benzenedimethanol, trimethylolpropane, a saccharide, or a combination thereof. Monomeric diol initiators include ethylene glycols, propylene glycols, hydroquinones, and resorcinols. Another example of a diol initiator is BnMPA, derived from 2,2-dimethylol propionic acid.

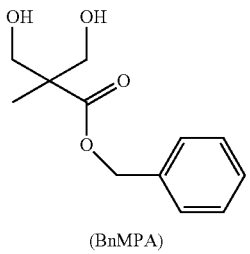 [SMILES: CC(CO)(CO)C(=O)OCc1ccccc1]

(BnMPA)

BnMPA is a precursor used in the preparation of cyclic carbonate monomers.

The ROP initiator can comprise a covalently bound form of a biologically active compound selected from the group consisting of steroids, non-steroid hormones, vitamins, and drugs. For example, mono-nucleophilic ROP initiators include cholesterol, alpha-tocopherol, and ergocalciferol.

The initiator can include protected nucleophilic ROP initiator groups that include protected thiols, protected amines, and protected alcohols.

Exemplary mono-nucleophilic polymeric ROP initiators include mono-endcapped poly(ethylene glycols) (e.g., mono-methyl poly(ethylene glycol) (mPEG-OH)) and mono-endcapped poly(propylene glycols).

Exemplary di-nucleophilic polyether ROP initiators include poly(ethylene glycol) (referred to as "PEG-diol", "PEG" or "HO-PEG-OH") having the structure HO—[CH$_2$CH$_2$O]$_n$—H and poly(propylene glycol) (referred to as "PPG" or "HO-PPG-OH") having the structure HO—[CH$_2$C(H)(CH$_3$)O]$_n$—H, and copolyethers comprising ethylene oxide and propylene oxide repeat units. The number average molecular weight (Mn) of the di-nucleophilic polyether initiator can be from 100 to 10000, and even more specifically, 1000 to 5000.

Other ROP initiators include particles comprising a core material and one or more independent surface groups capable of initiating a ROP, wherein the surface groups are covalently linked to the core. The surface groups can comprise nucleophilic alcohol, amine, and/or thiol groups for initiating a ROP. The core material can be an organic, inorganic, and/or organometallic material that is covalently linked to the surface groups. More specific core materials include dendritic polymers having surface groups comprising terminal alcohol and/or amine groups. Other core materials include silica particles and/or silica gel particles that have been surface-modified to contain nucleophilic amine-, thiol-, and hydroxy-containing surface groups (e.g., 3-aminopropyl-functionalized silica gel sold by Sigma-Aldrich). The median particle size of the ROP particle initiator can be in a range of about 5 nm to 200 micrometers. The ROP particle initiator comprises at least one nucleophilic group for initiating a ROP.

In an embodiment, the ROP initiator is a mono-alcohol comprising 1 to 40 carbons. In another embodiment the ROP initiator is silica particle comprising primary amine and/or alcohol surface groups. In another embodiment, the ROP initiator is selected from the group consisting of poly (ethylene glycol), amine-terminated poly(ethylene glycol) (PEG-diamine), and mono-methyl endcapped poly(ethylene glycol) (MPEG-OH), which are commercially available in different average molecular weights.

Endcap Agents

Optionally, the initial polymer (i.e., prior to deprotection) formed by the ROP can be endcapped. An endcap agent can prevent further chain growth and stabilize the reactive end groups, minimizing unwanted side reactions such as chain scission during and/or after the deprotection step or treatment with thiourea. Endcap agents include, for example, materials for converting terminal hydroxyl groups to esters, such as carboxylic acid anhydrides, carboxylic acid chlorides, or reactive esters (e.g., p-nitrophenyl esters). In an embodiment, the endcap agent is acetic anhydride, which converts reactive hydroxy end groups to acetate ester groups. The endcap group can be a biologically active moiety.

Ring Opening Polymerizations (ROP)

The following general description of methods, conditions and materials for ring opening polymerizations is applicable to the preparation of the initial polymers.

The ring-opening polymerization can be performed at a temperature that is about ambient temperature or higher, 15° C. to 40° C., and more specifically 20° C. to 40° C. Reaction times vary with solvent, temperature, agitation rate, pressure, and equipment, but in general the polymerizations are complete within 1 to 100 hours.

The ROP reaction is performed with a solvent. Solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. A suitable monomer concentration is 0.1 to 5 moles per liter, and more particularly 0.2 to 4 moles per liter.

The ROP polymerizations are conducted under an inert (i.e., dry) atmosphere, such as nitrogen or argon, and at a pressure of from 100 to 500 MPa (1 to 5 atm), more typically at a pressure of 100 to 200 MPa (1 to 2 atm). At the completion of the reaction, the solvent can be removed using reduced pressure.

ROP Catalysts

The catalyst is an organocatalyst whose chemical formula contains none of the restricted metals described further above. Examples of organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexyl-thiourea (TU):

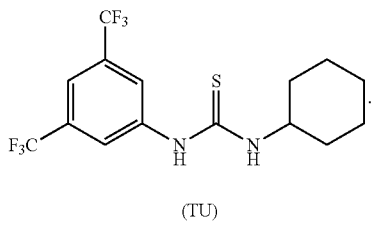 [SMILES: FC(F)(F)c1cc(NC(=S)NC2CCCCC2)cc(C(F)(F)F)c1 ; "(TU)"]

(TU)

Other ROP organocatalysts comprise at least one 1,1,1,3,3,3-hexafluoropropan-2-ol-2-yl (HFP) group. Singly-donating hydrogen bond catalysts have the formula (C-1):

$$R^2\text{—}C(CF_3)_2OH \qquad (C\text{-}1),$$

wherein $R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Scheme 5.

Scheme 5.

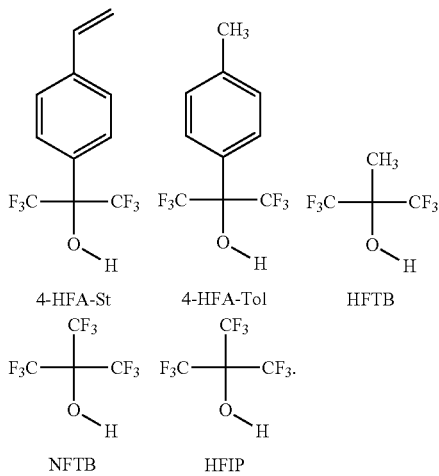

Doubly-donating hydrogen bonding catalysts have two HFP groups, represented by the general formula (C-2):

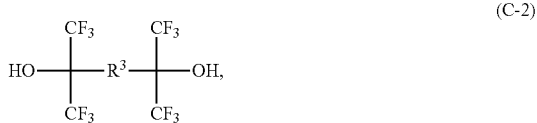

(C-2)

wherein $R^3$ is a divalent radical bridging group containing from 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (C-2) include those listed in Scheme 6. In a specific embodiment, $R^2$ is an arylene or substituted arylene group, and the HFP groups occupy positions meta to each other on the aromatic ring.

Scheme 6.

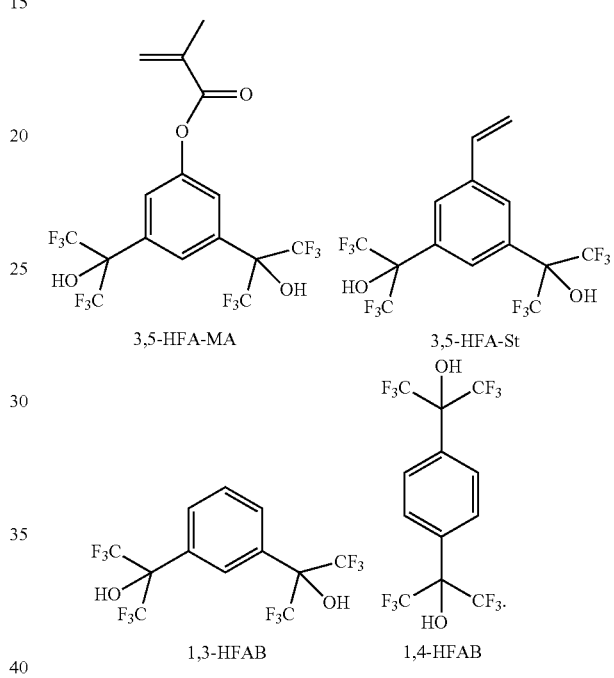

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (e.g., the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, two or more organocatalysts together. The ROP catalyst is added in a proportion of 1/20 to 1/40,000 moles relative to the cyclic carbonyl monomers, and preferably in a proportion of 1/1,000 to 1/20,000 moles relative to the cyclic carbonyl monomers.

ROP Accelerators

The ROP polymerization can be conducted in the presence of an optional accelerator, in particular a nitrogen base. Exemplary nitrogen base accelerators are listed below and include pyridine (Py), N,N-dimethylaminocyclohexane (Me$_2$NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof, shown in Scheme 7.

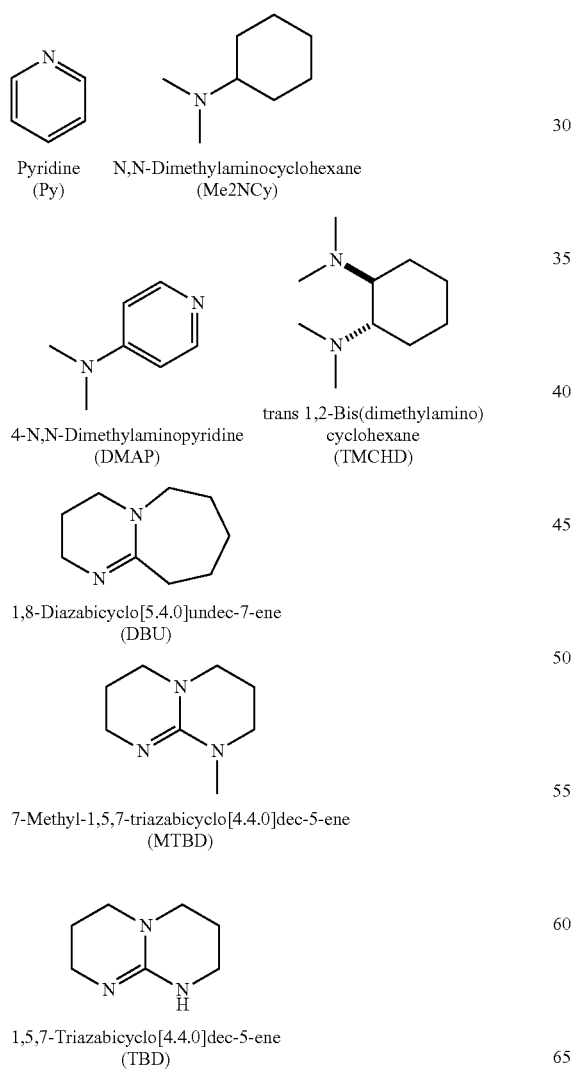

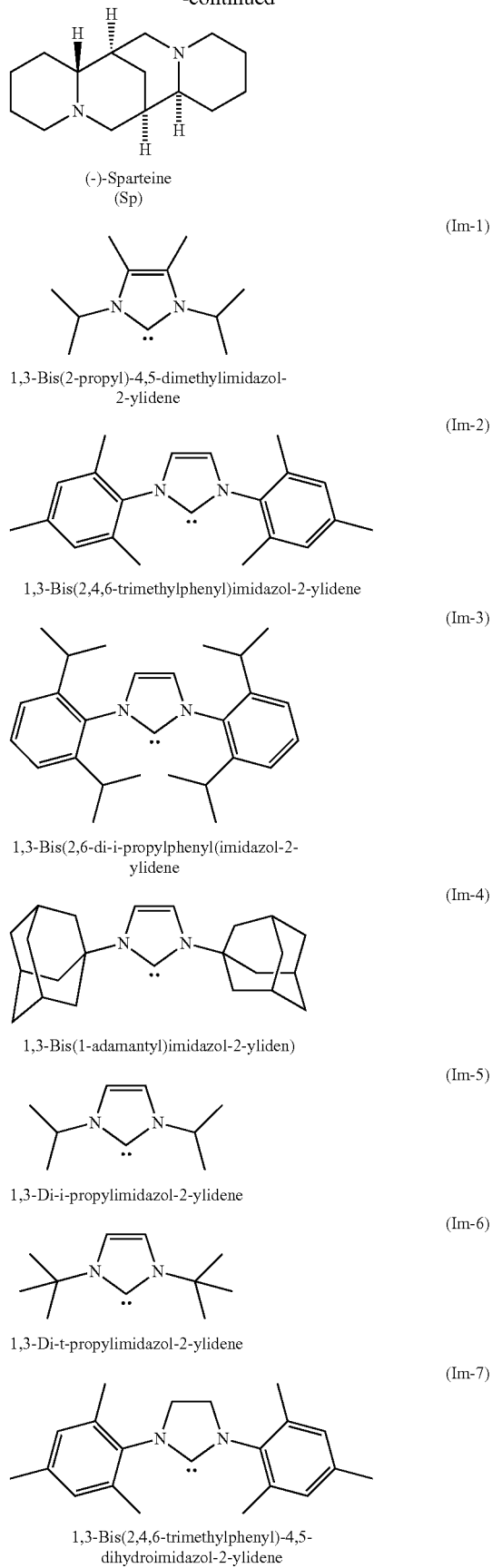

(Im-8)

1,3-Bis(2,6-di-i-propylphenyl)-4,5-dihydroimidazol-2-ylidene

In an embodiment, the accelerator has two or three nitrogens, each capable of participating as a Lewis base, as for example in the structure (−)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The amount of initiator is calculated based on the equivalent molecular weight per participating nucleophilic initiator group in the ring opening polymerization. The participating initiator groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomers used in the polymerization. For example, if the molecular weight of the initiator is 100 g/mole and the initiator has two participating hydroxyl initiator groups, the equivalent molecular weight per hydroxyl group is 50 g/mole. If the polymerization calls for 5 mol % reactive hydroxyl groups per mole of cyclic carbonyl monomers, the amount of initiator is 0.05×50=2.5 g per mole of cyclic carbonyl monomers.

In a specific embodiment, the catalyst is present in an amount of 0.2 to 20 mol %, the nitrogen base accelerator is present in an amount of 0.1 to 5.0 mol %, and the participating nucleophilic initiator groups of the initiator are present in an amount of 0.1 to 5.0 mol % based on the equivalent molecular weight per participating nucleophilic initiator group of the initiator.

The catalysts can be removed by selective precipitation or in the case of the solid supported catalysts, by filtration. The initial polymer formed by the ROP can comprise residual catalyst in an amount greater than 0 wt % (weight percent), based on total weight of the initial polymer and the residual catalyst.

Average Molecular Weight

The cationic polymers and/or the protected initial polymers preferably have a number average molecular weight (Mn) as determined by size exclusion chromatography of at least 1500 g/mol, more specifically 1500 g/mol to 1,000,000 g/mol, 4000 g/mol to 150000 g/mol, or 4000 g/mol to 50000 g/mol. In an embodiment, the cationic polymer and/or the initial polymer has a number average molecular weight of 4,000 to 15,000 g/mole. The cationic polymer and/or the initial polymer also preferably has a narrow polydispersity index (PDI), generally from 1.01 to 2.0, more particularly 1.01 to 1.30, and even more particularly 1.01 to 1.25.

The surface modified particles can comprise surface groups, wherein each surface group comprises a cationic polymer portion. In this instance, the cationic polymer portion can comprise 5 to 100 cationic repeat units, more preferably 5 to 30 cationic repeat units.

Guanidinium- and Isothiouronium-Functionalized Polyurethanes

Also disclosed are cationic polyurethanes having a cationic repeat unit according to formula (U-1):

(U-1)

wherein m is integer having a value of 1 or 2, n is 0 or 1, wherein when m is 2, n is 0, each R' is an independent monovalent radical selected from the group consisting of hydrogen and alkyl groups comprising 1 to 6 carbons, R'' is a monovalent radical selected from the group consisting of hydrogen and alkyl groups comprising 1 to 6 carbons, $Z^a$ is a divalent hydrocarbon radical comprising 2 to 20 carbons, and each Q'' is an independent group comprising a guanidinium and/or isothiouronium group.

$Z^a$ can be aliphatic, cycloaliphatic, aromatic, or a combination thereof. In an embodiment $Z^a$ is 1,5,5-trimethyl-cyclohexane-1,3-diyl:

More specific Q'' groups have a formula (U-2):

$$*-L^5-G^5 \qquad (U-2),$$

wherein $L^5$ is a single bond or a divalent linking group comprising 1 to 10 carbons, wherein $L^5$ is linked to carbon 5 of formula (U-1), and each $G^5$ comprises a guanidinium and/or an isothiouronium group.

In an embodiment, $L^5$ is a single bond or a methylene group. In another embodiment, m is 2, each $L^5$ is methylene, and each $G^5$ comprises an isothiouronium group.

In another embodiment, each $G^5$ is selected from the group consisting of

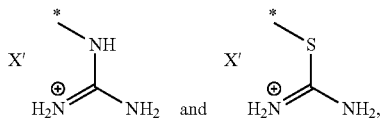

wherein each X' is a negative-charged counterion.

The guanidinium-functionalized cationic polyurethanes can be prepared by treating a diisocyanate with a diol comprising a pendent Boc-protected guanidine group, thereby forming an initial polyurethane comprising Boc-protected guanidine groups. Deprotection of the initial polyurethane using a protic acid forms a cationic polyurethane comprising pendent guanidinium groups.

The isothiouronium-functionalized cationic polyurethanes can be prepared by treating a diisocyanate with a diol comprising a reactive leaving group capable of reacting with a thiourea to form a isothiouronium group, thereby forming an initial polyurethane comprising pendent leaving groups (e.g., halide groups such as bromide, chloride, and/or iodide). Treating the initial polyurethane with thiourea furnishes a cationic polyurethane comprising pendent isothiouronium groups.

The cationic polyurethane can be a random copolymer comprising a non-charged second urethane-containing repeat unit. Preferably, the second urethane-containing repeat unit contains a divalent poly(ethylene oxide) moiety that is a portion of the cationic polyurethane backbone. More specific second urethane-containing repeat units have a structure according to formula (U-3):

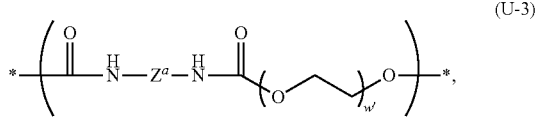

wherein w' is integer having an average value of 1 to 100, and $Z^a$ is a divalent hydrocarbon radical comprising 2 to 20 carbons.

In an embodiment, w' has an average value of 10 to 50. Preferably, $Z^a$ is an alkylene group (e.g., hexane-1,6-diyl (*—CH$_2$CH$_2$CH$_2$CH$_2$CH$_2$CH$_2$—*)).

The cationic polyurethane random copolymers can be prepared by including a poly(ethylene glycol) (PEG) in the reaction mixture used to prepare the initial polyurethane in an amount of 1 mol % to 30 mol %, more specifically 10 mol % to 30 mol %, based on total moles of diol used to prepare the cationic polyurethane, wherein a mole of PEG is based on number average molecular weight of the PEG.

The cationic polyurethanes and/or the initial polyurethanes preferably have a number average molecular weight (Mn) of at least 1500 g/mol, more specifically 1500 g/mol to 1,000,000 g/mol, 4000 g/mol to 150000 g/mol, or 4000 g/mol to 50000 g/mol. In an embodiment, the cationic polyurethanes and/or the initial polyurethanes have a number average molecular weight of 4,000 to 15,000 g/mole. The cationic polyurethanes and/or the initial polyurethanes can have a polydispersity index generally from 1.01 to 3.0, more particularly 1.01 to 2.0, and even more particularly 1.01 to 1.5.

Antimicrobial Hydrogels

Also disclosed are antimicrobial hydrogels comprising water, 0.1 wt % to 5 wt % of an above-described cationic polymer comprising a guanidinium and/or isothiouronium pendent group and 5 wt % to 15 wt % of a non-charged amphiphilic ABA triblock copolymer.

The ABA triblock copolymer preferably comprises a central B block comprising a poly(ethylene oxide) chain segment (PEG block) linked at each end to respective hydrophobic A blocks comprising a polycarbonate and/or polyester chain segments. Each of the A blocks preferably has a degree of polymerization (DP) of 5 to 20, more specifically 5 to 10, and the B block (PEG block) has a DP of 100 to 1000. Triblock copolymer TPB-1 described in the examples further below exemplifies this type of polymer.

Preferred antimicrobial cationic polymers for the hydrogel are 2-armed block copolymers represented by the formula AB-C'-AB, wherein each AB block copolymer arm AB comprises a peripheral A block linked to an inner B block, which is linked to a central divalent core C'. The inner B block comprises a cationic repeat unit comprising a pendent guanidinium and/or isothiouronium group. The A block comprises a hydrophobic repeat unit. The core is preferably a dioxy residue of a diol initiator used to form the 2 armed block copolymer by ring opening polymerization. Each A block can have a DP of 5 to 20, more preferably 5 to 10. Each B block can have a DP of 10 to 100, more preferably 10 to 50.

Surface-Modified Particles

Also disclosed are antimicrobial particles comprising a core and a plurality of independent antimicrobial surface groups comprising one or more guanidinium and/or an isothiouronium groups. The surface groups can be a polymer chain or non-polymer moiety comprising any of the above-described cationic subunits. The surface groups are covalently linked to the core by way of any suitable linking group L". The core can comprise an inorganic material (e.g., silica, silica gel), organometallic material, organic material (e.g., dendrimer), or mixture thereof. One or more of the surface groups linked to the core can comprise one or more carbonate and/or carbamate repeat units comprising a pendent guanidinium and/or an isothiouronium group. In an embodiment, the particles comprise a plurality of surface groups comprising a comprising a cationic subunit of formula (A-2) and/or formula (A-4). In this instance, atoms labeled 1-6 of formula (A-2) and formula (A-4) are backbone atoms of the surface groups.

In addition to being effective antimicrobial agents, surface modified particles comprising isothiouronium surface groups can, in some instances, effectively sequester metal ions from aqueous solution, making them attractive for water purification systems. In an embodiment, the surface modified particles are capable of removing mercury and palladium ions from aqueous solution. More specifically, the surface modified particles are capable of sequestering Hg(II) and Pd(II) from aqueous solution.

Antimicrobial Properties

For the examples further below, the following definitions are applicable.

HC50 is defined as the concentration (in mg/L) of a substance (e.g., cationic polymer, loaded complex containing cationic polymer and a drug, etc.) that causes 50% of mammalian red blood cells to undergo hemolysis. HC50 values of 1000 mg/L or higher are desirable.

HC20 is defined as the concentration (in mg/L) of a substance that causes 20% of mammalian red blood cells to undergo hemolysis. HC20 values of 500 mg/L or higher are desirable.

Half-maximal inhibitory concentration (IC50) is defined as the concentration of a substance for which a given biological response is reduced by half.

Minimum inhibitory concentration (MIC) is defined as the minimum concentration (in mg/L) of a substance required to inhibit growth of a given microbe for an 18 hour period (bacteria) or 42 hour period (fungi). A MIC less than 500 mg/L is desirable. Even more desirable is a MIC of 150 mg/L or less. A lower MIC indicates higher antimicrobial activity.

Minimum bactericidal concentration (MBC) is defined as the minimum concentration (in mg/L) of a substance required to kill a given microbe. A lower MBC indicates higher antimicrobial activity.

HC50 selectivity is defined as the ratio of HC50/MIC. An HC50 selectivity of 3 or more is desirable. Higher HC50 selectivity values indicate more activity against bacterial cells and less toxicity to mammalian cells. Likewise, HC20 selectivity is defined as the ratio of HC20/MIC. An HC20 selectivity of 3 or more is desirable.

Non-limiting exemplary bacteria include Gram-positive *Staphylococcus aureus* (*S. aureus*), Gram-negative *Escherichia coli* (*E. coli*), fungus *Candida albicans* (*C. albicans*), Gram-negative *Pseudomonas aeruginosa* (*P. aeruginosa*), and yeasts. Other microbes include Gram-positive *Staphylococcus epidermidis* (*S. epidermidis*), Gram-positive Methicillin-resistant *Staphylococcus aureus* (MRSA), Gram-positive Vancomycin-resistant *Enterococcus* (VRE), Gram-negative *Acinetobacter baumannii* (*A. baumannii*), and Gram-negative *Klebsiella pneumoniae* (*K. pneumoniae*) and *Cryptococcus neoformans* (*C. neoformans*).

The cationic polymers and/or the cationic polymer-modified particles can have a minimum inhibitory concentration (MIC) of 4 mg/L to 500 mg/L, and more preferably 5 mg/L to 250 mg/L, and most preferably 5 mg/L to 125 mg/L against a bacterium. In an embodiment, the cationic polymers have a MIC of 15 mg/L to 62 mg/L against *P. aeruginosa*.

The geometric mean of the MICs for the four microbes tested below is represented by Gm. Gm can have a value of 10 to 500, more particularly 10 to 100.

The cationic polymers are generally non-hemolytic, having HC50 values of >1000 mg/L, more particularly >8000 mg/L.

The cationic polymers preferably have an HC50 selectivity value (HC50/Gm) greater than 4, more preferably greater than 100.

INDUSTRIAL APPLICABILITY

The cationic polymers have utility as antimicrobial components of consumer products that are used in contact with skin such as, for example, cosmetics (e.g., skin lotions, skin creams, topically applied powders, mascara, eye liners, lip glosses), soaps, shampoos, and deodorants. The cationic polyamines also have utility as antimicrobial components of laundry detergents.

The cationic polyamines can also have utility for human and/or non-human therapeutic medical treatments. The cationic polymers can be used as stand-alone antibiotic drugs and/or as a complex comprising the cationic polymer and an anionic form of a biologically active material (e.g., genes, drugs) bound by non-covalent interactions. A medical composition comprising a cationic polymer and/or a biologically active material selected from the group consisting of genes, drugs, and combinations thereof, can be administered topically, intravenously, orally, by way of other body cavities, and/or by inhalant. The medical composition can have the form of a powder, a pill, a liquid, a paste, or a gel. The medical compositions can be used in injectable systems for delivery of rigid, hydrophobic biologically active materials that have low water solubility, such as the drugs paclitaxel and doxorubicin.

A method comprises contacting a microbe with a cationic polymer, thereby killing the microbe.

Another method comprises contacting a tumor cell with a complex comprising a disclosed cationic polymer and a tumor-treating drug, thereby killing the tumor cell.

An antimicrobial composition comprises a disclosed cationic polymer and at least one other component (e.g., water, drug, gene). The antimicrobial composition can be applied to a human and/or non-human animal tissue, including mammalian and/or non-mammalian animal tissue. The general term "animal tissue" includes wound tissue, burn tissue, skin, internal organ tissue, blood, bones, cartilage, teeth, hair, eyes, nasal surfaces, oral surfaces, other body cavity surfaces, and any cell membrane surfaces. In an embodiment, a method comprises contacting an animal tissue with the antimicrobial composition, thereby inhibiting, preventing, and/or eradicating a microbial infection of the tissue.

Other uses of the cationic polymers include disinfectant washes for hands, skin, hair, bone, ear, eye, nose, throat, internal tissue, wounds, and teeth (e.g., as a mouthwash).

Still other uses of the cationic polymers include disinfectants for articles such as medical devices. Medical devices include swabs, catheters, sutures, stents, bedpans, gloves, facial masks, absorbent pads, absorbent garments, internal absorbent devices, and insertable mechanical devices. In an embodiment, a method comprises contacting a medical device with an antimicrobial composition comprising a disclosed cationic polymer, thereby disinfecting the medical device. In an embodiment, the medical device is a catheter.

The antimicrobial compositions are also attractive as disinfecting agents for other surfaces such as, for example, building surfaces in homes, businesses, and particularly hospitals that come into contact with body tissues and/or fluids. Exemplary home and commercial building surfaces include floors, door surfaces, bed surfaces, air conditioning surfaces, bathroom surfaces, railing surfaces, kitchen surfaces, wall surfaces, and non-medical equipment surfaces. Surfaces of articles can comprise materials such as wood, paper, metal, cloth, plastic, rubber, glass, paint, leather, or combinations thereof. In an embodiment, a method comprises contacting a surface of an article with an antimicrobial composition comprising a disclosed cationic polymer, thereby disinfecting the surface. In another embodiment, the antimicrobial composition has the form of a solution.

In an embodiment, the antimicrobial composition is selected from the group consisting of soaps, shampoos, skin lotions, skin creams, cosmetics, mouthwashes, wound care agents, deodorants, surface cleaning agents, and laundry detergents.

Cationic Polymer Complexes

In water, optionally containing organic solvent, the cationic polymers can form a nanoparticulate complex with an anionic biologically active cargo material, bound by non-covalent interactions. The cationic polymer complex can have the form of a loaded micelle comprising a plurality of self-assembled macromolecules of the cationic polymer and one or more molecules of the cargo material.

A method of forming a nanoparticulate cationic polymer complex comprises i) forming a first solution comprising a cationic polymer (i.e., carrier) and water; ii) forming a second solution comprising a biologically active material (i.e., anionic form of a gene and/or a drug) in water and/or a water miscible organic solvent; iii) combining the first and seconds solutions; and iv) removing any organic solvent (e.g., by dialysis), thereby forming an aqueous mixture comprising the complex. The complex can comprise the cationic polymer in an amount of 85.0 wt. % to 99.9 wt. %, and the biologically active material in an amount of 15.0 wt. % to 0.1 wt. %, each based on total dry weight of the complex.

The term "loading efficiency" refers to the percentage of the initial weight of the biologically active material that is incorporated into the cationic polymer complex. The loading efficiency of the biologically active material in the cationic polymer complex is preferably at least 10%. Generally, the loading efficiency of the biologically active material is in a range of 10% to 50%, and even more specifically in a range of 30% to 50%.

Nanoparticles of the cationic polymer complex can have an average particle size (circular cross sectional diameter) of 10 nm to 500 nm, 10 nm to 250 nm, and preferably 25 nm to 200 nm as measured by dynamic light scattering. For the foregoing particle sizes, the aqueous solution can have a pH of 4.5 to 8.0, 5.0 to 7.0, or 6.0 to 7.0.

The organic solvent, if any, used to prepare the cationic polymer complex is preferably miscible with water at concentrations of at least 1 microliter or more of organic solvent per 100 microliters of water. Exemplary organic solvents include methanol, ethanol, propanol, 2-propanol, 1-butanol, 2-butanol, t-butyl alcohol, acetone, 2-butanone, dimethoxyethane, diglyme, diethyl ether, methyl t-butyl ether, methylene chloride, ethyl acetate, ethylene glycol, glycerin, dimethylsulfoxide, dimethylformamide, acetic acid, tetrahydrofuran (THF), and dioxane.

As stated above, the biologically active cargo material can be a drug. Exemplary commercially available drugs include the following, where the generic drug is enclosed in parentheses: 13-cis-Retinoic Acid, 2-CdA (Cladribine), 2-Chlorodeoxyadenosine (Cladribine), 5-Azacitidine, 5-Fluorouracil (Fluorouracil), 5-FU (Fluorouracil), 6-Mercaptopurine, 6-MP (6-Mercaptopurine), 6-TG (Thioguanine), 6-Thioguanine (Thioguanine), ABRAXANE® (Paclitaxel protein bound), ACCUTANE® (Isotretinoin), Actinomycin-D (Dactinomycin), ADRIAMYCIN® (Doxorubicin), ADRUCIL® (Fluorouracil), AFINITOR® (Everolimus), AGRYLIN® (Anagrelide), ALA-CORT® (Hydrocortisone), Aldesleukin, Alemtuzumab, ALIMTA® (Pemetrexed), Alitretinoin (9-cis-retinoic acid), Alkaban-AQ (Vinblastine), ALKERAN® (Melphalan), All-transretinoic Acid (Tretinoin), Alpha Interferon (Interferon Alfa), Altretamine, Amethopterin (Methotrexate), Amifostine, Aminoglutethimide, Anagrelide, ANANDRON® (Nilutamide), Anastrozole, Arabinosylcytosine (Cytarabine), Ara-C (Cytarabine), ARANESP® (Darbepoetin Alfa), AREDIA® (Pamidronate), ARIMIDEX® (Anastrozole), AROMASIN® (Exemestane), ARRANON® (Nelarabine), Arsenic Trioxide, Asparaginase, ATRA (All-transretinoic Acid), AVASTIN® (Bevacizumab), Azacitidine, BCG, BCNU (Carmustine), Bendamustine (Bendamustine Hydrochloride), Bevacizumab, Bexarotene, BEXXAR® (Tositumomab), Bicalutamide, BICNU® (Carmustine), BLENOXANE® (Bleomycin), Bleomycin, Bortezomib, Busulfan, BUSULFEX® (Busulfan), C225 (Cetuximab), Calcium Leucovorin (Leucovorin), CAMPATH® (Alemtuzumab), CAMPTOSAR® (Irinotecan), Camptothecin-11 (Irinotecan), Capecitabine, CARAC® (Fluorouracil), Carboplatin, Carmustine, Carmustine Wafer, CASODEX® (Bicalutamide), CC-5013 (Lenalidomide), CCI-779 (Temsirolimus), CCNU (Lomustine), CDDP (Cisplatin), CEENU® (Lomustine), CERUBIDINE® (Daunomycin), Cetuximab, Chlorambucil, Cisplatin, Citrovorum Factor (Leucovorin), Cladribine, Cortisone (Hydrocortisone), COSMOGEN® (Dactinomycin), CPT-11 (Irinotecan), Cyclophosphamide, CYTADREN® (Aminoglutethimide), Cytarabine, Cytarabine Liposomal, CYTOSAR-U® (Cytarabine), CYTOXAN® (Cyclophosphamide), Dacarbazine, DACOGEN® (Decitabine), Dactinomycin, Darbepoetin Alfa, Dasatinib, Daunomycin, Daunorubicin, Daunorubicin Hydrochloride, Daunorubicin Liposomal, DAUNOXOME® (Daunorubicin Liposomal), DECADRON™ (Dexamethasone), Decitabine, DELTA-CORTEF® (Prednisolone), DELTASONE® (Predni sone), Denileukin Diftitox, DEPOCYT® (Cytarabine Liposomal), Dexamethasone, Dexamethasone Acetate, Dexamethasone Sodium Phosphate, DEXASONE® (Dexamethasone), Dexrazoxane, DHAD (Mitoxantrone), DIC (Dacarbazine), DIODEX® (Dexamethasone), Docetaxel, DOXIL® (Doxorubicin Liposomal), Doxorubicin, Doxorubicin Liposomal, DROXIA® (Hydroxyurea), DTIC (Dacarbazine), DTIC-DOME® (Decarbazine), Duralone (Methylprednisolone), EFUDEX® (Fluorouracil), ELIGARD® (Leuprolide), ELLENCE® (Epirubicin), ELOXATIN® (Oxaliplatin), ELSPAR® (Asparaginase), EMCYT® (Estramustine), Epirubicin, Epoetin Alfa, ERBITUX® (Cetuximab), Erlotinib, Erwinia L-asparaginase (Asparaginase), Estramustine, ETHYOL® (Amifostine), ETOPOPHOS® (Etoposide), Etoposide, Etoposide Phosphate, EULEXIN® (Flutamide), Everolimus, EVISTA® (Raloxifene), Exemestane, FARESTON® (Toremifene), FASLODEX® (Fulvestrant), FEMARA® (Letrozole), Filgrastim, Floxuridine, FLUDARA® (Fludarabine), Fludarabine, FLUOROPLE® (Fluorouracil), Fluorouracil, Fluorouracil (cream), Fluoxymesterone, Flutamide, Folinic Acid (Leucovorin), FUDR® (Floxuridine), Fulvestrant, G-CSF (Pegfilgrastim), Gefitinib, Gemcitabine, Gemtuzumab ozogamicin, GEMZAR® (Gemcitabine), GLEEVEC® (Imatinib mesylate), GLIADEL® Wafer (Carmustine Wafer), GM-CSF (Sargramostim), Goserelin, Granulocyte—Colony Stimulating Factor (Pegfilgrastim), Granulocyte Macrophage Colony Stimulating Factor (Sargramostim), HALOTESTIN® (Fluoxymesterone), HERCEPTIN® (Trastuzumab), HEXADROL® (Dexamethasone), HEXALEN® (Altretamine), Hexamethylmelamine (Altretamine), HMM (Altretamine), HYCAMTIN® (Topotecan), HYDREA® (Hydroxyurea), Hydrocort Acetate (Hydrocortisone), Hydrocortisone, Hydrocortisone Sodium Phosphate, Hydrocortisone Sodium Succinate, HYDROCORTONE® Phosphate (Hydrocortisone), Hydroxyurea, Ibritumomab, Ibritumomab Tiuxetan (Ibritumomab), IDAMYCIN® (Idarubicin), Idarubicin, IFEX® (Ifosfamide), IFN-alpha (Interferon alfa), Ifosfamide, IL-11 (Oprelvekin), IL-2 (Aldesleukin), Imatinib mesylate, Imidazole Carboxamide (Decarbazine), Interferon alfa, Interferon Alfa-2b (PEG Conjugate), Interleukin −2 (Aldesleukin), Interleukin-11 (Oprelvekin), INTRON® A (interferon alfa-2b), IRESSA® (Gefitinib), Irinotecan, Isotretinoin, Ixabepilone, IXEMPRA® (Ixabepilone), Kidrolase (Asparaginase), LANACORT® (Hydrocortisone), Lapatinib, L-asparaginase, LCR (Vincristine), Lenalidomide, Letrozole, Leucovorin, LEUKERAN® (Chlorambucil), LEUKINE® (Sargramostim), Leuprolide, Leurocristine (Vincristine), LEUSTATIN® (Cladribine), Liposomal Ara-C, LIQUID PRED® (Prednisone), Lomustine, L-PAM (Melphalen), L-Sarcolysin (Melphalen), LUPRON® (Leuprolide), LUPRON DEPOT® (Leuprolide), MATULANE® (Procarbazine), MAXIDEX® (Dexamethasone), Mechlorethamine, Mechlorethamine Hydrochloride, Medralone (Methylprednisolone), MEDROL (Methylprednisolone), MEGACE® (Megestrol), Megestrol, Megestrol Acetate (Megastrol), Melphalan, Mercaptopurine (6-Mercaptopurine), Mesna, MESNEX® (Mesna), Methotrexate, Methotrexate Sodium (Methotrexate), Methylprednisolone, METICORTEN® (Prednisone), Mitomycin (Mitomycin C), Mitomycin-C, Mitoxantrone, M-Prednisol (Methylprednisolone), MTC (Mitomycin-C), MTX (Methotrexate), MUSTARGEN® (Mechlorethamine), Mustine (Mechlorethamine), MUTAMYCIN® (Mitomycin-C), MYLERAN® (Busulfan), MYLOCEL® (Hydroxyurea), MYLOTARG® (Gemtuzumab ozogamicin), NAVELBINE® (Vinorelbine), Nelarabine, NEOSAR® (Cyclophosphamide), NEULASTA® (Pegfilgrastim), NEUMEGA® (Oprelvekin), NEUPOGEN® (Filgrastim), NEXAVAR® (Sorafenib), NILANDRON® (Nilutamide), Nilutamide, NIPENT® (Pentostatin), Nitrogen Mustard (Mechlorethamine), NOLVADEX® (Tamoxifen), NOVANTRONE® (Mitoxantrone), Octreotide, Octreotide acetate (Octreotide), ONCASPAR® (Pegaspargase), ONCOVIN® (Vincristine), ONTAK® (Denileukin Diftitox), ONXOL® (Paclitaxel), Oprelvekin (Interleukin-11), ORAPRED® (Prednisolone), ORASONE® (Predni sone), Oxaliplatin, Paclitaxel, Paclitaxel Protein-bound, Pamidronate, Panitumumab, PANRETIN® (Alitretinoin), PARAPLATIN® (Carboplatin), PEDIAPRED® (Prednisolone), PEG Interferon, Pegaspargase, Pegfilgrastim, PEG-INTRON® (Interferon Alfa-2b), PEG-L-asparaginase, Pemetrexed, Pentostatin, Phenylalanine Mustard (Melphalen), PLATINOL® (Cisplatin), Platinol-AQ (Cisplatin), Prednisolone, Prednisone, PRELONE® (Prednisolone), Procarbazine, PROCRIT® (Epoetin Alfa), PROLEUKIN® (Aldesleukin), Prolifeprospan 20 with Carmustine Implant (Carmustine Wafer), PURINETHOL® (6-Mercaptopurine), Raloxifene, REVLIMID® (Lenalidomide), RHEUMATREX® (Methotrexate), RITUXAN® (Rituximab), Rituximab, Roferon-A (Interferon Alfa-2a), RUBEX® (Doxorubicin), Rubidomycin hydrochloride (Daunomycin), SANDOSTATIN® (Octreotide), SANDOSTATIN LAR® (Octreotide), Sargramostim, SOLU-CORTEF® (Hydrocortisone), SOLU-MEDROL® (Methylprednisolone), Sorafenib, SPRYCEL® (Dasatinib), STI-571 (Imatinib Mesylate), Streptozocin, SU11248 (Sunitinib), Sunitinib, SUTENT® (Sunitinib), Tamoxifen, TARCEVA® (Erlotinib), TARGRETIN® (Bexarotene), TAXOL® (Paclitaxel), TAXOTERE® (Docetaxel), TEMODAR® (Temozolomide), Temozolomide, Temsirolimus, Teniposide, TESPA (Thiotepa), Thalidomide, THALOMID® (Thalidomide), THERACYS® (BCG), Thioguanine, Thioguanine Tabloid (Thioguanine), Thiophosphoamide (Thiotepa), THIOPLEX® (Thiotepa), Thiotepa, TICE® (BCG), TOPOSAR® (Etoposide), Topotecan, Toremifene, TORISEL® (Temsirolimus), Tositumomab, Trastuzumab, TREANDA® (Bendamustine Hydrochloride), Tretinoin, TREXALL® (Methotrexate), TRISENOX® (Arsenic Trioxide), TSPA (Thiotepa), TYKERB® (Lapatinib), VCR (Vincristine), VECTIBIX® (Panitumumab), VELBAN® (Vinblastine), VELCADE® (Bortezomib), VEPESID® (Etoposide), VESANOID® (Tretinoin), VIADUR® (Leuprolide), VIDAZA® (Azacitidine), Vinblastine, Vinblastine Sulfate, VINCASAR PFS® (Vincristine), Vincristine, Vinorelbine, Vinorelbine tartrate (Vinorelbine), VLB (Vinblastine), VM-26 (Teniposide), Vorinostat, VP-16 (Etoposide), VUMON® (Teniposide), XELODA® (Capecitabine), ZANOSAR® (Streptozocin), ZEVALIN® (Ibritumomab), ZINECARD® (Dexrazoxane), ZOLADEX® (Goserelin), Zoledronic acid, ZOLINZA® (Vorinostat), and ZOMETA® (Zoledronic acid).

The following examples demonstrate the preparation, antimicrobial properties, hemolytic properties, and cytotoxicity of the cationic polymers.

EXAMPLES

Materials used in the following examples are listed in Table 1.

TABLE 1

| ABBREVIATION | DESCRIPTION | SUPPLIER |
|---|---|---|
| APSilica | Aminopropyl-modified silica particles | Sigma-Aldrich |
| BBocTU | 1,3-Bis(tert-butoxycarbonyl)-2-methyl-2-thiopseudourea | Sigma-Aldrich |
| DBU | 1,8-Diazabicyclo[5.4.0]undec-7-ene | Sigma-Aldrich |
| DCM | Dichloromethane | Sigma-Aldrich |
| DIPEA | N,N-diisopropylethylamine | Sigma-Aldrich |
| DMEM | Dulbecco's Modified Eagle Medium | Lonza Singapore |
| FBS | Fetal Bovine Serum | Invitrogen |
| HO-PEG-OH | Poly(ethylene glycol), Mn 20000 | Sigma-Aldrich |
| MeBnOH | 4-Methyl benzyl alcohol MW 122.2 | Sigma-Aldrich |
| MHB | Mueller Hinton Broth | BD Diagnostics, SG |
| MTT | 3-[4,5-Dimenthylthiazol-2-yl]-2,5-diphenyl tetrazolium bromide | Invitrogen |
| PBS | Phosphate Buffered Saline | $1^{st}$ Base, SG |
| TEA | Triethylamine | Sigma-Aldrich |
| TFA | Trifluoroacetic acid | Sigma-Aldrich |
| THF | Tetrahydrofuran | Sigma-Aldrich |
| TSB | Tryptic Soy Broth | BD Diagnostics, SG |
| TU | N-bis(3,5-trifluoromethyl)phenyl-N'-cyclohexylthiourea | Prepared below |

Herein, Mn is the number average molecular weight, Mw is the weight average molecular weight, and MW is the molecular weight of one molecule.

$^1$H-NMR spectra of the monomers and polymers were recorded on a Bruker Advance 400 NMR spectrometer at 400 MHz at ambient temperature. The $^1$H-NMR measurements were carried out with an acquisition time of 3.2 s, a pulse repetition time of 2.0 s, a 30° pulse width, 5208-Hz spectral width, and 32 K data points. Chemical shifts were referenced accordingly to the respective solvent peaks (i.e., δ=7.26 for $CDCl_3$, 2.50 ppm for DMSO-$d_6$ and 3.31 for $CD_3OD$.

Gel permeation chromatography (GPC) was performed in tetrahydrofuran (THF) using a Waters system equipped with four 5-micrometer Waters columns (300 mm×7.7 mm) connected in series with increasing pore size (100, 1000, 105, and 106 angstroms), a Waters 410 differential refractometer, and a 996 photodiode array detector. The system was calibrated using polystyrene standards.

All chemical reagents were purchased from Sigma-Aldrich, U.S.A. and used as received unless otherwise specified. Ultrapure (HPLC grade) water was obtained from J. T. Baker (U.S.A.). Phosphate-buffered saline (PBS) at 10× concentration was purchased from 1st BASE (Singapore) and diluted to the intended concentrations before use. Cation-adjusted Mueller-Hinton broth (MHB) powder was bought from BD Diagnostics (Singapore) and used to prepare the microbial broths according to the manufacturer's instructions. *Staphylococcus aureus* (ATCC No. 6538), *Escherichia coli* (ATCC No. 25922), *Pseudomonas aerugi-* nosa (ATCC No. 9027) and yeast *Candida albicans* (ATCC No. 10231) were obtained from ATCC (U.S.A) and reconstituted according to the suggested protocols. Fetal bovine serum (FBS) was purchased from Invitrogen Corporation. 3-[4,5-Dimenthylthiazol-2-yl]-2,5-diphenyl tetrazolium bromide (MTT) was dissolved in phosphate-buffered saline (PBS, pH 7.4) with a concentration of 5 mg/mL, and the solution was filtered with a 0.22 micron filter to remove blue formazan crystals prior to usage. Rat red blood cells (RBCs) were obtained from the Animal Handling Unit of Biomedical Research Centers (Singapore).

N-bis(3,5-trifluoromethyl)phenyl-N'-cyclohexylthiourea (TU),

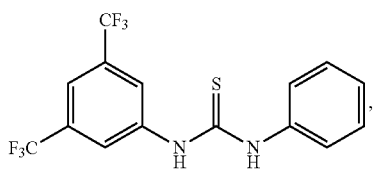 [SMILES: FC(F)(F)c1cc(NC(=S)Nc2ccccc2)cc(C(F)(F)F)c1]

was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over $CaH_2$, filtering, and removing solvent under vacuum.

Prior to use, 1,8-diazabicyclo [5,4,0]undec-7-ene (DBU) was stirred over $CaH_2$ and vacuum distilled before being transferred to a glove box.

The following materials were prepared by the general procedure reported in R. C. Pratt, et al., Chemical Communications, 2008, 114-116:

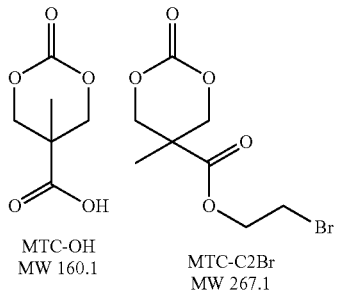

MTC-OH
MW 160.1

MTC-C2Br
MW 267.1

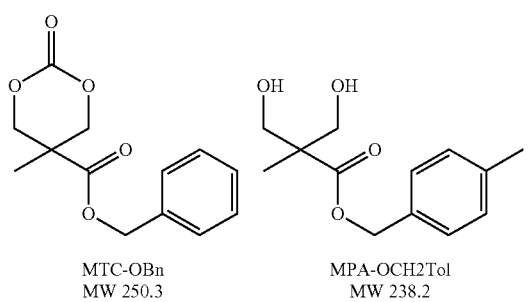

MTC-OBn
MW 250.3

MPA-OCH2Tol
MW 238.2

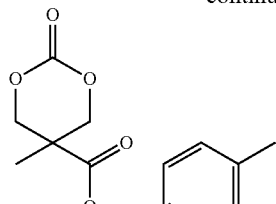

MTC-OCH2Tol
MW 264.3

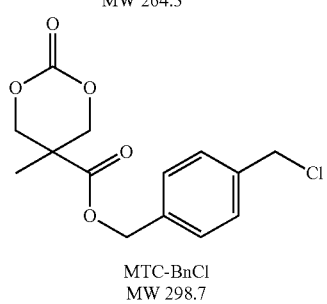

MTC-BnCl
MW 298.7

Diol compound MPA-NHS was prepared by the general procedures reported in Y. Zhou, R.-X. Zhuo, Z.-L. Liu, Macromol. Rapid. Comm., 2005, 26 (16), 1309-1314.

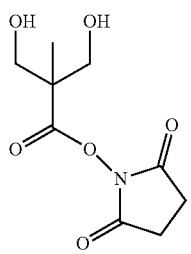

MPA-NHS

Synthesis of Compounds

Example 1

Preparation of Boc-protected guanylated alcohol C2G1.

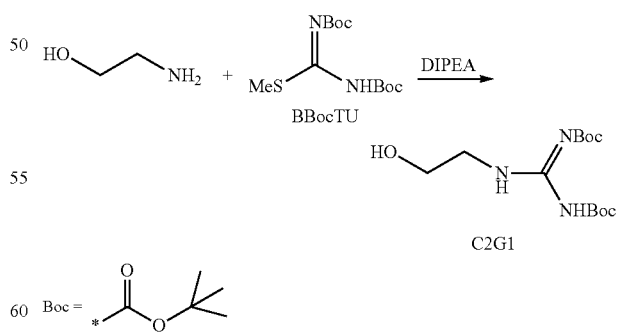

The following procedure is representative. To a solution mixture of ethanolamine (1.37 mL, 22.8 mmol, 2.0 equivalents) and N,N-diisopropylethylamine (DIPEA, 6.0 mL, 34.4 mmol, 3.0 equiv) was added 1,3-bis(tert-butoxycarbonyl)-2-methyl-2-thiopseudourea (BBocTU, 3.3 g, 11.6 mmol, 1.0 equivalents) in dry dichloromethane (DCM, 20 mL), and the mixture was left to stir overnight at room temperature. Upon reaction completion, a constant stream of nitrogen gas was bubbled through the reaction mixture for approximately 1 hour so as to aid in purging of the gaseous by-product, MeSH. After the removal of residual solvent in vacuo, the crude product was purified by flash column chromatography using silica gel and a hexane-ethyl acetate solvent system as the eluent (gradient elution up to 50% vol. ethyl acetate) to yield the Boc-protected guanylated alcohol C2G1 as a white solid (3.2 g, 10.4 mmol, 90% yield). $^1$H-NMR (400 MHz, CDCl$_3$, 22° C.): δ 11.45 (s, 1H, NH), 8.72 (s, 1H, NH), 3.77 (dd, J=5.3, 3.9 Hz, 2H, —CH$_2$—), 3.57 (dd, J=9.2, 5.5 Hz, 2H, —CH$_2$—), 1.49 (d, J=8.2 Hz, 18H, Boc —CH$_3$).

Example 2

Preparation of Boc-protected guanylated alcohol C3G1.

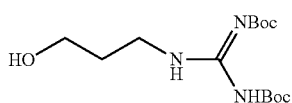

C3G1

C3G1 was prepared by the procedure of Example 1 using 3-amino-1-propanol. Yield: 87%; $^1$H-NMR (400 MHz, CDCl$_3$, 22° C.): δ 11.44 (s, 1H, NH), 8.47 (s, 1H, NH), 3.57 (dt, J=12.1, 5.8 Hz, 4H, —CH$_2$—), 1.72-1.66 (m, 2H, —CH$_2$—), 1.48 (d, J=9.9 Hz, 18H, Boc —CH$_3$).

Example 3

Preparation of Boc-protected guanylated alcohol C4G1.

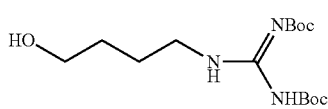

C4G1

C4G1 was prepared by the procedure of Example 1 using 4-amino-1-butanol. Yield: 90%; $^1$H-NMR (400 MHz, CDCl$_3$, 22° C.): δ 11.48 (s, 1H, NH), 8.39 (s, 1H, NH), 3.69 (t, J=6.1 Hz, 2H, —CH$_2$—), 3.49-3.41 (m, 2H, —CH$_2$—), 1.71-1.59 (m, 4H, —CH$_2$—), 1.49 (d, J=2.3 Hz, 18H, Boc —CH$_3$).

Example 4

Preparation of Boc-protected guanylated alcohol C5G1.

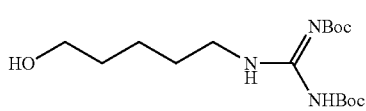

C5G1

C5G1 was prepared by the procedure of Example 1 using 5-amino-1-pentanol. Yield: 89%; $^1$H-NMR (400 MHz, CDCl$_3$, 22° C.): δ 11.49 (s, 1H, NH), 8.31 (s, 1H, NH), 3.64 (t, J=6.5 Hz, 2H, —CH$_2$—), 3.42 (td, J=7.2, 5.4 Hz, 2H, —CH$_2$—), 1.64-1.56 (m, 4H, —CH$_2$—), 1.49 (d, J=3.6 Hz, 18H, Boc —CH$_3$), 1.43 (ddd, J=12.4, 5.7, 3.0 Hz, 2H, —CH$_2$—).

Example 5

Preparation of Boc-protected guanylated alcohol C6G1.

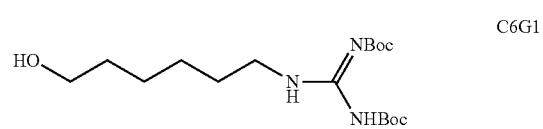

C6G1

C6G1 was prepared by the procedure of Example 1 using 5-amino-1-hexanol. Yield: 81%; $^1$H NMR (400 MHz, CDCl$_3$, 22° C.): δ 11.51 (s, 1H, NH), 8.34 (s, 1H, NH), 3.65 (t, J=6.5 Hz, 2H, —OCH$_2$—), 3.47-3.39 (m, 2H, —CH$_2$N—), 1.61-1.55 (m, 4H, —CH$_2$—), 1.51 (d, J=3.9 Hz, 18H, Boc —CH$_3$), 1.43-1.37 (m, 4H, —CH$_2$—).

Example 6

Preparation of Boc-protected guanylated alcohol iPrG1.

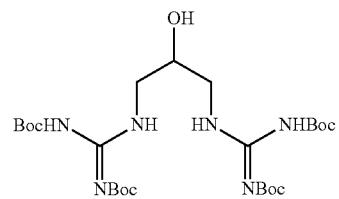

iPrG1

Compound iPrG1 was prepared by the procedure of Example 1 using 1,3-diamino-2-propanol and two equivalents of BBocTU. Yield: 87%; $^1$-H-NMIR (400 MHz, CDCl$_3$, 22° C.): δ 11.45 (s, 2H, NH), 8.72 (s, 2H, NH), 3.90 (dt, J=9.6, 3.3 Hz, 1H, —CH), 3.66 (dd, J=13.1, 3.4 Hz, 2H, —CH$_2$—), 3.42 (ddd, J=13.8, 6.6, 5.1 Hz, 2H, —CH$_2$—), 1.49 (d, J=3.8 Hz, 36H, Boc —CH$_3$).

Example 7

Preparation of Boc-protected guanylated alcohol CyG1.

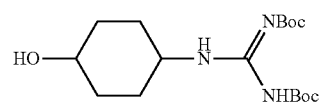

CyG1

CyG1 was prepared by the procedure of Example 1 using 4-amino-1-cyclohexanol. Yield: 82%; $^1$H-NMR (400 MHz, CDCl$_3$, 22° C.): δ 11.53 (s, 1H, NH), 8.24 (s, 1H, NH), 4.08-3.95 (m, 1H, —CH), 3.70-3.59 (m, 1H, —CH), 2.12-2.04 (m, 2H, —CH$_2$—), 2.00-1.91 (m, 2H, —CH$_2$—), 1.49 (d, J=7.7 Hz, 18H, Boc —CH$_3$), 1.45-1.38 (m, 2H, —CH$_2$—), 1.32-1.22 (m, 2H, —CH$_2$—).

Example 8

Preparation of Boc-protected guanylated alcohol PhG1.

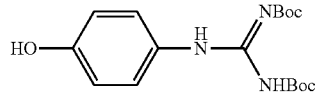

PhG1

PhG1 was prepared by the procedure of Example 1 using 4-amino-phenol. Yield: 72%; [1]-NMR (400 MHz, CDCl$_3$, 22° C.): δ 11.62 (s, 1H, NH), 9.95 (s, 1H, NH), 7.08-7.02 (m, 2H, Ph —CH), 6.63-6.53 (m, 2H, Ph —CH), 1.49 (d, J=34.8 Hz, 18H, Boc —CH$_3$).

Example 9

Preparation of Boc-protected guanylated alcohol BnG1.

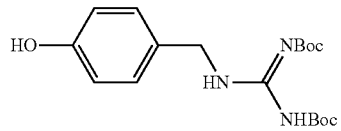

BnG1

BnG1 was prepared by the procedure of Example 1 using 4-hydroxybenzyl amine. Yield: 85%; [1]-H-NMR (400 MHz, CDCl$_3$, 22° C.): δ 11.53 (s, 1H, NH), 8.53 (s, 1H, NH), 7.19-7.09 (m, 2H, Ph —CH), 6.84-6.73 (m, 2H, Ph —CH), 4.52 (d, J=5.1 Hz, 2H, —CH$_2$—), 1.49 (d, J=12.4 Hz, 18H, Boc —CH$_3$).

Example 10

Preparation of MTC-C2G1 monomer.

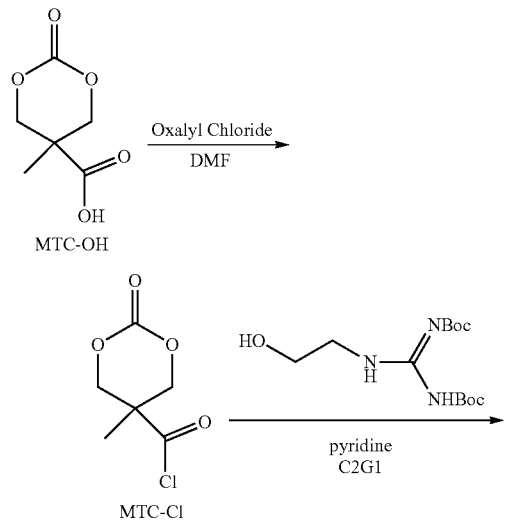

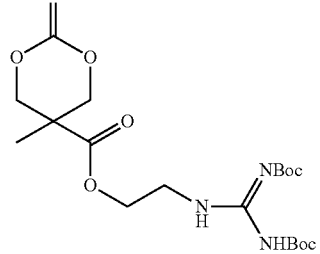

MTC-C2G1

The following procedure is representative. In a dry three-neck round bottom flask equipped with a stir bar, MTC-OH (3.08 g, 19.3 mmol) was dissolved in dry THF (50 mL) with a 3-4 drops of dimethylformamide (DMF). A solution of oxalyl chloride (2.45 mL, 28.5 mmol) in THF (50 mL) was subsequently added from a dropping funnel. Under an inert atmosphere, the solution was stirred for 1 hour, after which volatiles were removed under vacuum, yielding an off-white solid (i.e., 5-chlorocarboxy-5-methyl-1,3-dioxan-2-one intermediate, MTC-C1). The solid was heated to 60° C. for a brief 2-3 min to remove any residual solvent, and then re-dissolved in dry DCM (50 mL) and cooled down to 0° C. via an ice bath. A mixture of the C2G1 (5.4 g, 17.8 mmol) and pyridine (1.55 mL, 19.3 mmol) dissolved in dry DCM (50 mL) was then added dropwise over a duration of 30 minutes, and allowed to stir at 0° C. for an additional 30 min before leaving it at ambient temperature for further stirring overnight. After removal of solvent, the crude product was subjected to purification by flash column chromatography using silica gel and a hexane-ethyl acetate solvent system as the eluent (gradient elution up to 80% vol. ethyl acetate) to yield MTC-C2G1 as a white solid. Yield: 78%; [1]-H-NMR (400 MHz, CDCl$_3$, 22° C.): δ 11.48 (s, 1H, NH), 8.64 (s, 1H, NH), 4.71 (d, J=10.9 Hz, 2H, CH$_a$H$_b$), 4.33 (t, J=5.2 Hz, 2H, —OCH$_2$—), 4.22 (d, J=10.9 Hz, 2H, CH$_a$H$_b$), 3.77 (d, J=5.1 Hz, 2H, —CH$_2$N—), 1.49 (d, J=1.8 Hz, 18H, Boc —CH$_3$), 1.39 (d, J=3.4 Hz, 3H, —CH$_3$).

Example 11

Preparation of MTC-C3G1 monomer.

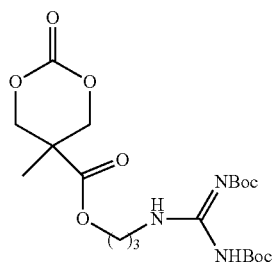

MTC-C3G1

MTC-C3G1 was prepared by the procedure of Example 10 using C3G1. Yield: 75%; [1]-H-NMR (400 MHz, CDCl$_3$, 22° C.): δ 11.50 (s, 1H, NH), 8.40 (s, 1H, NH), 4.72 (d, J=10.9 Hz, 2H, CH$_a$H$_b$), 4.26 (t, J=6.1 Hz, 2H, —OCH2—), 4.21 (d, J=10.9 Hz, 2H, CH$_a$H$_b$), 3.53 (dd, J=12.5, 6.7 Hz, 2H, —CH$_2$N—), 1.99-1.91 (m, 2H, —CH$_2$—), 1.49 (d, J=1.7 Hz, 18H, Boc —CH$_3$), 1.37 (s, 3H, —CH$_3$).

Example 12

Preparation of MTC-C4G1 monomer.

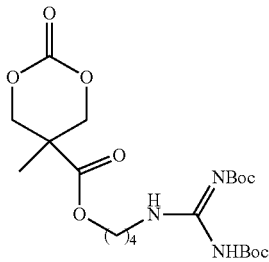

MTC-C4G1

MTC-C4G1 was prepared by the procedure of Example 10 using C4G1. Yield: 75%; $^1$-NMR (400 MHz, CDCl$_3$, 22° C.): δ 11.44 (s, 1H, NH), 8.30 (t, J=4.6 Hz, 1H, NH), 4.64 (d, J=10.8 Hz, 2H, CH$_a$H$_b$), 4.20-4.14 (m, 4H, CH$_a$H$_b$ and —OCH2—), 3.40 (dd, J=12.4, 6.9 Hz, 2H, —CH$_2$N—), 1.68 (dd, J=5.3, 3.0 Hz, 2H, —CH$_2$—), 1.63-1.57 (m, 2H, —CH$_2$—), 1.44 (s, 18H, Boc —CH$_3$), 1.28 (s, 3H, —CH$_3$).

Example 13

Preparation of MTC-C5G1 monomer.

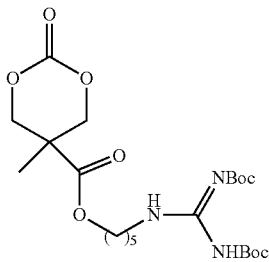

MTC-C5G1

MTC-C4G1 was prepared by the procedure of Example 10 using C5G1. Yield: 79%; $^1$H-NMR (400 MHz, CDCl$_3$, 22° C.): δ 11.50 (s, 1H, NH), 8.33 (s, 1H, NH), 4.68 (d, J=10.8 Hz, 2H, CH$_a$H$_b$), 4.20 (m, J=11.4, 4.5 Hz, 4H, CH$_a$H$_b$ and —OCH2—), 3.43 (dd, J=12.5, 6.8 Hz, 2H, —CH$_2$N—), 1.70 (dd, J=14.8, 7.0 Hz, 2H, —CH$_2$—), 1.63-1.58 (m, 2H, —CH$_2$—), 1.50 (d, J=3.6 Hz, 18H, Boc —CH$_3$), 1.46-1.38 (m, 2H, —CH$_2$—), 1.34 (s, 3H, —CH$_3$).

Example 14

Preparation of MTC-C6G1 monomer.

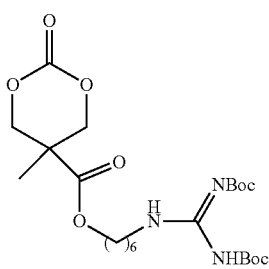

MTC-C6G1

MTC-C6G1 was prepared by the procedure of Example 10 using C5G1. Yield: 72%; $^1$H NMR (400 MHz, CDCl$_3$, 22° C.): δ 11.51 (s, 1H, NH), 8.34 (s, 1H, NH), 4.70 (d, J=10.9 Hz, 2H, CH$_a$H$_b$), 4.10-4.34 (m, 4H, CH$_a$H$_b$ and —OCH2—), 3.42 (m, 2H, —CH$_2$N—), 1.60-1.55 (m, 4H, —CH$_2$—), 1.51 (d, J=3.9 Hz, 18H, Boc —CH$_3$), 1.42-1.36 (m, 4H, —CH$_2$—), 1.33 (s, 3H, —CH$_3$). This monomer was unable to polymerize as it aggregated while polymerizing.

Example 15

Preparation of MTC-iPrG1 monomer.

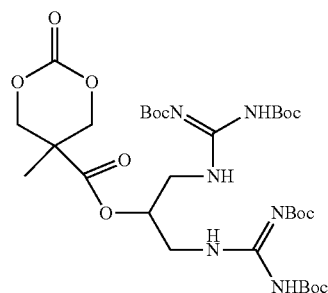

MTC-iPrG1

MTC-iPrG1 was prepared by the procedure of Example 10 using iPrG1. Yield: 80%; $^1$H-NMR (400 MHz, CDCl$_3$, 22° C.): δ 11.46 (s, 2H, NH), 8.57 (s, 2H, NH), 5.21 (tt, J=7.2, 3.6 Hz, 1H, —CH), 4.69 (d, J=11.0 Hz, 2H, CH$_a$H$_b$), 4.23 (d, J=10.9 Hz, 2H, CH$_a$H$_b$), 3.98-3.89 (m, 2H, —CH$_2$—), 3.60-3.49 (m, 2H, —CH$_2$—), 1.49 (d, J=1.4 Hz, 36H, Boc —CH$_3$), 1.45 (s, 3H, —CH$_3$).

Example 16

Preparation of MTC-CyG1 monomer.

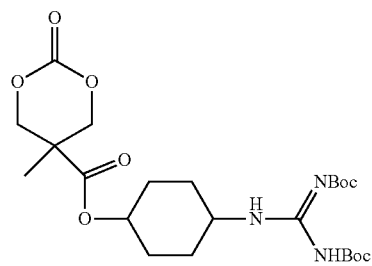

MTC-CyG1

MTC-CyG1 was prepared by the procedure of Example 10 using CyG1. Yield: 60%; $^1$H-NMR (400 MHz, CDCl$_3$, 22° C.): δ 11.50 (s, 1H, NH), 8.31 (s, 1H, NH), 4.88-4.77 (m, 1H, —CH), 4.67 (d, J=10.8 Hz, 2H, CH$_a$H$_b$), 4.18 (d, J=10.8 Hz, 2H, CH$_a$H$_b$), 4.14-4.01 (m, 1H, —CH), 2.09 (dd, J=13.2, 3.3 Hz, 2H, —CH$_2$—), 2.01-1.94 (m, 2H, —CH$_2$—), 1.62-1.56 (m, 2H, —CH$_2$—), 1.49 (d, J=6.0 Hz, 18H, Boc —CH$_3$), 1.42-1.32 (m, 2H, —CH$_2$—), 1.31 (s, 3H, —CH$_3$).

Example 17

Preparation of MTC-PhG1 monomer.

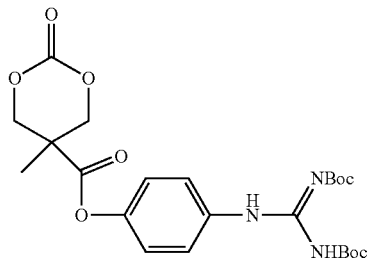

MTC-PhG1

MTC-PhG1 was prepared by the procedure of Example 10 using PhG1. Yield: 75%; $^1$H-NMR (400 MHz, CDCl$_3$, 22° C.): δ 11.62 (s, 1H, NH), 10.40 (s, 1H, NH), 7.65 (d, J=9.0 Hz, 2H, Ph —CH), 7.05 (d, J=9.0 Hz, 2H, Ph —CH), 4.84 (d, J=11.0 Hz, 2H, CH$_a$H$_b$), 4.31 (d, J=10.9 Hz, 2H, CH$_a$H$_b$), 1.52 (d, J=14.3 Hz, 21H, Boc —CH$_3$ and —CH$_3$).

Example 18

Preparation of MTC-BnG1 monomer.

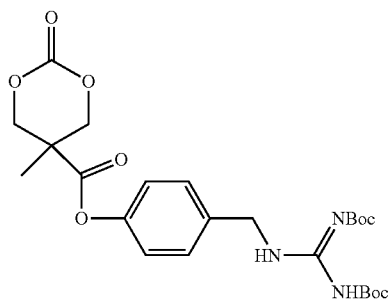

MTC-BnG1

MTC-BnG1 was prepared by the procedure of Example 10 using BnG1. Yield: 78%; $^1$H-NMR (400 MHz, CDCl$_3$, 22° C.): δ 11.53 (s, 1H, NH), 8.67 (s, 1H, NH), 7.35 (dd, J=6.6, 4.7 Hz, 2H, Ph —CH), 7.10-7.04 (m, 2H, Ph —CH), 4.84 (d, J=11.0 Hz, 2H, CH$_a$H$_b$), 4.66 (d, J=5.2 Hz, 2H, —CH$_2$—), 4.32 (d, J=10.9 Hz, 2H, CH$_a$H$_b$), 1.53-1.47 (m, 21H, Boc —CH$_3$ and —CH$_3$).

Polymerizations

Example 19

Cationic homopolymer PC2G-20, x=20, was prepared in two steps.

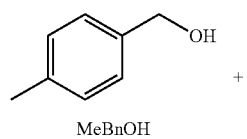

MeBnOH

+

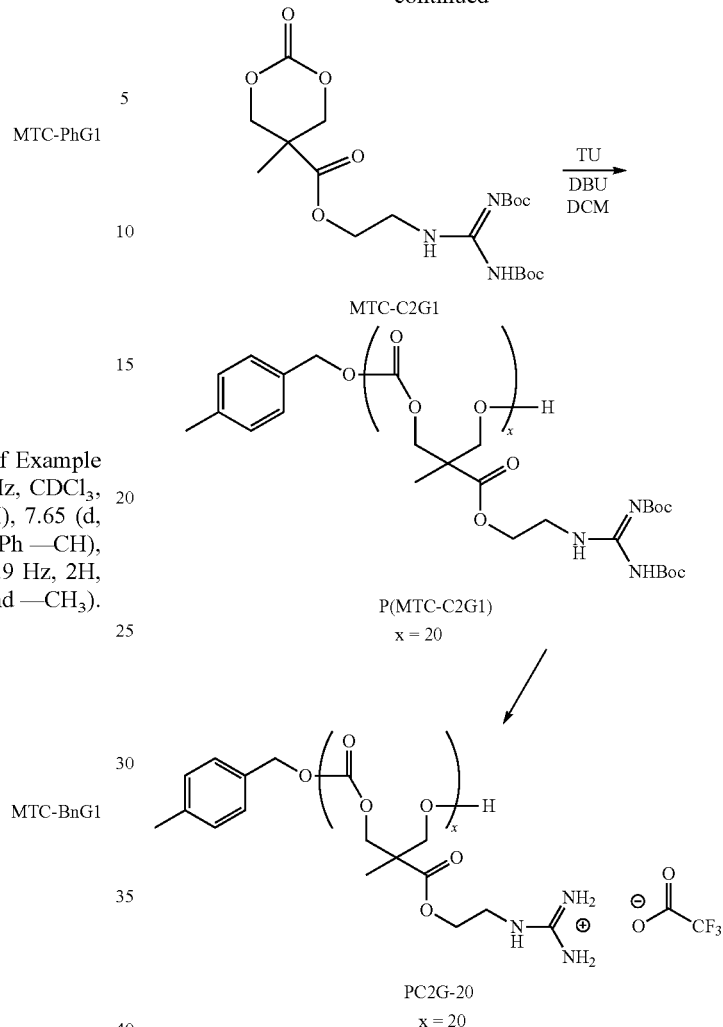

The following procedure is representative. Using a glove box, 4-methyl benzyl alcohol (MeBnOH, 6.1 mg, 0.05 mmol, ROP initiator) was added to a reaction vial containing 1-(3,5-bis(trifluoromethyl)-phenyl)-3-cyclohexyl-2-thiourea (TU, 18.5 mg, 0.05 mmol) and 1,8-diazabicyclo[5.4.0]undec-7-ene (DBU, 7.47 microliters, 0.05 mmol) dissolved in dry DCM (1 mL) and the contents were stirred for about 10 minutes. The mixture was subsequently charged with MTC-C2G1 (445 mg, 1.0 mmol) and left to stir at room temperature for an additional 30 minutes. At the end of the reaction, an excess of benzoic acid (10 mg, 0.08 mmol) was added to quench the catalyst. The crude polymer was isolated and purified via preparative size-exclusion chromatography using THF as the eluent. Upon removal of the solvent in vacuo, a transparent white solid was obtained as the product, P(MTC-C2G1). Yield: 79%; $^1$H-NMR (400 MHz, CDC$_3$, 22° C.): δ 11.47 (s, 22H, NH), 8.61 (bs, 22H, NH), 4.41-4.20 (m, 129H, CH$_a$H$_b$, CH$_a$H$_b$ and —OCH$_2$—), 3.79-3.65 (m, —CH$_2$N—, overlapped with residual THF peak), 2.34 (s, 3H, initiator —CH$_3$), 1.47 (d, J=14.3, 427H, Boc —CH$_3$), 1.24 (bs, 69H, —CH$_3$).

Deprotection of intermediate homopolymer P(MTC-C2G1). The following procedure is representative. P(MTC-C2G1) (150 mg) was dissolved in DCM (9 mL) and trifluoroacetic acid (TFA, 1 mL). The reaction mixture was sealed and stirred at room temperature for 14-18 hours. After the removal of solvent in vacuo, slightly yellow waxy solid was obtained as the deprotected guaninidium-functionalized oligocarbonates in quantitative yields. The polymer was subsequently dissolved in water and lyophilized to yield a white transparent solid. Complete deprotection was ascertained by $^1$H-NMR analysis. Yield: 87%; $^1$H-NMIR (400 MHz, CD$_3$OD, 22° C.): δ 4.33 (s, 83H, CH$_a$H$_b$ and CH$_a$H$_b$), 4.25 (m, 43H, —OCH$_2$—), 3.56-3.48 (m, 45H, —CH$_2$N—), 1.24 (bs, J=30.2 Hz, 69H, —CH$_3$).

Example 20

Preparation of cationic homopolymer PC2G-5, x=5. The above general procedure of Example 19 was used to prepare PC2G-5 having DP=5.

Example 21

Preparation of cationic homopolymer PC2G-10, x=10. The above general procedure of Example 19 was used to prepare PC2G-10 having DP=10.

Example 22

Preparation of homopolymer PC2G-40, x=40. The above general procedure of Example 19 was used to prepare PC2G-40 having DP=40.

Example 23

Preparation of cationic homopolymer PC3G-20, x=20.

-continued

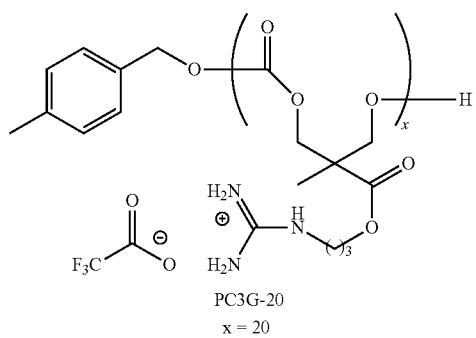

PC3G-20
x = 20

A) Preparation of intermediate homopolymer P(MTC-C3G1), x=20. P(MTC-C3G1) was prepared using the general procedure of Example 19 with monomer MTC-C3G1. Yield: 74%; $^1$H-NMR (400 MHz, CDCl$_3$, 22° C.): δ 11.49 (s, 18H, NH), 8.43 (bs, 18H, NH), 5.10 (s, 2H, initiator —CH$_2$—), 4.36-4.25 (m, 69H, CH$_a$H$_b$ and CH$_a$H$_b$), 4.23-4.17 (m, 39H, —OCH$_2$—), 3.56-3.46 (m, 37H, —CH$_2$N—), 2.34 (s, 3H, initiator —CH$_3$), 1.93 (m, 38H, —CH$_2$—), 1.46 (d, J=23.0 Hz, 386H, Boc —CH$_3$), 1.24 (bs, 69H, —CH$_3$).

P(MTC-C3G1) was deprotected using the procedure of Example 19, forming cationic polymer PC3G-20. Yield: 80%; $^1$H-NMR (400 MHz, CD$_3$OD, 22° C.): δ 4.32 (s, 70H, CH$_a$H$_b$ and CH$_a$H$_b$), 4.23 (m, 39H, —OCH2—), 3.28 (m, —CH$_2$N—, overlapped with residual H$_2$O peak), 2.01-1.88 (m, 38H, —CH$_2$—), 1.24 (bs, 61H, —CH$_3$).

Example 24

Preparation of cationic homopolymer PC4G-20, x=20.

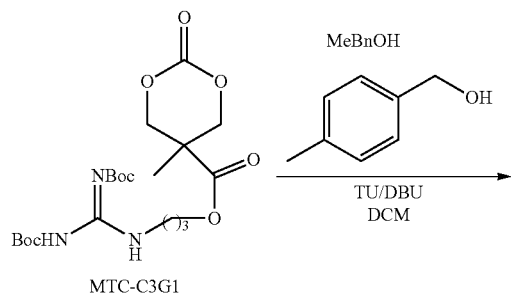

MTC-C3G1

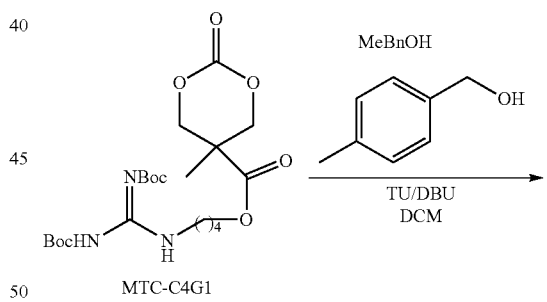

MTC-C4G1

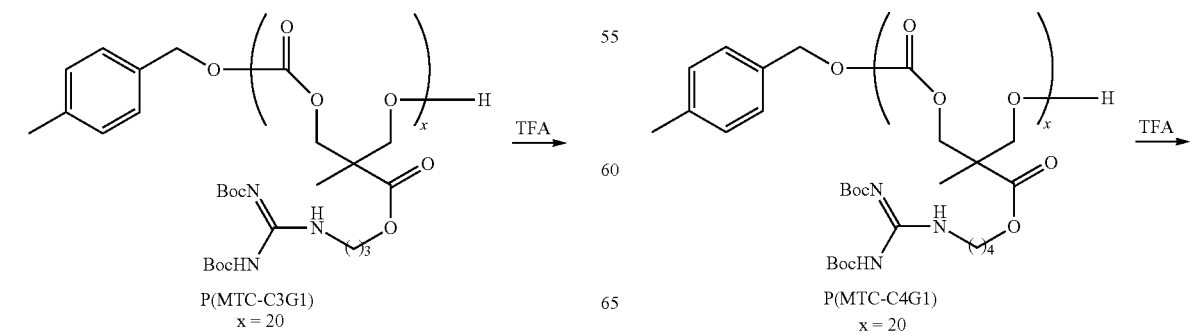

P(MTC-C3G1)
x = 20

P(MTC-C4G1)
x = 20

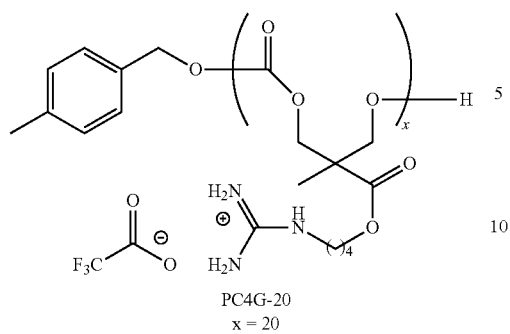

PC4G-20
x = 20

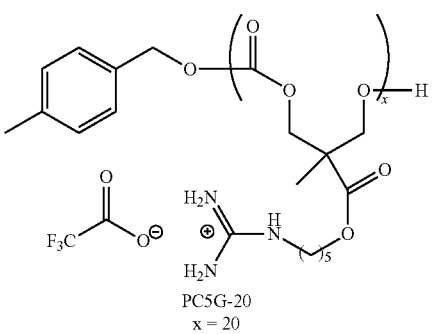

PC5G-20
x = 20

Preparation of intermediate homopolymer P(MTC-C4G1). P(MTC-C4G1) was prepared by the procedure of Example 19 with monomer MTC-C4G1. Yield: 72%; $^1$H-NMR (400 MHz, CDCl$_3$, 22° C.): δ 11.50 (s, 18H, NH), 8.36 (bs, 18H, NH), 5.09 (s, 2H, initiator —CH$_2$—), 4.29 (m, 66H, CH$_a$H$_b$ and CH$_a$H$_b$), 4.14 (m, 35H, —OCH$_2$—), 3.45 (m, 36H, —CH$_2$N—), 2.34 (s, 3H, initiator —CH$_3$), 1.72-1.63 (m, 71H, —CH$_2$—), 1.53-1.41 (d, 363H, Boc —CH$_3$), 1.28-1.18 (bs, 57H, —CH$_3$).

Deprotection of P(MTC-C4G1). P(MTC-C4G1) was deprotected using the procedure of Example 19, forming cationic polymer PC4G-20. Yield: 81%; $^1$H-NMR (400 MHz, CD$_3$OD, 22° C.): δ 4.30 (m, 61H, CH$_a$H$_b$ and CH$_a$H$_b$), 4.18 (m, 36H, —OCH$_2$—), 3.22 (m, 36H, —CH$_2$N—), 1.77-1.64 (m, 69H, —CH$_2$—), 1.23 (bs, 53H, —CH$_3$).

Preparation of intermediate homopolymer P(MTC-C5G1), x=20. P(MTC-C5G1) was prepared by the procedure of Example 19 using MTC-05G1. Yield: 70%; $^1$HE-NMR (400 MHz, CDCl$_3$, 22° C.): δ 11.53 (s, 19H. NH), 8.41 (bs, 19H, NH), 5.12 (s, 2H, initiator —CH$_2$—), 4.44-4.23 (m, 80H, CH$_a$H$_b$ and CH$_a$H$_b$), 4.14 (m, 43H, —CH$_2$—), 3.46 (m, 42H, —CH$_2$—), 2.36 (s, 3H, initiator —CH$_3$), 1.66 (m, 101H, —CH$_2$—), 1.49 (d, J=22.2, 4.7 Hz, 410H, Boc —CH$_3$), 1.48-1.34 (m, 70H, —CH$_2$—), 1.26 (bs, 60H, —CH$_3$).

Deprotection of P(MTC-C5G1). P(MTC-C5G1) was deprotected using the procedure of Example 19, forming cationic polymer PC5G-20. Yield: 85%; $^1$H-NMR (400 MHz, CD$_3$OD, 22° C.): δ 4.31 (m, 78H, CH$_a$H$_b$ and CH$_a$H$_b$), 4.16 (m, 43H, —OCH$_2$—), 3.20 (m, 42H, —CH$_2$N—), 1.76-1.60 (m, 86H, —CH$_2$—), 1.52-1.40 (m, 44H, —CH$_2$—), 1.23 (bs, 65H, —CH$_3$).

Example 26

Preparation of cationic homopolymer PiPrG-10, x=10.

Example 25

Preparation of cationic homopolymer PCSG-20, x=20.

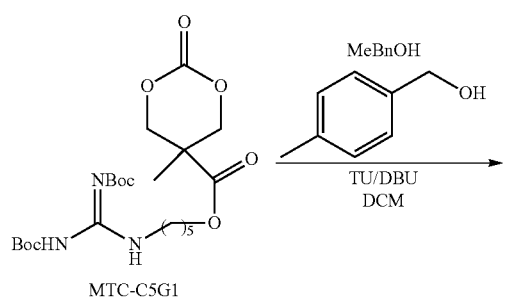

MTC-C5G1

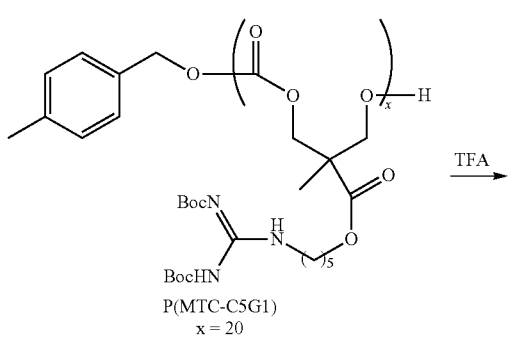

P(MTC-C5G1)
x = 20

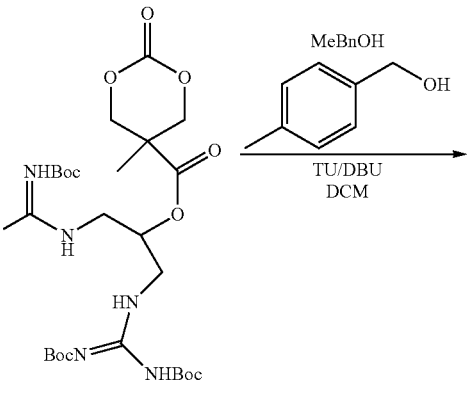

MTC-iPrG1

-continued

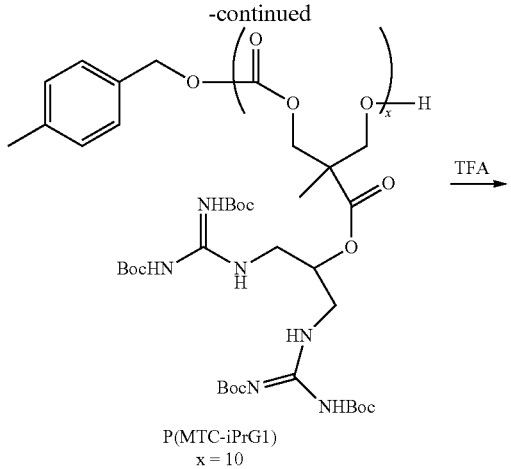

P(MTC-iPrG1)
x = 10

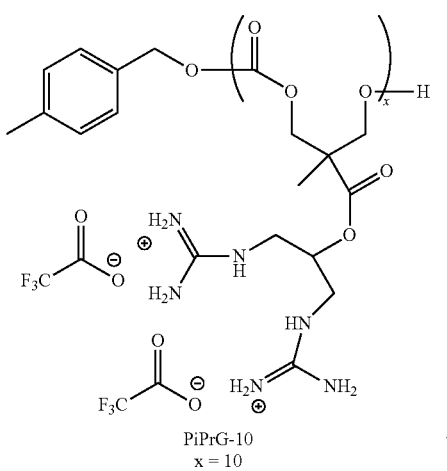

PiPrG-10
x = 10

Preparation of intermediate homopolymer P(MTC-iPrG1), x=10. P(MTC-iPrG1) was prepared using the procedure of Example 19 and monomer MTC-iPrG1. Yield: 72%; $^1$H-NMR (400 MHz, CDCl$_3$, 22° C.): δ 11.46 (s, 19H, NH), 8.56 (bs, 19H, NH), 5.16 (bs, 10H, —CH), 5.04 (s, 2H, initiator —CH$_2$—), 4.27 (m, 35H, CH$_a$H$_b$ and CH$_a$H$_b$), 3.97-3.77 (m, 19H, —CH$_2$—), 3.59 (s, 21H, —CH$_2$—), 2.33 (s, 3H, initiator —CH$_3$), 1.46 (m, 364H, Boc —CH$_3$), 1.27 (bs, 30H, —CH$_3$).

Deprotection of P(MTC-iPrG1). P(MTC-iPrG1) was deprotected using the procedure of Example 19, forming cationic polymer PiPrG-10. Yield: 82%; $^1$H-NMR (400 MHz, CD$_3$OD, 22° C.): δ 5.24-5.17 (m, 10H, —CH), 4.42-4.28 (m, 37H, CH$_a$H$_b$ and CH$_a$H$_b$), 3.58-3.49 (m, 42H, —CH$_2$—, slightly overlapped with residual THF peak), 1.29 (bs, 24H, —CH$_3$).

Example 27

Preparation of cationic homopolymer PCyG-20, x=20.

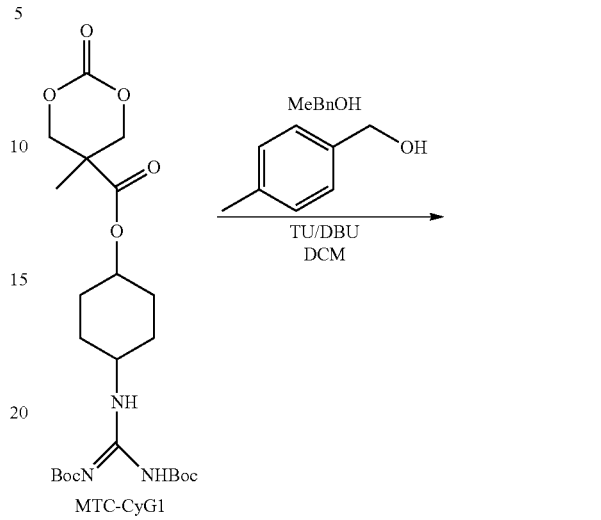

MTC-CyG1

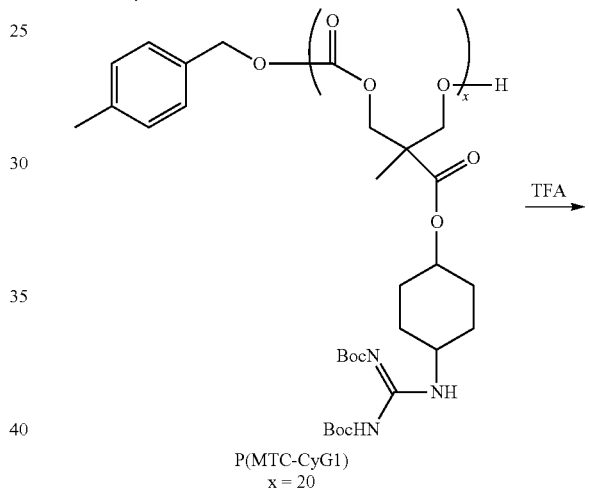

P(MTC-CyG1)
x = 20

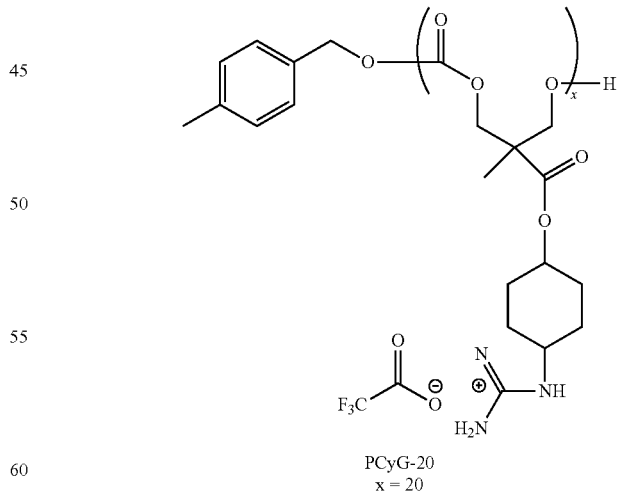

PCyG-20
x = 20

Preparation of intermediate homopolymer P(MTC-CyG1), x=20. P(MTC-CyG1) was prepared by the procedure of Example 19 using MTC-CyG1. Yield: 71%; $^1$H-NMR (400 MHz, CDCl$_3$, 22° C.): δ 11.53 (s, 19H, NH), 8.35 (bs, 18H, NH), 5.12 (s, 2H, initiator —CH$_2$—), 4.80

(m, 19H, —CH), 4.37-4.22 (m, 69H, CH$_a$H$_b$ and CH$_a$H$_b$), 4.10 (s, 19H, —CH$_2$—), 2.37 (s, 3H, initiator —CH$_3$), 2.10 (m, 41H, —CH$_2$—), 1.96 (m, 40H, —CH$_2$—), 1.64 (m, 40H, —CH$_2$—), 1.49 (d, J=13.7 Hz, 416H, Boc —CH$_3$), 1.38 (m, 43H, —CH$_2$—), 1.23 (bs, 64H, —CH$_3$).

Deprotection of P(MTC-CyG1). P(MTC-CyG1) was deprotected using the procedure of Example 19, forming cationic polymer PCyG-20. Yield: 82%; $^1$H-NMIR (400 MHz, CD$_3$OD, 22° C.): δ 4.77 (m, 19H, —CH), 4.37-4.19 (m, 70H, CH$_a$H$_b$ and CH$_a$H$_b$), 3.45 (m, 20H, —CH), 2.00 (m, 77H, —CH$_2$—), 1.60-1.40 (m, 80H, —CH$_2$—), 1.21 (bs, 58H, —CH$_3$).

Example 28

Preparation of cationic homopolymer PPhG-20, x=20.

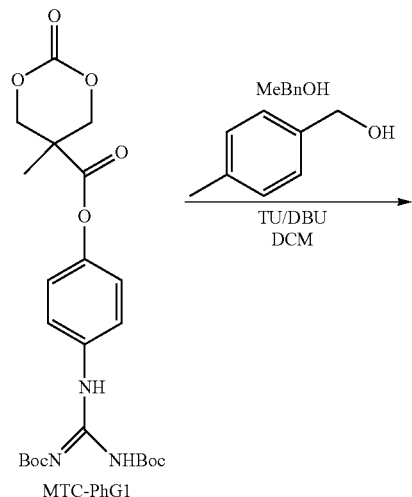

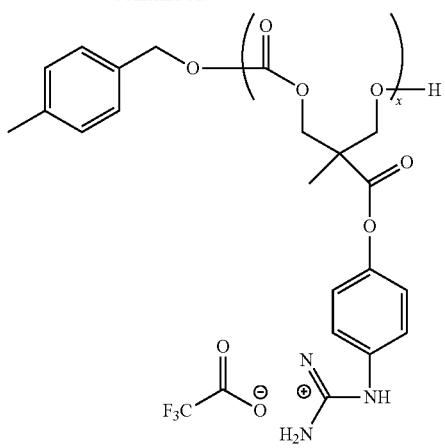

PPhG-20
x = 20

Preparation of intermediate homopolymer P(MTC-PhG1), x=20. P(MTC-PhG1) was prepared by the procedure of Example 19 using MTC-PhG1. Yield: 70%; $^1$H-NMR (400 MHz, CDCl$_3$, 22° C.): δ 11.64 (s, 16H, NH), 10.34 (bs, 16H, NH), 7.54 (m, 35H, Ph —CH), 7.04-6.97 (m, 36H, Ph —CH), 5.12 (s, 2H, initiator —CH$_2$—), 4.67-4.16 (m, 88H, CH$_a$H$_b$ and CH$_a$H$_b$), 2.34 (s, 3H, initiator —CH$_3$), 1.56-1.42 (m, 383H, Boc —CH$_3$ and —CH$_3$).

Deprotection of P(MTC-PhG1). P(MTC-PhG1) was deprotected using the procedure of Example 19, forming cationic polymer PPhG-20. Yield: 86%; $^1$H NMR (400 MHz, CD$_3$OD, 22° C.) δ 7.25 (m, 71H, Ph —CH), 4.48 (bs, 71H, CH$_a$H$_b$ and CH$_a$H$_b$), 1.39 (m, 55H, —CH$_3$).

Example 29

Preparation of homopolymer PBnG-20, x=20.

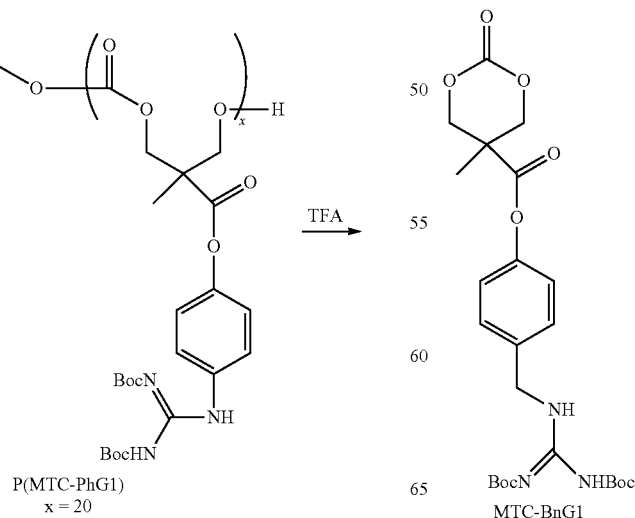

Example 30

Preparation of cationic homopolymer PC2Tu-20, x=20 was accomplished in two steps.

A) Preparation of homopolymer P(MTC-C2Br), x=20.

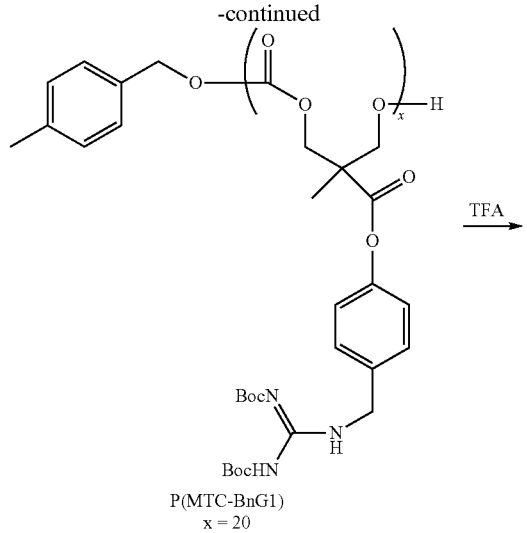

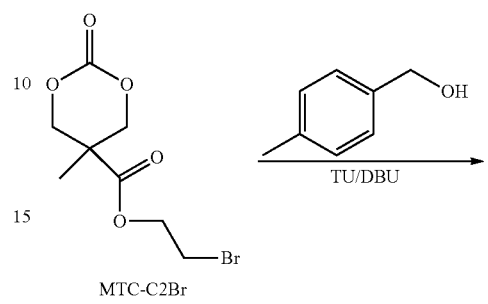

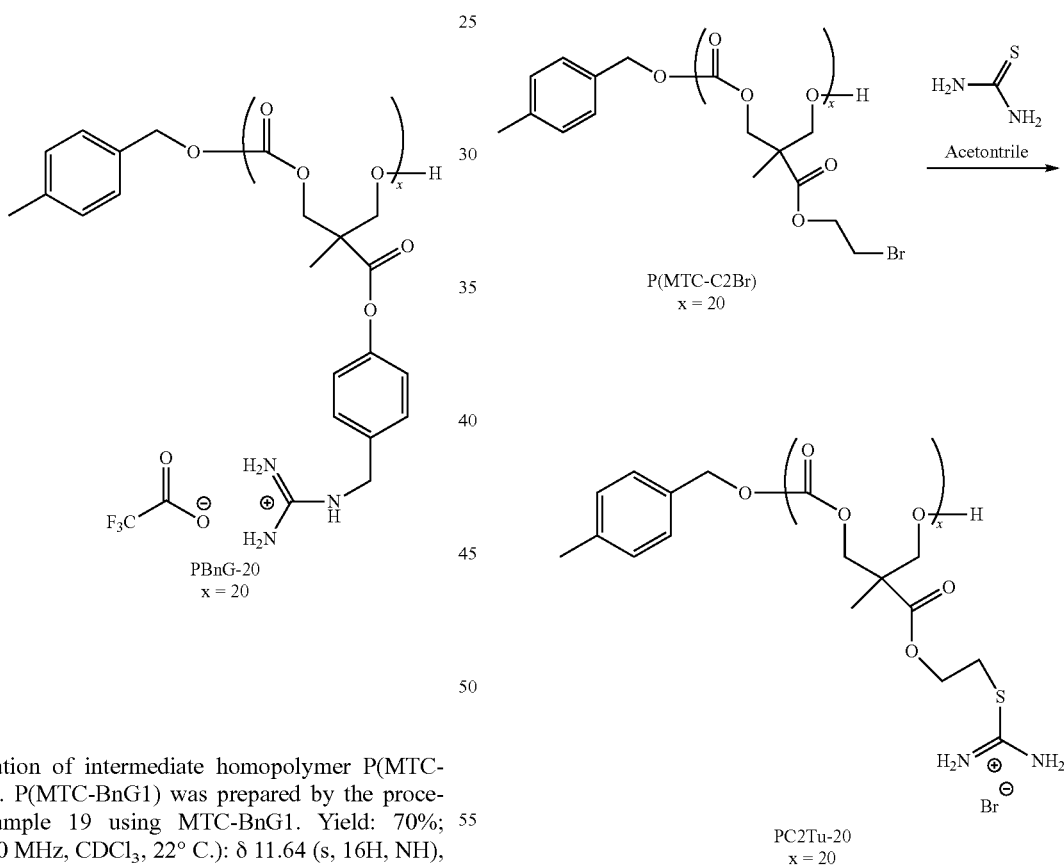

A) Preparation of intermediate homopolymer P(MTC-BnG1), x=20. P(MTC-BnG1) was prepared by the procedure of Example 19 using MTC-BnG1. Yield: 70%; $^1$H-NMR (400 MHz, CDCl$_3$, 22° C.): δ 11.64 (s, 16H, NH), 10.34 (bs, 16H, NH), 7.54 (m, 35H, Ph —CH), 7.04-6.97 (m, 36H, Ph —CH), 5.12 (s, 2H, initiator —CH$_2$—), 4.67-4.16 (m, 88H, CH$_a$H$_b$ and CH$_a$H$_b$), 2.34 (s, 3H, initiator —CH$_3$), 1.56-1.42 (m, 383H, Boc —CH$_3$ and —CH$_3$).

Deprotection of P(MTC-BnG1). P(MTC-BnG1) was deprotected using the procedure of Example 19, forming cationic polymer PBnG-20. Yield: 84%; $^1$H-NMR (400 MHz, CD$_3$OD, 22° C.): δ 7.28-7.39 (m, 39H, Ph —CH), 7.16-7.03 (m, 40H, Ph —CH), 4.60-4.29 (m, 115H, CH$_a$H$_b$, CH$_a$H$_b$ and —CH$_2$—), 1.47-1.30 (m, 60H, —CH$_3$).

P(MTC-C2Br) was prepared by the procedure of Example 19 using MTC-C2Br. Yield: 79%; $^1$H-NMR (400 MHz, CDCl$_3$, 22° C.): δ 5.12 (s, 2H, initiator —CH$_2$—), 4.53-4.24 (m, 101H, CH$_a$H$_b$, CH$_a$H$_b$ and —CH$_2$—), 3.54 (m, 35H, —CH$_2$—), 2.36 (s, 3H, initiator —CH$_3$), 1.31 (s, 53H, —CH$_3$).

B) Treatment of P(MTC-C2Br) with thiourea. To a reaction vial containing the precursor bromide-functionalized polymer P(MTC-C2Br) (150 mg) dissolved in acetonitrile (5 mL), thiourea (5.0 equivalents with respect to bromide groups) was added in excess and stirred at 50-60° C. for 12-16 hours. Upon cooling of the reaction mixture, the excess thiourea was removed via precipitation in acetone twice. Subsequent removal of the solvent in vacuo furnished a white powder as the product in quantitative yields. The polymer was then dissolved in water and lyophilized to yield a white transparent solid cationic polymer PC2Tu-20 as the isothiouronim-functionalized oligocarbonate. Complete thiourea substitution was determined from $^1$H-NMIR analysis. Yield: 92%; $^1$H-NMIR (400 MHz, $d_6$-DMSO, 22° C.): δ 9.11 (bs, 69H, —NH), 7.27 (d, J=8.0 Hz, 2H, initiator Ph —CH), 7.19 (s, 2H, initiator Ph —CH), 5.08 (s, 2H, initiator —CH$_2$—), 4.25 (m, 110H, CH$_a$H$_b$, CH$_a$H$_b$ and —CH$_2$—), 3.48 (bs, 38H, —CH$_2$—), 2.30 (s, 3H, initiator —CH$_3$), 1.14 (s, 57H, —CH$_3$).

5 Block Copolymers for Antimicrobial Hydrogels

Example 31

Preparation of 2-armed linear block copolymer BCP-1 by organocatalyzed ring opening polymerization initiated by diol MPA-OCH2Tol.

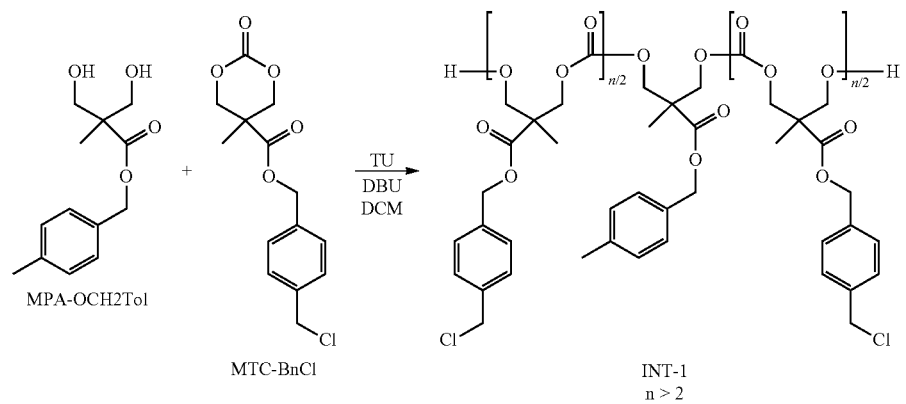

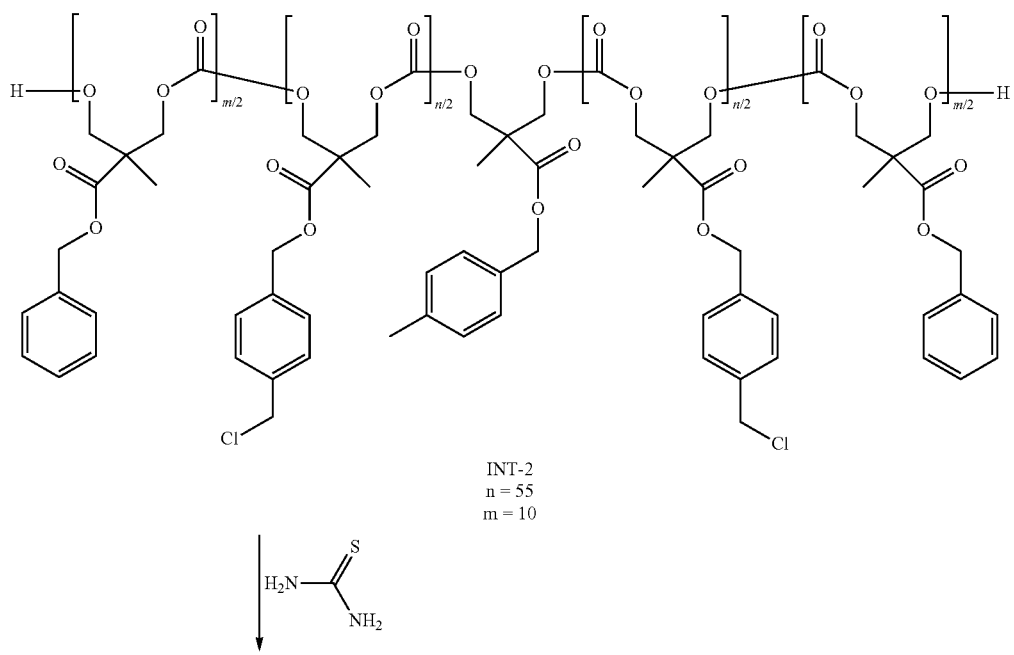

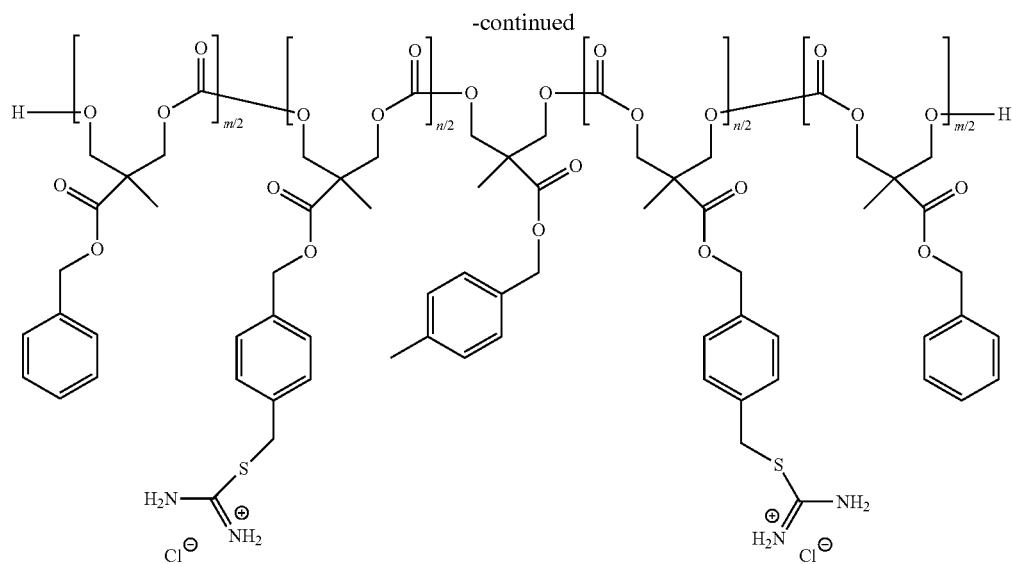

Int-2
n = 55 m = 10
BCP-1

The following procedure is representative. In a nitrogen filled glovebox, a 20 mL glass vial was charged with MTC-BnCl (1.2 g, 4.0 mmol), MPA-OCH2Tol (24 mg, 0.11 mmol, initiator), 1-(3,5-bis(trifluoromethyl)-phenyl)-3-cyclohexyl-2-thiourea (TU, 74 mg, 0.20 mmol), a Teflon-coated stir bar, and dry DCM (4 mL). After the solids dissolved, 1,8-diazabicyclo[5.4.0]undec-7-ene (DBU, 30 mg, 0.2 mmol) was added to start the polymerization. The reaction mixture was stirred for 30 minutes at room temperature, at which point a small aliquot (0.1 mL) of the crude mixture was removed for $^1$H NMR and GPC analysis. A solution of MTC-OBn (0.5 g, 2.0 mmol) in DCM (2 mL) was then added to the reaction mixture containing intermediate polymer INT-1, and stirring was continued for another 30 minutes. An excess of benzoic acid (30 mg, 0.24 mmol) was added to quench the catalyst and stop the polymerization. The crude reaction mixture was then precipitated into cold methanol (20 mL). Two cycles of centrifugation/decantation of the supernatant, followed by drying under reduced pressure, afforded the desired intermediate polymer INT-2 as a white solid (1.4 g, 82% yield). $^1$H NMR (400 MHz, CDCl3): 7.38-7.29 (m, 226H), 5.15 (s, 95H), 4.57 (s, 71H), 2.33 (s, 3H), 1.25 (s, 144H). In the above structure m=10 and n=55.

To a 20 mL glass vial was added polymer INT-2 (700 mg, 1.83 mmol BnCl groups), thiourea (290 mg, 3.8 mmol), and DMF (5 mL). The reaction mixture was stirred for 18 hours at room temperature, transferred directly to a dialysis membrane (1000 Da molecular weight cutoff (MWCO)), and dialyzed against a 3:1 v/v 2-propanol:acetonitrile mixture for 18 hours. Concentration under reduced pressure afforded the desired polymer BCP-1 as a white solid (872 mg, 99% yield). $^1$H NMR (400 MHz, DMSO-d6): 9.35 (br, 3H), 7.44-7.30 (m, 4.5H), 5.10 (s, 2H), 4.55 (s, 1.6H), 4.24 (m, 4H), 1.19 (s, 3H).

Example 32

Preparation of 2-armed linear block copolymer BCP-2 by organocatalyzed ring opening polymerization initiated by diol MPA-OCH2Tol. The procedure of Example 31 was followed using MTC-BnCl (1.2 g, 4.0 mmol), MPA-OCH2Tol (24 mg, 0.10 mmol, initiator), 1-(3,5-bis(trifluoromethyl)-phenyl)-3-cyclohexyl-2-thiourea (TU, 74 mg, 0.20 mmol), DCM (4 mL), 1,8-diazabicyclo[5.4.0]undec-7-ene (DBU, 30 mg, 0.2 mmol), and subsequently MTC-OBn (0.50 g, 2.0 mmol) and DCM (2 mL). For BCP-2, m=12 and n=34.

Example 33

Preparation of 2-armed linear block copolymer BCP-2 by organocatalyzed ring opening polymerization initiated by diol MPA-OCH2Tol. The procedure of Example 31 was followed using MTC-BnCl (0.60 g, 2.0 mmol), MPA-OCH2Tol (24 mg, 0.10 mmol, initiator), 1-(3,5-bis(trifluoromethyl)-phenyl)-3-cyclohexyl-2-thiourea (TU, 30 mg, 0.08 mmol), DCM (2 mL), 1,8-diazabicyclo[5.4.0]undec-7-ene (DBU, 12 mg, 0.08 mmol), and subsequently MTC-OBn (0.50 g, 2.0 mmol) and DCM (2 mL). For BCP-2, m=17 and n=21.

Example 34

Preparation of triblock copolymer TBP-1 by organocatalyzed ring opening polymerization of MTC-Bn initiated by HO-PEG-OH.

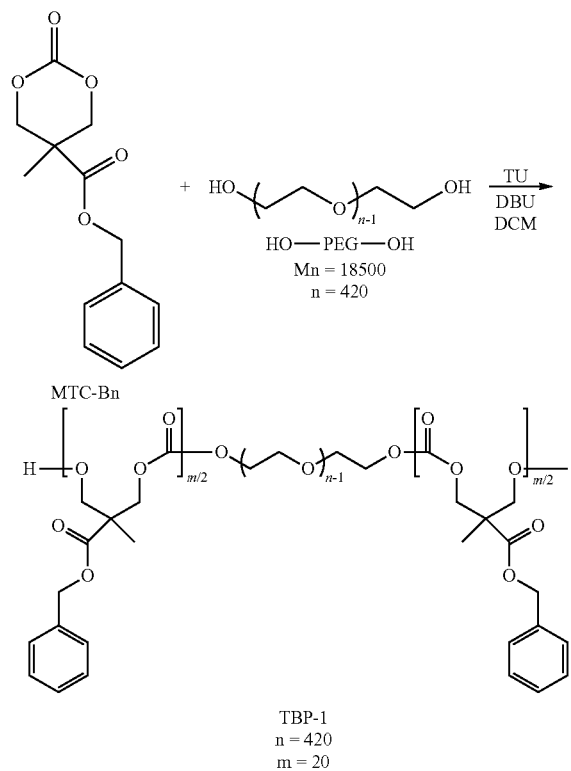

MTC-Bn

TBP-1
n = 420
m = 20

In a nitrogen filled glovebox, a 20 mL glass vial was charged with azeotropically dried poly(ethylene glycol) (HO-PEG-OH) (Mn=18500; 2.03 g, 0.140 mmol), MTC-OBn (0.549 g, 2.2 mmol), TU (33 mg, 0.09 mmol), a Teflon-coated stir bar, and dry DCM (4 mL). After the solids dissolved, DBU (0.2M premade solution in DCM; 0.45 mL, 0.09 mmol) was added to start the polymerization. After stirring for 30 minutes at room temperature, an excess of benzoic acid (30 mg, 0.24 mmol) was added to quench the catalyst and stop the polymerization. The crude reaction mixture was then precipitated into diethyl ether (40 mL). Three cycles of centrifugation/decantation of the supernatant, followed by drying under reduced pressure, afforded the desired polymer as a white solid (2.49 g, 97% yield). $^1$H NMR (400 MHz, CDCl$_3$): δ 7.32-7.26 (br, 128H), 5.13 (s, 40H), 4.26 (s, 72H), 3.64 (s, 1680H), 1.23 (s, 56H).

Table 2 summarizes the prepared cationic homopolymers, cationic block copolymers BCP-1 to BCP-3, and non-charged triblock copolymer TBP-1, where I=isothiouronium, G=guanidinium, and D=diguanidinium, and NA=not applicable. The spacer group is the group separating the ester oxygen of the side chain from the guanidinium nitrogen or isothiouronium sulfur.

TABLE 2

| Example | Polymer Name | Cationic Group | Spacer Group | DP (x) |
|---|---|---|---|---|
| 19 | PC2G-20 | G | *∼∼* | 20 |
| 20 | PC2G-5 | G | *∼∼* | 5 |
| 21 | PC2G-10 | G | *∼∼* | 10 |
| 22 | PC2G-40 | G | *∼∼* | 40 |
| 23 | PC3G-20 | G | *∼(∼)$_2$* | 20 |
| 24 | PC4G-20 | G | *∼(∼)$_3$* | 20 |
| 25 | PC5G-20 | G | *∼(∼)$_4$* | 20 |
| 26 | PiPrG-10 | D | isopropyl (3-arm) | 10 |
| 27 | PCyG-20 | G | 1,4-cyclohexyl | 20 |
| 28 | PPhG-20 | G | 1,4-phenylene | 20 |
| 29 | PBnG-20 | G | 4-(methyl)phenyl | 20 |
| 30 | PC2Tu-20 | I | *∼∼* | 20 |
| 31 | BCP-1 | I | *∼C$_6$H$_4$∼* | n = 55, m = 10 |
| 32 | BCP-2 | I | *∼C$_6$H$_4$∼* | n = 34, m = 12 |
| 33 | BCP-3 | I | *∼C$_6$H$_4$∼* | n = 21, m = 17 |
| 33 | TBP-1 | NA | NA | n = 420, m = 20 |

Surface Modified Silica Particles

Example 34

Preparation of monomer-modified silica particles APSi-C2G.

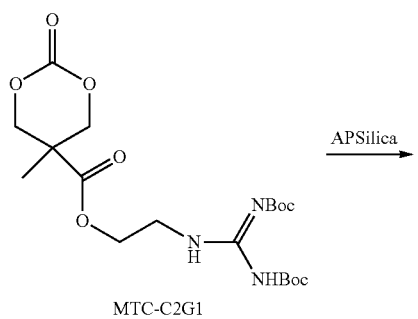

MTC-C2G1

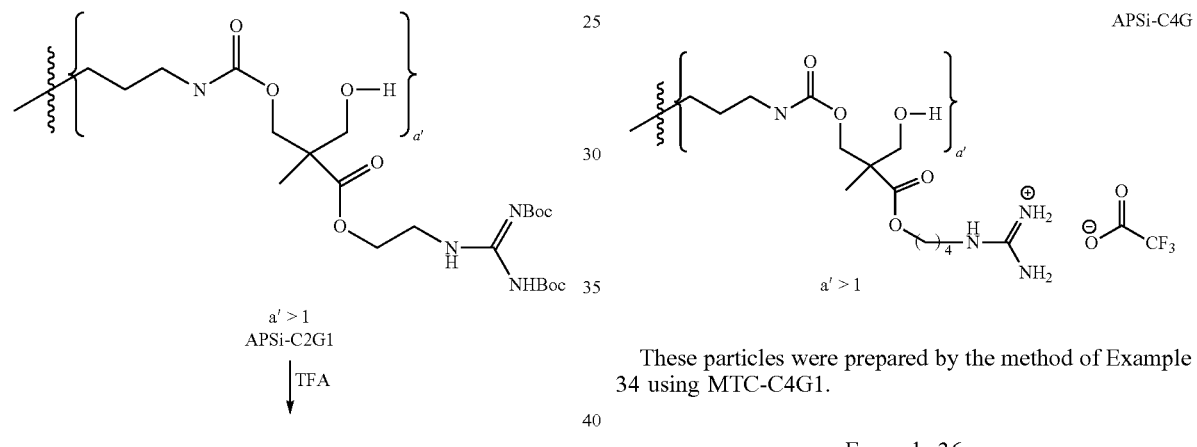

In the above structure of APSi-C2G, it should be understood that the ring opening reaction does not result in polymerization of the cyclic carbonate. The wavy line in the above reaction diagram represents the silica particle surface. The braces enclose a surface site containing an aminopropyl group. There are a'>1 number of surface sites containing aminopropyl groups. The following procedure is representative. A 2.0-mL centrifuge tube was charged with MTC-C2G1 (100 mg, 0.224 mmol, 1.2 equivalents) and dissolved in DMSO (1 mL). To this solution were added silica particles functionalized with aminopropyl surface groups (APSilica, 76.0 mg, 0.187 mmol, 1.0 equivalents) and triethylamine (TEA, 63 microliters, 0.448 mmol, 2.4 equivalents). The mixture was shaken continuously in a heating block at 800 rpm at 60° C. for 18 hours. After 18 hours, the surface modified silica particles (APSi-C2G1) were washed repeatedly with DCM for three times to remove unreacted monomers.

For the removal of Boc groups, the APSi-C2G1 particles were re-suspended in DCM (5 mL) and trifluoroacetic acid (TFA, 2 mL). The reaction mixture was sealed and stirred continuously at room temperature for 18 hours. The silica particles were then washed with DCM three times. Upon removal of the solvent in vacuo, the product APSi-C2G (silica particles containing deprotected guanidinium functional groups) was obtained.

Example 35

Preparation of monomer-modified silica particles APSi-C4G.

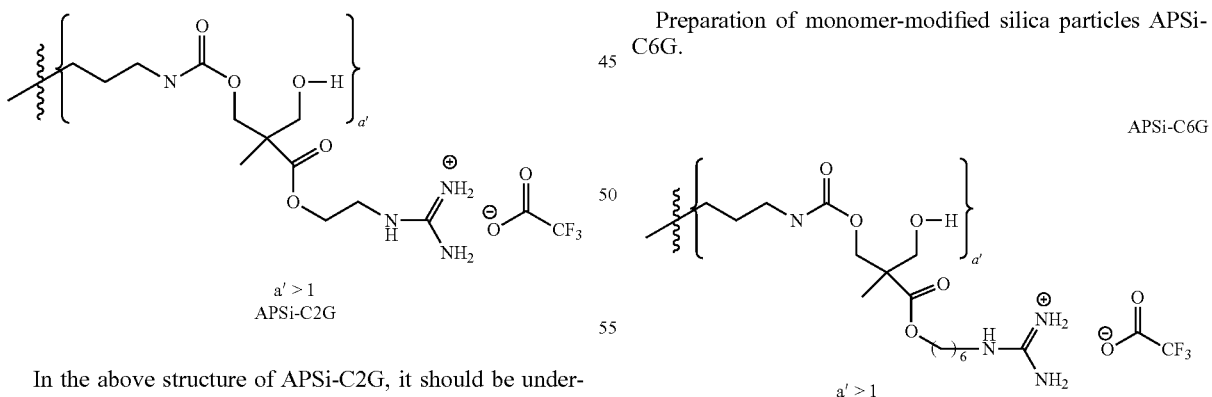

These particles were prepared by the method of Example 34 using MTC-C4G1.

Example 36

Preparation of monomer-modified silica particles APSi-C6G.

These particles were prepared by the method of Example 34 using MTC-C6G1.

Example 37

Preparation of polymer-modified silica particles APSi-TMC-PC2G.

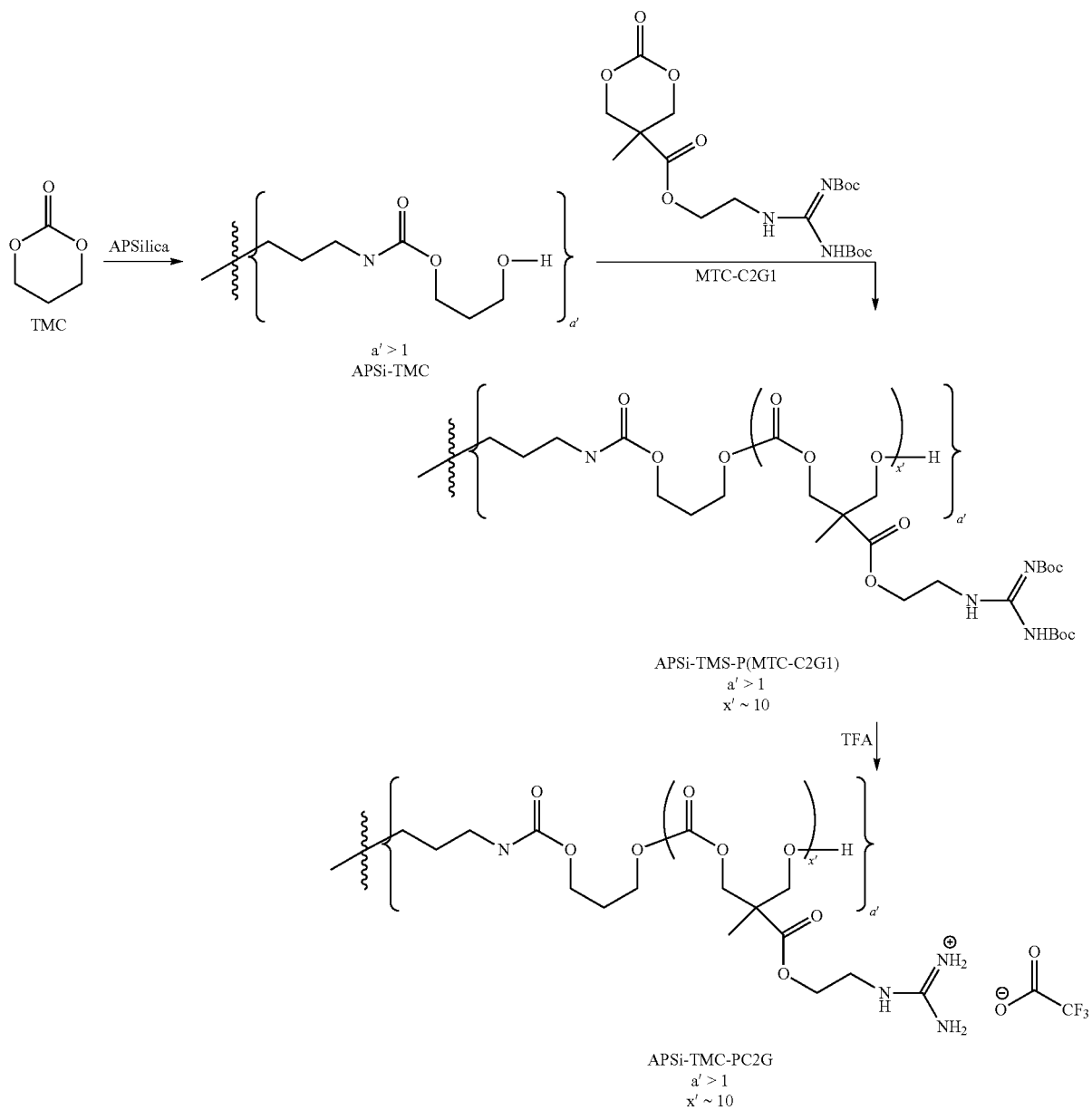

In the above reaction diagram, it should be understood that the ring opening of TMC does not occur with polymerization of TMC, whereas the ring opening of MTC-C2G1 occurs with polymerization of MTC-C2G1. The following procedure is representative. To create a macro-initiator for the ring opening polymerization, the aminopropyl functionalized silica particles (APSilica) were first treated with trimethylene carbonate (TMC). To a reaction vial, TMC (100 mg, 0.980 mmol, 1.2 equivalents) was added and dissolved in DMSO (2.5 mL). The mixture was subsequently combined with 3-aminopropyl-functionalized silica particles (APSilica, 332 mg, 0.816 mmol, 1.0 equivalents) and TEA (273 microliters, 1.959 mmol, 2.4 equivalents), and the mixture was stirred continuously in a oil bath at 60° C. for 18 hours. The TMC-functionalized silica particles were then washed repeatedly with DCM for three times to remove unreacted monomers. Upon removal of the solvent in vacuo, the TMC particles (APSi-TMC) were obtained as the product. The wavy line in the above structure of APSi-TMC represents the silica particle surface. The braces enclose a surface site containing an aminopropyl group linked to a TMC molecule. There are a'>1 number of surface sites containing aminopropyl groups linked to TMC.

Next, using a glove box, the APSi-TMC particles (10 mg, 0.025 mmol, 1.0 equivalents) were added to a reaction vial containing DBU (1.9 microliters, 0.0125 mmol) and TU (4.6 mg, 0.0125 mmol) dissolved in dry DCM (1 mL). The mixture was stirred for about 10 minutes and subsequently charged with MTC-BocC2G1 (111 mg, 0.25 mmol, 10.0 equivalents for a target degree of polymerization (DP) of 10) and left to stir continuously at room temperature for an additional 30 minutes. At the end of the reaction, an excess of benzoic acid was added to quench the catalyst. The modified silica particles were then washed repeatedly with DCM for three times. Upon removal of the solvent in vacuo, polymer-modified silica particles APSi-TMC-P(MTC-BocC2G1) were obtained as the product.

For the removal of Boc groups, the APSi-TMC-P(MTC-C2G1) particles were deprotected using TFA in DCM as described above. Upon removal of the solvent in vacuo, surface modified silica particles containing deprotected guanidinium functional groups, APSi-TMC-PC2G, were obtained as the product.

Example 38

Preparation of polymer-modified silica particles APSi-TMC-PC4G.

Figure 2:
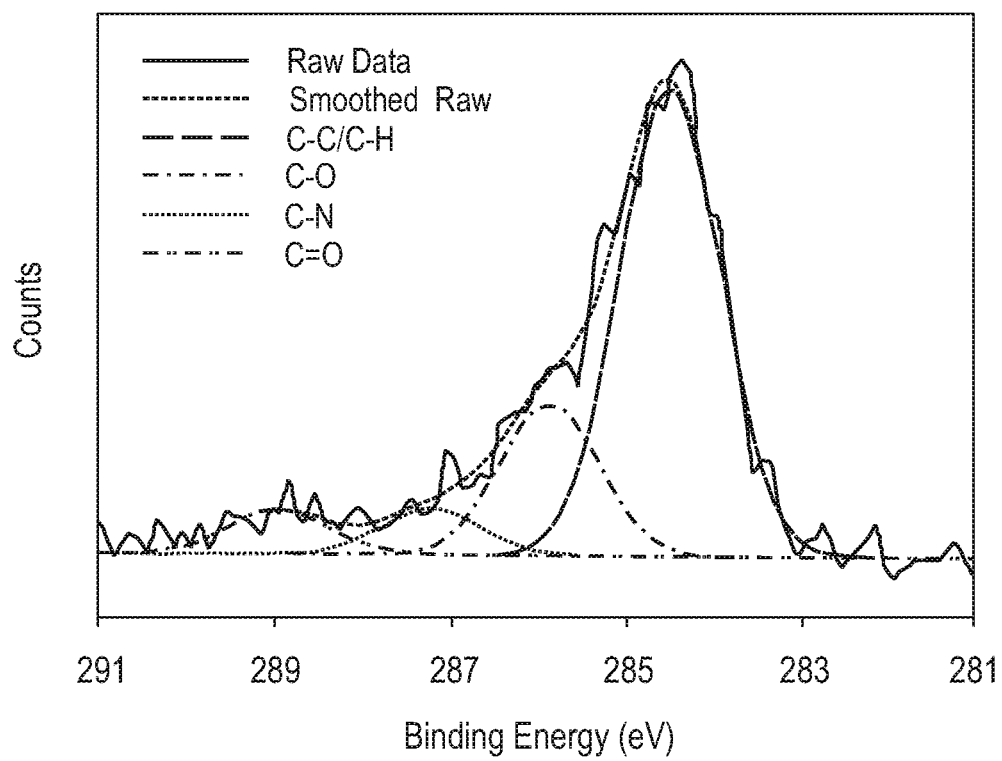
FIG. 2 is an XPS carbon 1 s core level spectrum of APSi-C4G. The deconvoluted peaks at 283-286, 284-288, 285-289 and 288-290 eV are attributed to the functional groups of C—C/C—H, C—O, C—N and C=O.
Figure 3:
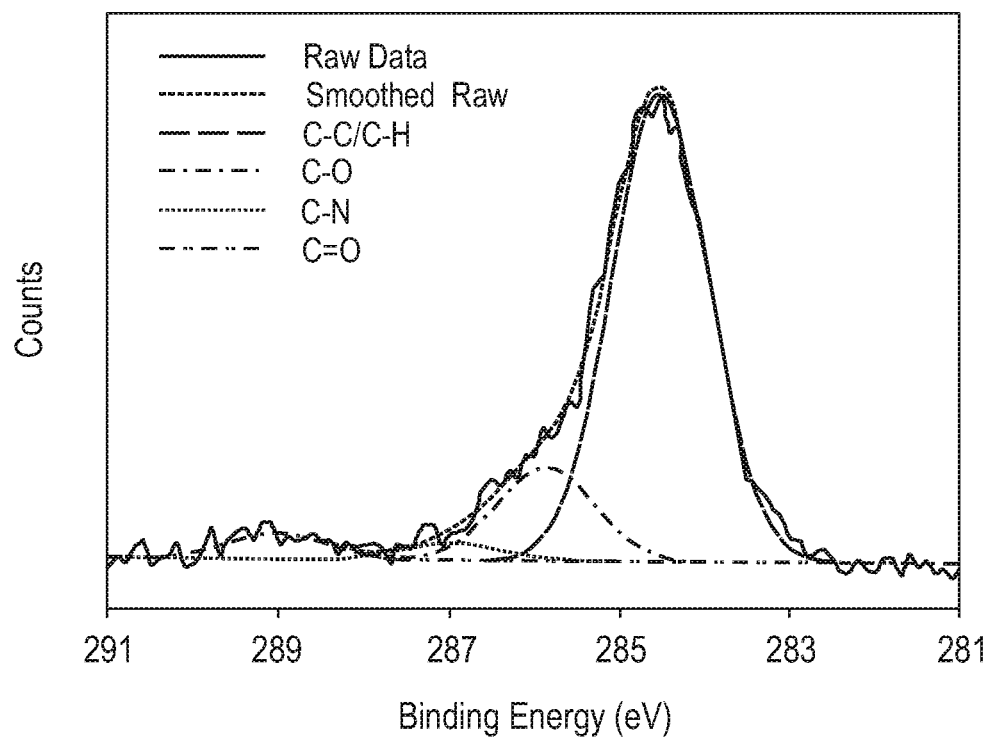
FIG. 3 is an XPS carbon 1 s core level spectrum of APSi-C6G. The deconvoluted peaks at 283-286, 284-288, 285-289 and 288-290 eV are attributed to the functional groups of C—C/C—H, C—O, C—N and C=O.

The XPS carbon is core level spectra of the APSi-C2G, APSi-C4G, and APSi-C6G particles are shown in FIGS. 1 to 3, respectively. The binding energy range in the high-resolution carbon is XPS spectra is about 283-290 eV, and the spectra of the surface-coated silica particles can be fitted with four component peaks. For C—C/C—H bonding, the carbon is binding energy value is equal to 284.5 eV. The observed deconvoluted peaks at 283-286, 284-288, 285-289 and 288-290 eV may be attributed to the functional groups of C—C/C—H, C—O, C—N and C=O, respectively, of the coated carbonate. These observed peaks suggest successful conjugation of the guanidinium-functionalized carbonate monomer.

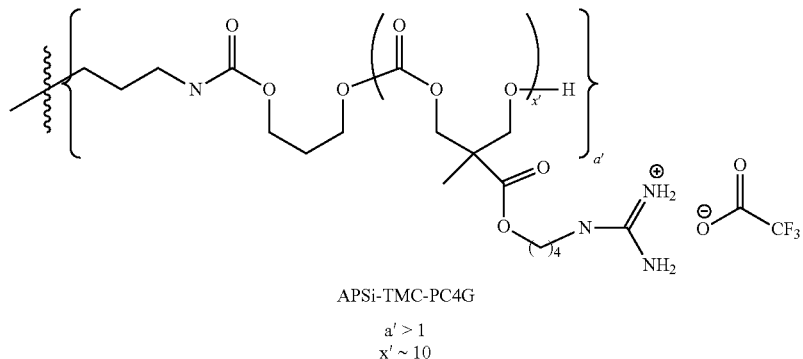

APSi-TMC-PC4G a' > 1
x' ~ 10

APSi-TMC-PC4G was prepared according to the general procedure of Example 35 using cyclic carbonyl monomer MTC-C4G1 and APSilica. The wavy line in the above structure of APSi-TMC-PC4G represents the silica particle surface.

Surface analysis by X-ray photoelectron spectroscopy (XPS) of the modified silica particles was conducted as follows. The surface composition of the silica particles was characterized by XPS using a Kratos AXIS Ultra DLD (delay-line detector) spectrometer equipped with a monochromatic Al Kα source (1486.7 eV) (Kratos Analytical Ltd.; Shimadzu Corp., Japan). The silica particles were mounted onto standard sample holders by means of double-sided adhesive tape. The X-ray power supply was run at 15 kV and 5 mA. The pressure in the analysis chamber during the measurements was typically $10^{-8}$ mbar and below. The angle between the sample surface and the detector was kept at 90°. The survey spectrum for each sample ranging from 1100 to 0 eV was acquired. All core level spectra were referenced to the carbon is hydrocarbon peak at 284.5 eV. In spectra deconvolution, the linewidth (full width half maximum) of the Gaussian peaks was maintained constant for all components in a particular spectrum.

Figure 4:
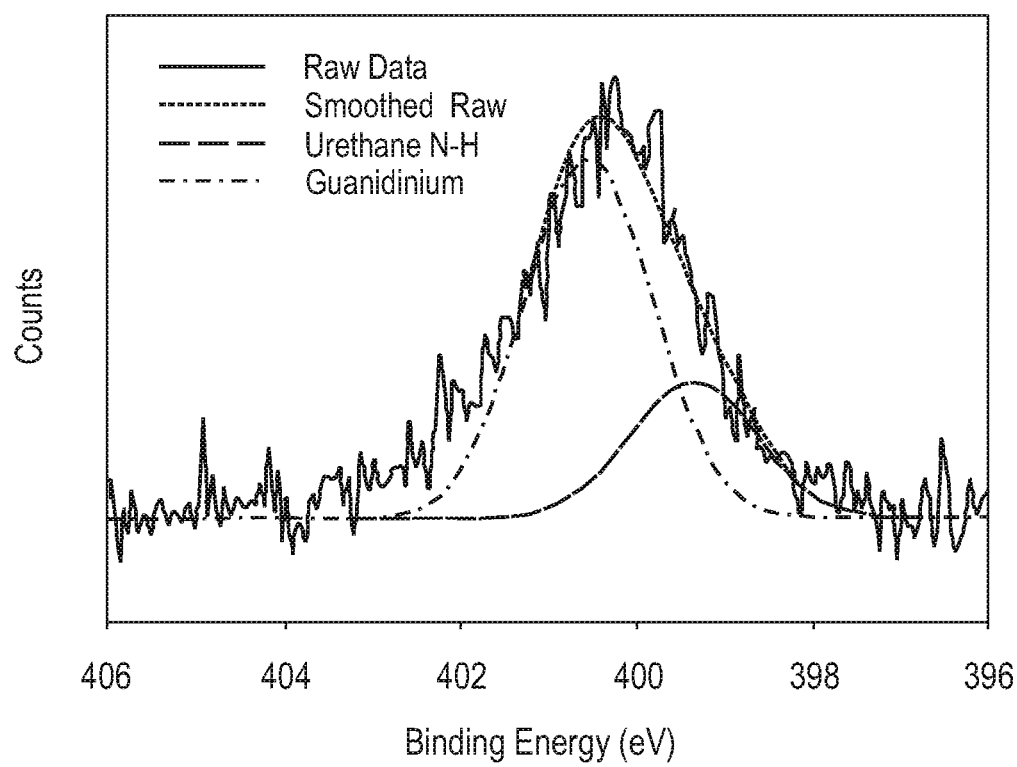
FIG. 4 is an XPS nitrogen is core level spectrum of APSi-C2G. The peak observed at ~399 eV is attributed to the N—H functional group arising from the urethane bond formed between the silica and the monomer. The peak at ~400 eV is attributable to the guanidinium functional group of the monomer, which is representative of the three nitrogen atoms with the delocalized positive charge.
Figure 5:
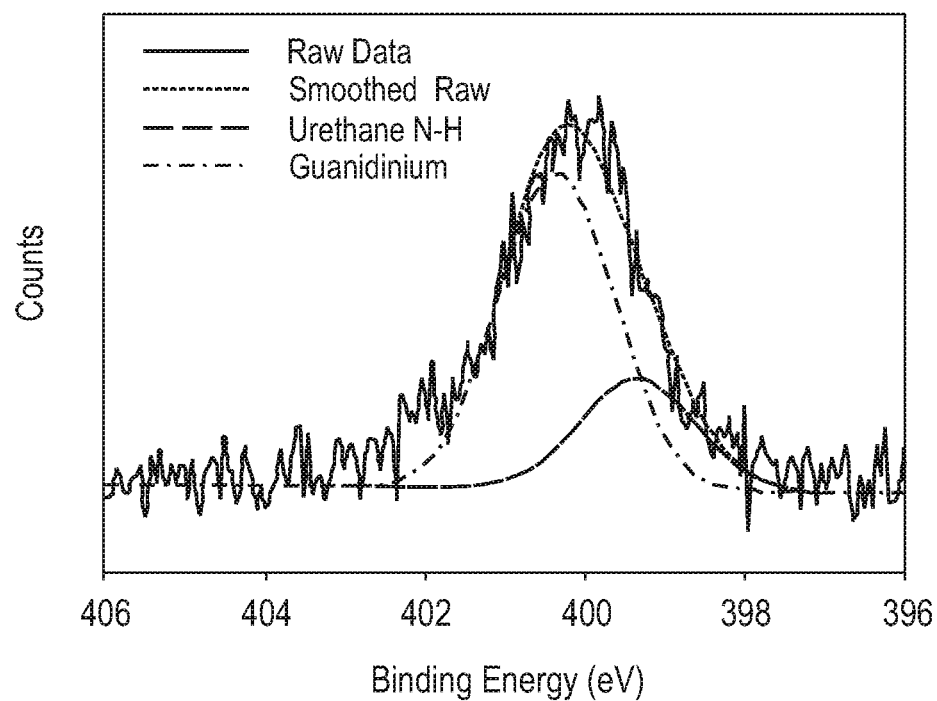
FIG. 5 is an XPS nitrogen is core level spectrum of APSi-C4G. The peak observed at ~399 eV is attributed to the N—H functional group arising from the urethane bond formed between the silica and the monomer. The peak at ~400 eV is attributable to the guanidinium functional group of the monomer, which is representative of the three nitrogen atoms with the delocalized positive charge.
Figure 6:
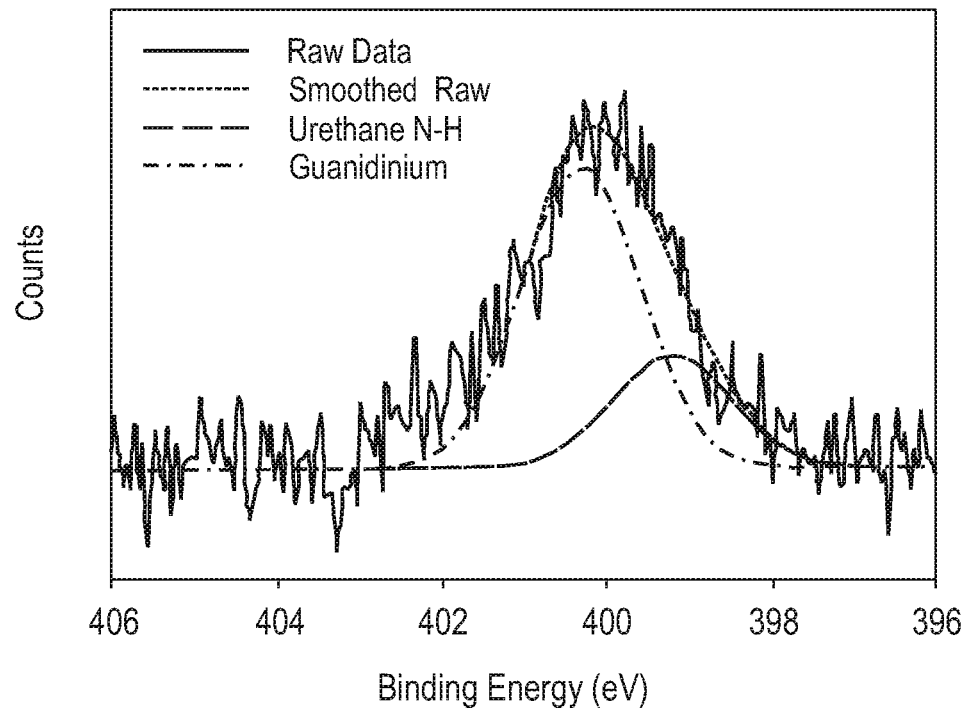
FIG. 6 is an XPS nitrogen is core level spectrum of APSi-C6G. The peak observed at ~399 eV is attributed to the N—H functional group arising from the urethane bond formed between the silica and the monomer. The peak at ~400 eV is attributable to the guanidinium functional group of the monomer, which is representative of the three nitrogen atoms with the delocalized positive charge.

The XPS nitrogen is core level spectra of the APSi-C2G, APSi-C4G, and APSi-C6G particles are shown in FIGS. 4 to 6, respectively. A predominant peak observed at ~399 eV may be attributed to the N—H functional group arising from the urethane bond formed between the silica and the monomer. An additional peak was observed at ~400 eV, attributable to the guanidinium functional group of the monomer, which is representative of the three nitrogen atoms with the delocalized positive charge. By analyzing the surface [N$^-$]/[N] ratio among the three samples, i.e., APSi-C2G ([N$^+$]/[N] ratio=2.7), APSi-C4G ([N$^+$]/[N] ratio=2.8) and APSi-C6G ([N$^+$]/[N] ratio=2.7), these values closely follow the expected peak area ratio of 3:1. This observation further confirms the presence of the carbonate on the silica surface.

Polymer Grafted Silica Particles

Example 39

Preparation of polymer-grafted silica particles APSi-PBnTU-10 (n=10). These silica particle grafted materials were prepared according to the following reaction scheme using APSilica. The wavy line in the structure of APSi-PBnTU-10 represents the silica particle surface.

75 76
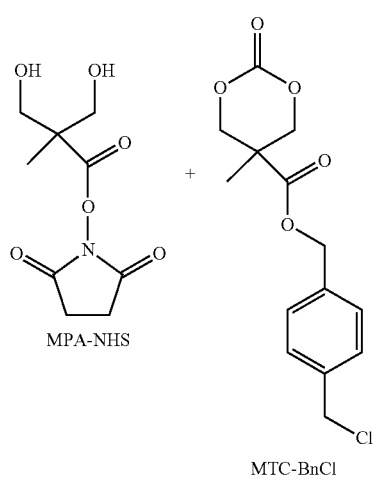
MPA-NHS
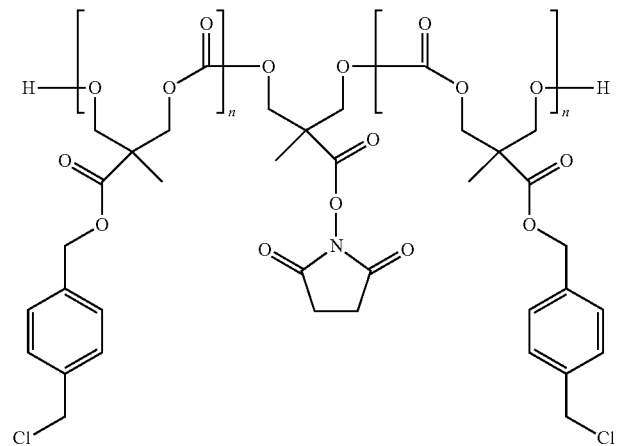
MTC-BnCl
TFSA
DCM
25° C., 18 h
I37
n = 10
ACN
50° C., 18 h
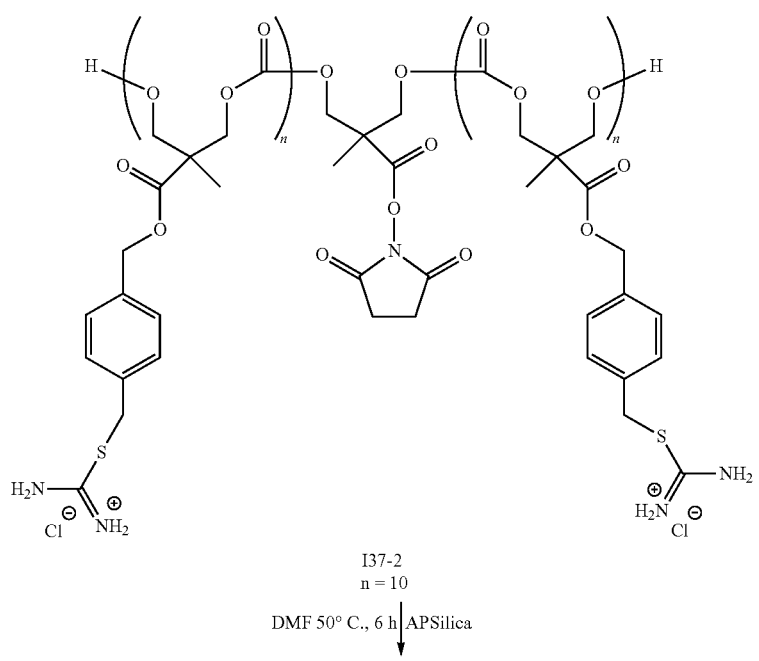
I37-2
n = 10
DMF 50° C., 6 h | APSilica

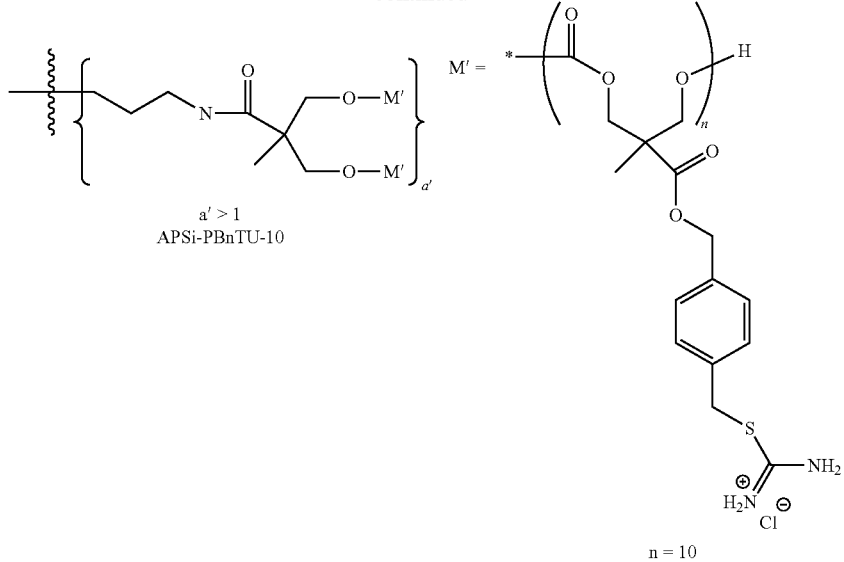

a' > 1
APSi-PBnTU-10 n = 10

Using a glove box, the MPA-NHS (5.8 mg, 0.025 mmol, 1.0 equivalents) was added to a reaction vial and dissolved in dry dichloromethane (DCM, 1 mL). The mixture was stirred for about 10 minutes and was subsequently charged with MTC-BnCl (149 mg, 0.5 mmol, 20.0 equivalents) for a target degree of polymerization (DP) of 20 (n=10 in the above structure of APSi-PBnTU-10). Triflic acid (TFSA, 2.2 microliters, 0.025 mmol, catalyst), was added, and the reaction mixture was stirred continuously at room temperature for 18 hours. The polymer was purified via precipitation in cold methanol. Two cycles of centrifugation/decantation of the supernatant, followed by subsequent removal of the solvent in vacuo, furnished intermediate polymer 137 as the product.

Next, to a reaction vial containing 137 dissolved in acetonitrile (ACN, 5 mL), thiourea (5.0 equivalents with respect to chloride groups) was added in excess and the reaction mixture was stirred at 50-60° C. for 18 hours. Upon cooling of the reaction mixture, the excess thiourea was removed via precipitation in acetonitrile twice. Subsequent removal of the solvent in vacuo furnished cationic polymer I37-2 as the product.

The polymer I37-2 was then grafted on silica surface as follows. A reaction vial was charged with a solution of I37-2 (500 mg, 0.5 equivalents based on amine groups of APsilica) dissolved in DMF (2 mL). Amino-functionalized silica particles APSilica (52 mg, 1.0 equivalents) was added and the reaction mixture was stirred at 50-60° C. for 6 hours. Upon cooling of the reaction mixture, the silica particles were washed repeatedly with DMF followed by DCM three times to remove unreacted polymer. Upon removal of the solvent in vacuo, polymer-grafted silica particles APSi-PBnTU-10 particles were obtained as the product.

Example 40

Preparation of polymer-grafted silica particles APSi-PBnTU-20 (n=20).

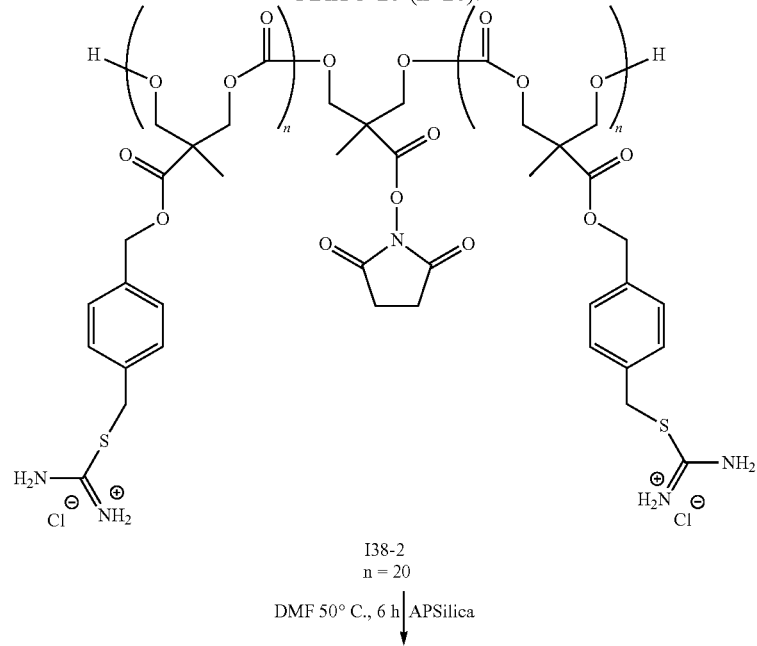

I38-2
n = 20

DMF 50° C., 6 h | APSilica

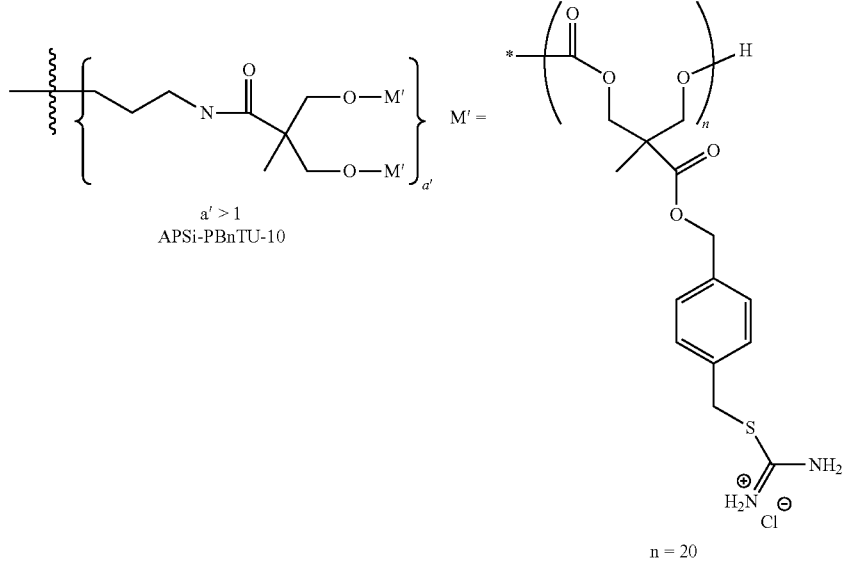

APSi-PBnTU-10 n = 20

Intermediate cationic polymer I38-2 below was prepared and grafted onto APSilica to form APSi-PBnTU-20 following the general procedure of Example 39 using MPA-NHS (5.8 mg, 0.025 mmol, 1.0 equivalents), MTC-BnCl (298 mg, 1.0 mmol, 40.0 equivalents), triflic acid (TFSA, 4.4 microliters, 0.05 mmol), dichloromethane (DCM, 2 mL), thiourea (5.0 equivalents with respect to chloride groups), acetonitrile (ACN, 5 mL), 138-2 (500 mg, 0.5 equivalents based on amine groups of APSilica), APSilica (26 mg, 1.0 equivalents), and dimethylformamide (DMF, 2 mL). The wavy line in the structure of APSi-PBnTU-20 above represents the silica particle surface.

Minimum Inhibitory Concentration (MIC)

Each microbial strain obtained from ATCC was re-constituted from its lyophilized form according to the manufacturer's protocol. Microbes from ATCC were cultured in Mueller-Hinton Broth (MHB) solutions, respectively, at 37° C. under constant shaking of 100 rpm. The MICs of the polymers were measured using the broth microdilution method. In this method, 100 microliters of MHB solution containing the polymer (with a fixed de-ionized (DI) water concentration of 20% v/v) at various concentrations (0-500 micrograms per milliliter) was placed into each well of a 96-well microplate. An equal volume of microbial suspension ($3 \times 10^5$ colony forming units (CFU) per mL) was added into each well. Prior to mixing, the microbial sample was first inoculated overnight to enter its log growth phase. The concentration of microbial solution was adjusted to give an initial optical density (OD) reading of approximately 0.07 at 600 nm wavelength on a microplate reader (TECAN, Switzerland), which corresponds to the concentration of McFarland 1 solution ($3 \times 10^8$ CFU/mL). The microbial solution was then further diluted 1000-fold to achieve an initial inoculum of $3 \times 10^5$ CFU/mL. The 96-well plate was kept in an incubator at 37° C. under constant shaking of 100 revolutions per minute (rpm) for 18 hours. The MIC was taken as the concentration of the polymer at which no microbial growth was observed with unaided eyes and the microplate reader at the end of 18 hours incubation. For *C. albicans*, MIC readings were determined after a longer incubation time of 42 hours. Broth containing microbial cells alone was used as the negative control, and each test was carried out in 6 replicates. The results are reported in Table 3 below.

Haemolysis Assay

The toxicity of the polymers against mammalian erythrocytes was tested using fresh rat red blood cells (rRBCs). The rRBCs were diluted 25-fold in PBS to achieve 4% v/v of blood content. The polymers were dissolved in PBS at concentrations ranging from 0-4000 micrograms per mL by serial dilutions. Equal volumes of polymer solutions (100 microliters) were then mixed with the diluted blood suspension (100 microliters). The mixtures were then incubated at 37° C. for 1 hour to allow for the interactions between rRBC and the polymers to take place. After that, the mixture was subjected to centrifugation (1000 g-force for 5 minutes, 4° C.), and 100 microliter aliquots of the supernatant were pipetted into a 96-well microplate. The hemoglobin release was measured spectrophotometrically by measuring the absorbance of the samples at 576 nm using the microplate reader (TECAN, Switzerland). Two control groups were employed for this assay: untreated rRBC suspension (negative control), and rRBC suspension treated with 0.1% TRITON-X (positive control). Each assay was performed in 4 replicates. The percentage of hemolysis was defined as follows: Hemolysis (%)=[($OD_{576nm}$ of the treated sample—$OD_{576nm}$ of the negative control)/($OD_{576nm}$ of positive control—$OD_{576nm}$ of negative control)]×100%. The results are reported in Table 3.

Table 3 summarizes the antimicrobial activity (MIC), HC50, and HC50 Selectivity of the cationic polymers. Gm is the geometric mean of the MICs across the spectrum of microbes tested. "N.D." means not determined.

TABLE 3

| Example | Polymer Name | Cationic Group | Spacer Group | DP | MIC (mg/L) S. aureus | E. coli | P. aeruginosa | C. albicans | Gm (mg/L) | HC50 (mg/L[1]) | Selectivity (HC50/Gm) |
|---|---|---|---|---|---|---|---|---|---|---|---|
| 19 | PC2G-20 | G | 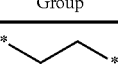 | 20 | 7.8 | 15.6 | 15.6 | 15.6 | 13.7 | >8000[a] | >584 |
| 20 | PC2G-5 | G | 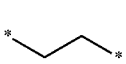 | 5 | 15.6 | 15.6 | 62.5 | 62.5 | 39.1 | >8000[a] | >205 |
| 21 | PC2G-10 | G | 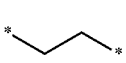 | 10 | 7.8 | 7.8 | 15.6 | 31.3 | 15.6 | >8000[a] | >513 |
| 22 | PC2G-40 | G | 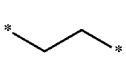 | 40 | 31.3 | 15.6 | 15.6 | 31.3 | 23.5 | >8000[a] | >340 |
| 23 | PC3G-20 | G | 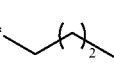 | 20 | 7.8 | 7.8 | 15.6 | N.A. | N.A. | >8000 | N.A. |
| 24 | PC4G-20 | G | 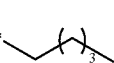 | 20 | 7.8 | 7.8 | 15.6 | N.A. | N.A. | >8000 | N.A. |
| 25 | PC5G-20 | G | 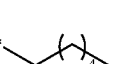 | 20 | 7.8 | 7.8 | 15.6 | 15.6 | 11.7 | 62.5 | 5.3 |
| 26 | PiPrG-10 | D | 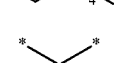 | 10 | 31.3 | >500 | >500 | N.D. | N.D. | >8000 | N.D. |
| 27 | PCyG-20 | G |  | 20 | 3.9 | 3.9 | 31.3 | N.D. | N.D. | 125 | N.D. |
| 28 | PPhG-20 | G |  | 20 | 62.5 | 125 | 125 | N.D. | N.D. | 8000 | N.D. |
| 29 | PBnG-20 | G | 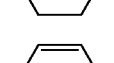 | 20 | 62.5 | 125 | 125 | N.D. | N.D. | 500 | N.D. |
| 30 | PC2Tu-20 | I | 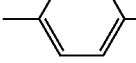 | 20 | 31.3 | 31.3 | 62.5 | N.D. | N.D. | 250 | N.D. |

[a]At the highest concentration tested extent of hemolysis was <5%.

The Table 3 results demonstrate broad-spectrum high activity by these cationic polymers. The effect of molecular weight of the cationic polymer can be seen by comparing the MICs of Examples 19-22. A DP of 10 to 20 was most favorable in lowering the MIC against the various microbes tested, with an average DP of 20 giving the lowest geometric mean (Gm) values of the MIC. The MIC against *C. albicans* decreased four-fold (62.5 mg/L to 15.6 mg/L) from DP from 5 to 20. Similar behavior was observed for the highly opportunistic *P. aeruginosa*, whose MIC decreased four-fold from 62.5 mg/L to 15.6 mg/L as the DP increased from 5 to 10. The MICs of Table 3 are generally lower (i.e., indicating more toxic to microbes) compared to previous cationic polycarbonate systems bearing quaternary ammonium groups as the pendent cationic groups.

Table 3 also shows that all of the polymers possessed a pronounced lack of toxicity towards RBCs (HC50 >8000 mg/L) regardless of their respective molecular weight. Even at the highest concentration tested (i.e., 8000 mg/L), the polymers did not incite observable hemolysis (<5%). These are believed to be the highest HC50 values reported for biodegradable synthetic polymers. As a consequence of its high HC50 value, the selectivity (HC50/Gm) observed for the best polymer candidate, PC2G-20, was more than 584, which is significantly higher in comparison to values reported for host defense peptides (e.g., cecropins, magainins, and defensins).

Table 3 also demonstrates the influence of the hydrophobic spacer group (i.e., homologous straight chain $C_2$-$C_5$ alkyl, cyclohexyl, phenyl, and benzyl spacer groups). For the homologous straight chain alkyl series, while there was no significant difference in terms of the respective antimicrobial activity across the microbes tested, the hemolytic activity increased by more than 128 times from >8000 mg/L (for PC2G-20, PC3G-20 and PC4G-20) to 62.5 mg/L for PC5G-20. A higher HC50 value is desirable. Without being bound by theory, the increase in hemolytic activity towards mammalian erythrocytes might be largely due to the increase in the polymer's hydrophobicity with increasing chain length.

The effect of doubling the guanidinium groups per repeat unit at half the DP is demonstrated by cationic polymer PiPrG-10. PiPrG-10 contains the same number of guanidinium groups as PC2G-20 but has a shorter chain length. Although potent against Gram-positive *S. aureus* and virtually non-hemolytic at more than 8000 mg/L, PiPrG-10 was found to be inactive against the Gram-negative bacteria, which is believed to be related to the reduced spacing as well as flexibility of the guanidinium groups along the polymeric chain.

Table 3 also demonstrates the effect of the cyclic groups on antimicrobial activity. While the cyclohexyl-containing polymer PCyG-20 was demonstrated to be more potent than PPhG-20, PCyG-20 was also significantly more hemolytic (125 mg/L vs. 8000 mg/L). Addition of a single methylene group to the aromatic ring (PBnG-20) also resulted in a substantial increase in hemolytic activity (HC50=500 mg/L).

From the Table 3 results, PC2G-20 had the highest selectivity. The structural analogue PC2Tu-20 contains an isothiouronium moiety as the pendent cationic group. While not as potent as its respective guanidinium analogue PC2G-20, the isothiouronium-polymer PC2Tu-20 nevertheless exhibited reasonably potent activity against the same spectrum of clinically relevant bacterial strains (i.e., S. aureus, E. coli and P. aeruginosa). However, the hemolytic activity of PC2Tu-20 was significantly higher (250 mg/L versus >8000 mg/L).

Cytotoxicity (MTT) Assay

Cytotoxicity of the representative polymers to the human embryonic kidney (HEK) 293 cell line was quantified by the MTT colorimetric assay. Confluent HEK 293 cells in culture were trypsinized and seeded onto 96 well-plates at a density of 20,000 cells/well in Dulbecco's Modified Eagle Medium (DMEM) supplemented with 10% fetal bovine serum (FBS) and 1% penicillin-streptomycin, and incubated for 24 hours at 37° C. and 5% $CO_2$. The cell culture medium was replaced with 100 microliters of polymer solution at various concentrations (2000, 1000, 500, 250, 125, 62.5, 31.25 and 15.625 mg/L). Cell viability was measured at 6 hours and 24 hours post-addition of polymer-containing medium using MTS assay (CellTiter 96® Aqueous One Solution Cell Proliferation Assay, Promega, Madison, Wis., U.S.A.) according to the manufacturer's instructions. Accordingly, 20 microliters of Aqueous One Solution was added to each well, and incubated for 1-2 hours at 37° C. to allow color development due to formation of soluble formazan. The absorbance was recorded at 490 nm. Cell viability was calculated as [A490 of polymer treated wells/A490 of untreated control wells]×100, where A490 is the absorbance at 490 nm. The polymer concentration which caused 50% reduction in cell viability after 6 hours or 24 hours of incubation was defined as the IC50 value.

Figure 7:
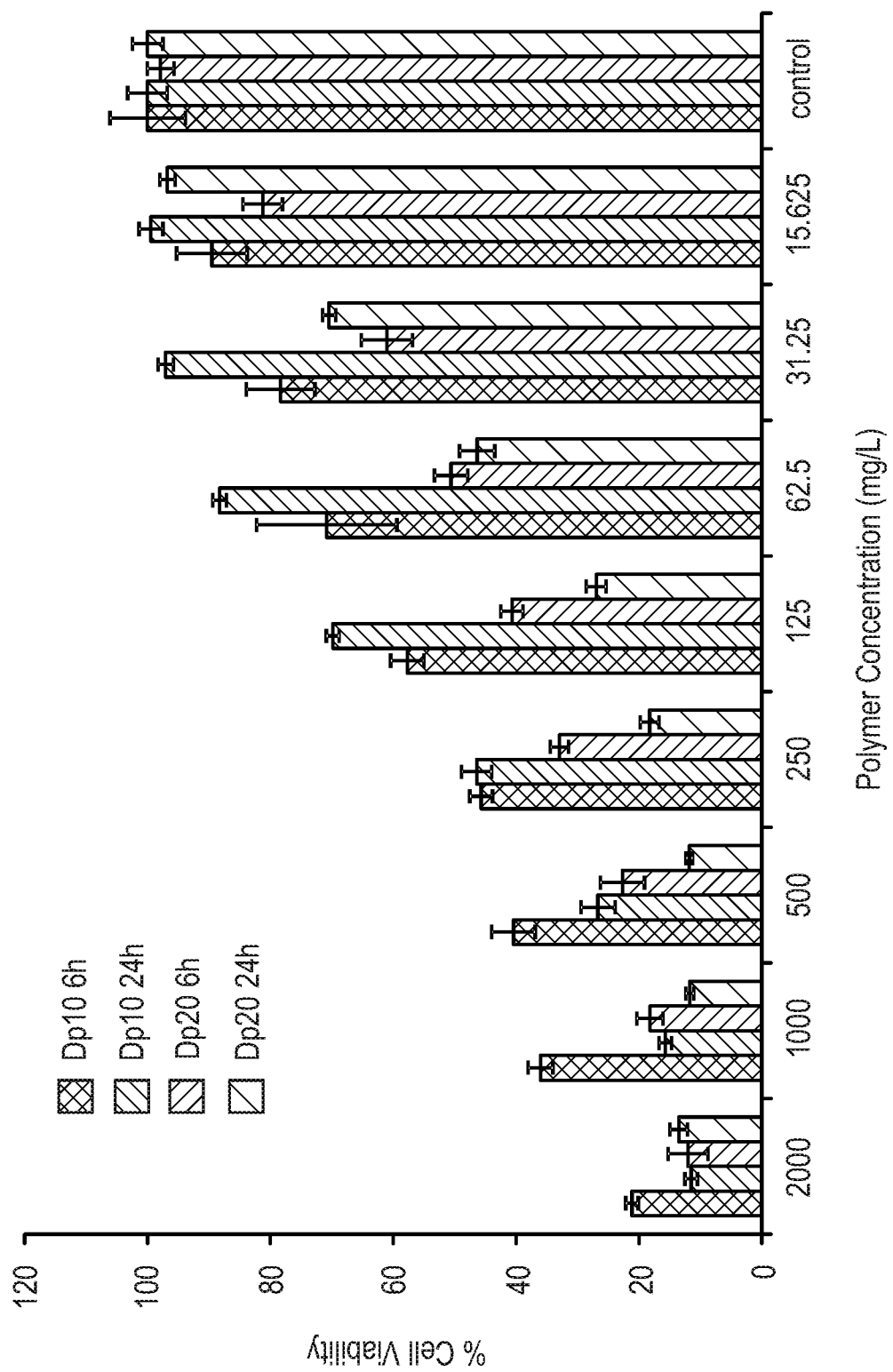
FIG. 7 is a bar graph showing human embryo kidney (HEK) 293 cell viability when incubated for 6 hours and 24 hours with PC2G-10 and PC2G-20 at various concentrations. PC2G-10 is labeled "Dp10" in the legend, and PC2G-20 is labeled "Dp20" in the legend.

FIG. 7 is a bar graph showing the HEK 293 cell viability when incubated for 6 hours and 24 hours with PC2G-10 ("Dp10" in the graph) and PC2G-20 ("Dp20" in the graph) at various concentrations. PC2G-10 and PC2G-20 have a noticeable toxic effect on HEK 293 cell lines, particularly at higher concentrations. Such extent of toxicity might well be anticipated owing to the high cationic charge density of the polymers. Notwithstanding their apparent toxicity, as a consequence of their relatively potent activity against the microbes at much lower concentrations, these polymers are still considered to be selective (IC50/Gm=5 to 16) and useful for potential clinical applications. In addition, it is noteworthy to highlight an observable dependency of the polymer molecular weight on the extent of cytotoxicity. By comparing the IC50 values of the respective polymers (for PC2G-10, IC50=250 micrograms/mL; for PC2G-20, IC50=62.5 micrograms/mL), it can be seen that the higher DP corresponds to a relatively pronounced toxicity.

Antibacterial Activity of Guanidinium-Functionalized Silica Particles

The antibacterial activity of the guanidinium monomer-modified silica particles APSi-C2G, APSi-C4G, and APSi-C6G was tested against S. aureus, E. coli and P. aeruginosa. First, the bacterial sample was inoculated in MHB at 37° C. with constant shaking at 100 rpm for overnight in order to ensure that they entered the log growth phase. After overnight incubation, the concentration of the bacterial sample was adjusted to give an initial optical density (OD) reading of 0.07 in a 96-well plate measured at a wavelength of 600 nm using a microplate reader (Tecan Group Ltd.; Männedorf, Switzerland), which corresponds to the concentration of McFarland 1 solution ($3 \times 10^8$ CFU/mL). The bacterial sample was further diluted to achieve an initial loading of $3 \times 10^5$ CFU/mL. After that, 100 microliters of the bacterial sample was added to each well of a 96-well plate, in which 100 microliters of surface-coated silica particles of various concentrations was placed. The samples were then incubated at 37° C. with constant shaking at 100 rpm. After 18 hours, 10 microliters of the supernatant was extracted from each well, serially diluted in MHB and plated onto an agar plate. Finally, the agar plates were incubated at 37° C. for 18 hours, and the number of CFUs was counted and compared with the control (bacteria incubated without silica particles). Each test was performed in triplicate.

Figure 8:
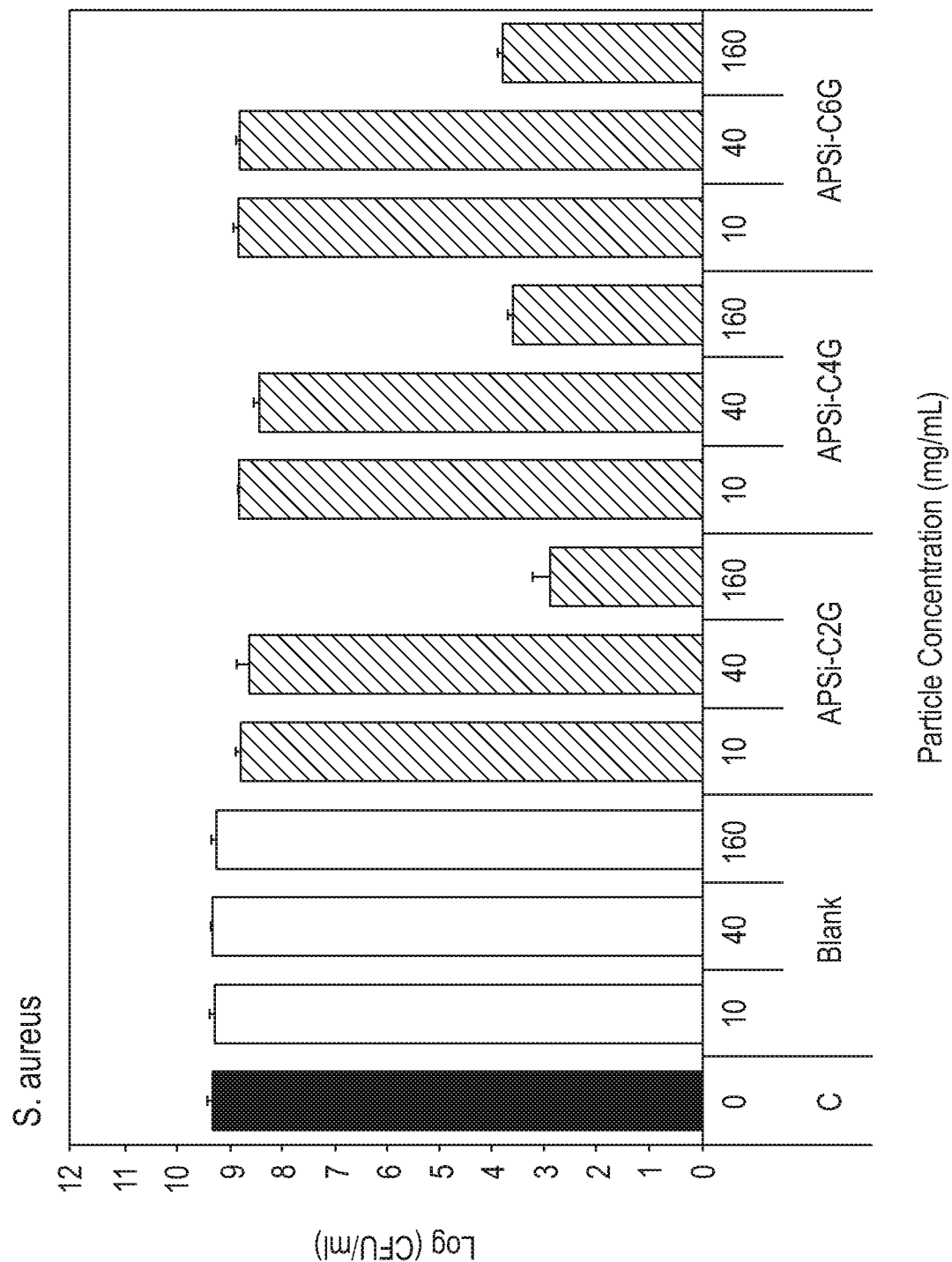
FIG. 8 is a bar graph showing the number of remaining viable Staphylococcus aureus (S. aureus) colonies incubated with varying amounts of APSi-C2G, APSi-C4G, and APSi-C6G particles.
Figure 9:
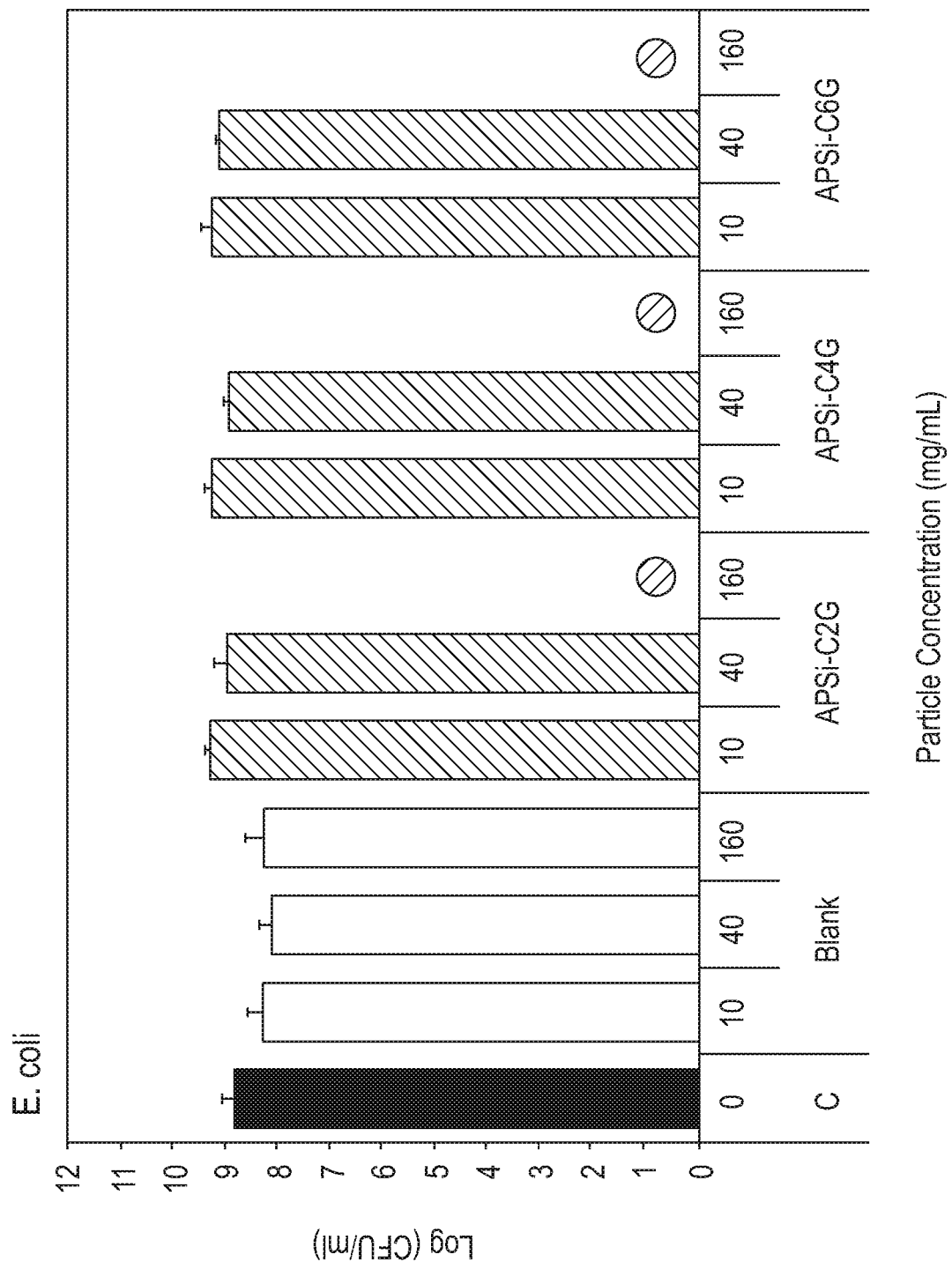
FIG. 9 is a bar graph showing the number of remaining viable Escherichia coli (E. coli) colonies incubated with varying amounts of APSi-C2G, APSi-C4G, and APSi-C6G particles.
Figure 10:
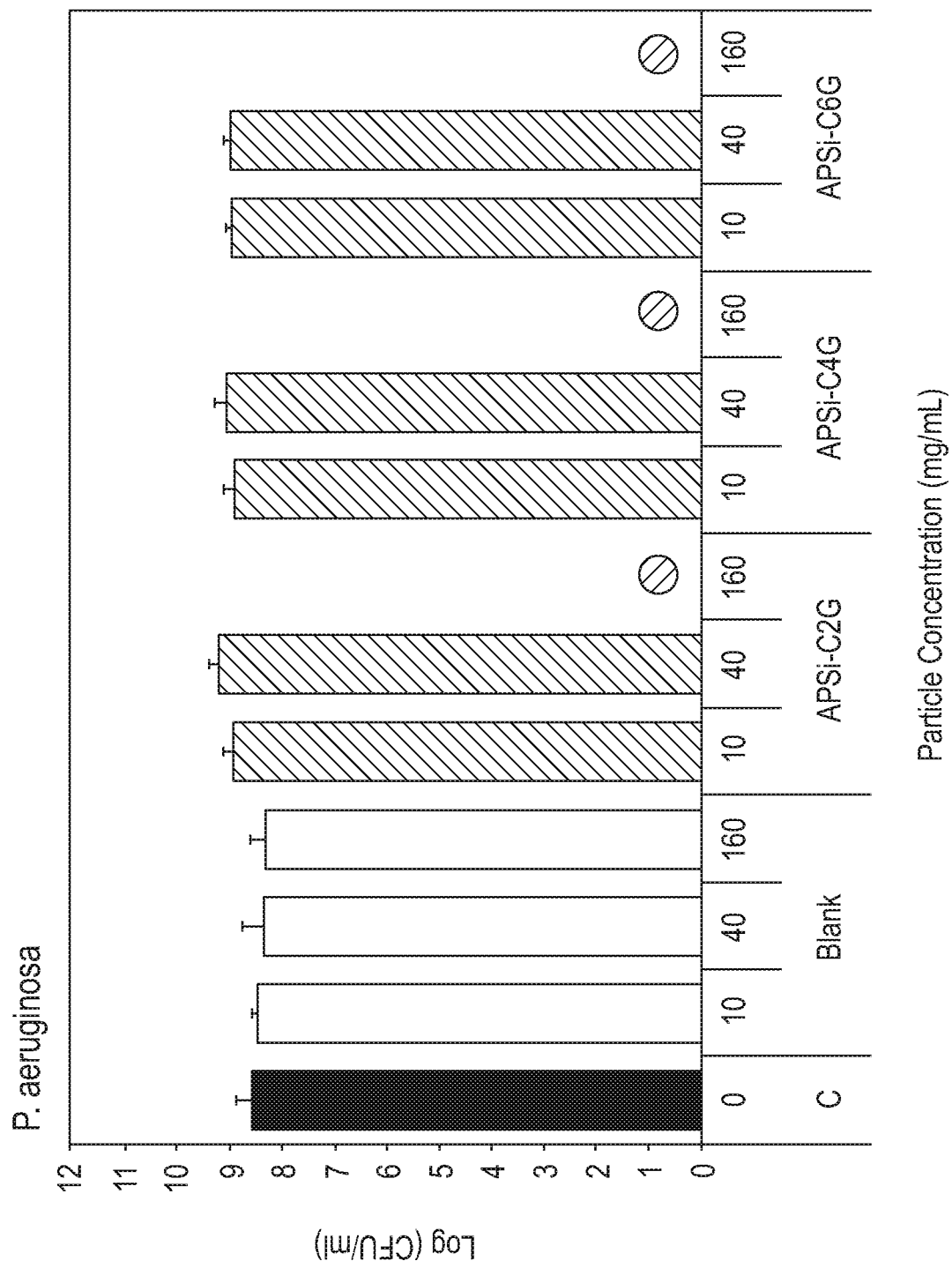
FIG. 10 is a bar graph showing the number of remaining viable Pseudomonas aeruginosa (P. aeruginosa) colonies incubated with varying amounts of APSi-C2G, APSi-C4G, and APSi-C6G particles.

FIGS. 8 to 10 show the number of remaining viable bacterial colonies incubated with varying amounts of guanidinium monomer-modified silica particles APSi-C2G, APSi-C4G, and APSi-C6G particles. By comparing the different alkyl spacers (n=2, 4 and 6) of the monomers, the surface-coated silica particles showed comparable antibacterial efficiency against S. aureus, E. coli and P. aeruginosa. All the three different samples achieved more than three-logarithm reduction (99.9% kill) in S. aureus colonies at 160 mg/mL (FIG. 8), while eliminating E. coli and P. aeruginosa colonies completely at the same concentration (FIGS. 9 and 10, respectively).

Figure 11:
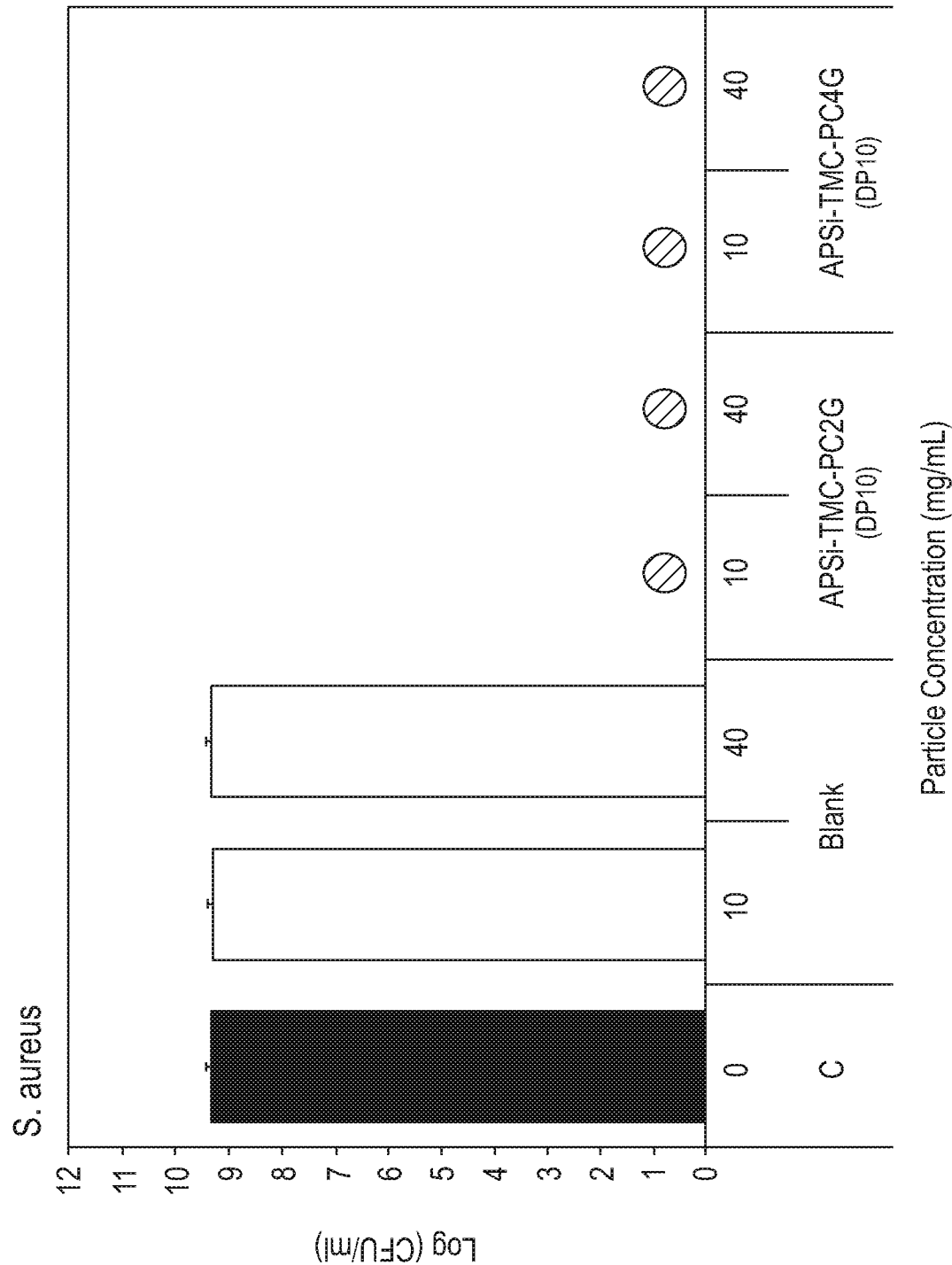
FIG. 11 is a bar graph showing the antibacterial activity of the guanidinium polymer-modified silica particles APSi-TMS-PC2G and APSi-TMS-PC4G against S. aureus. The control experiment (black column) was conducted by having a cell suspension without silica particles. Patterned circle indicates no colony observed. The data correspond to mean±standard deviation (n=3).
Figure 12:
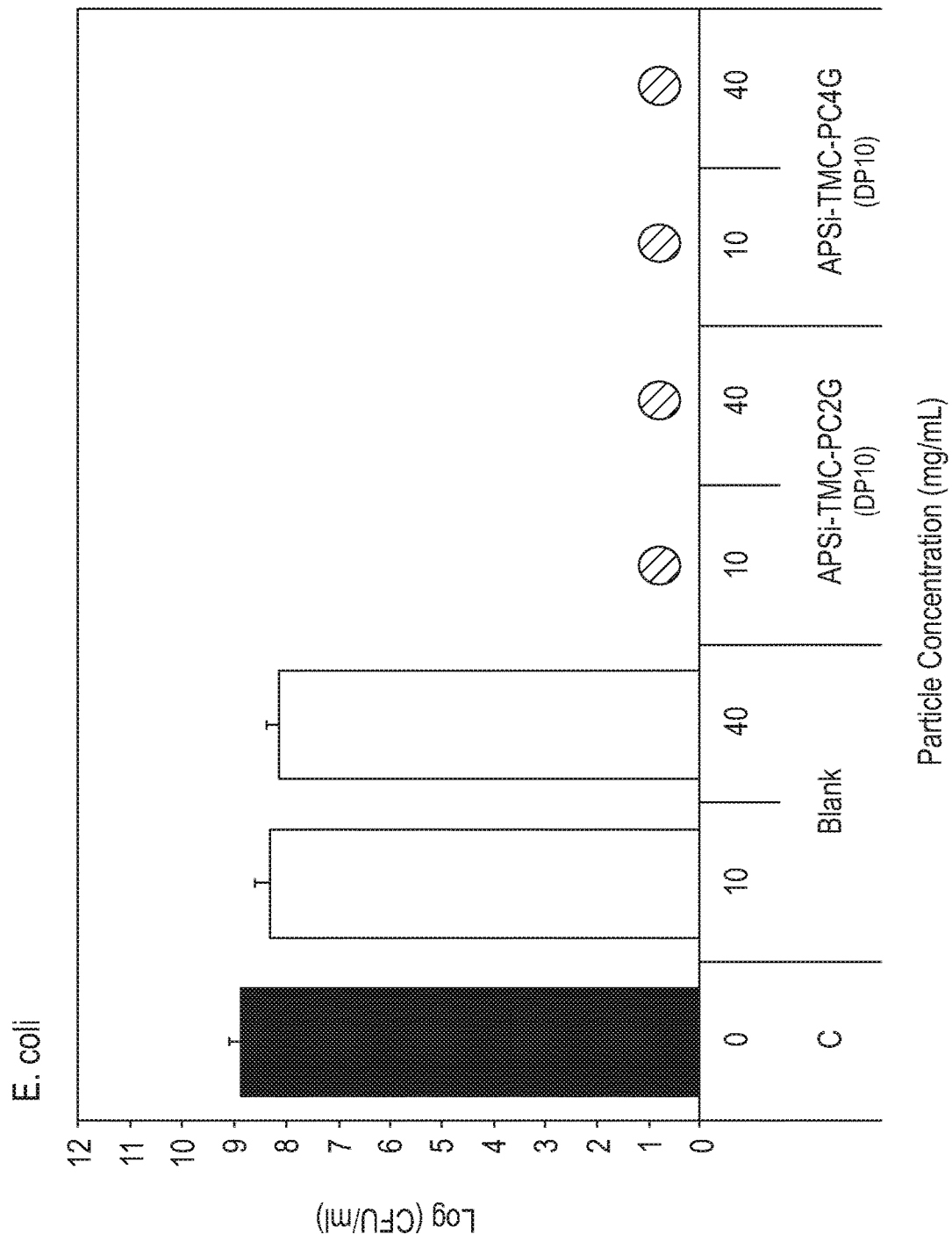
FIG. 12 is a bar graph showing the antibacterial activity of the guanidinium polymer-modified silica particles APSi-TMS-PC2G and APSi-TMS-PC4G against E. coli. The control experiment (black column) was conducted by having a cell suspension without silica particles. Patterned circle indicates no colony observed. The data correspond to mean±standard deviation (n=3).
Figure 13:
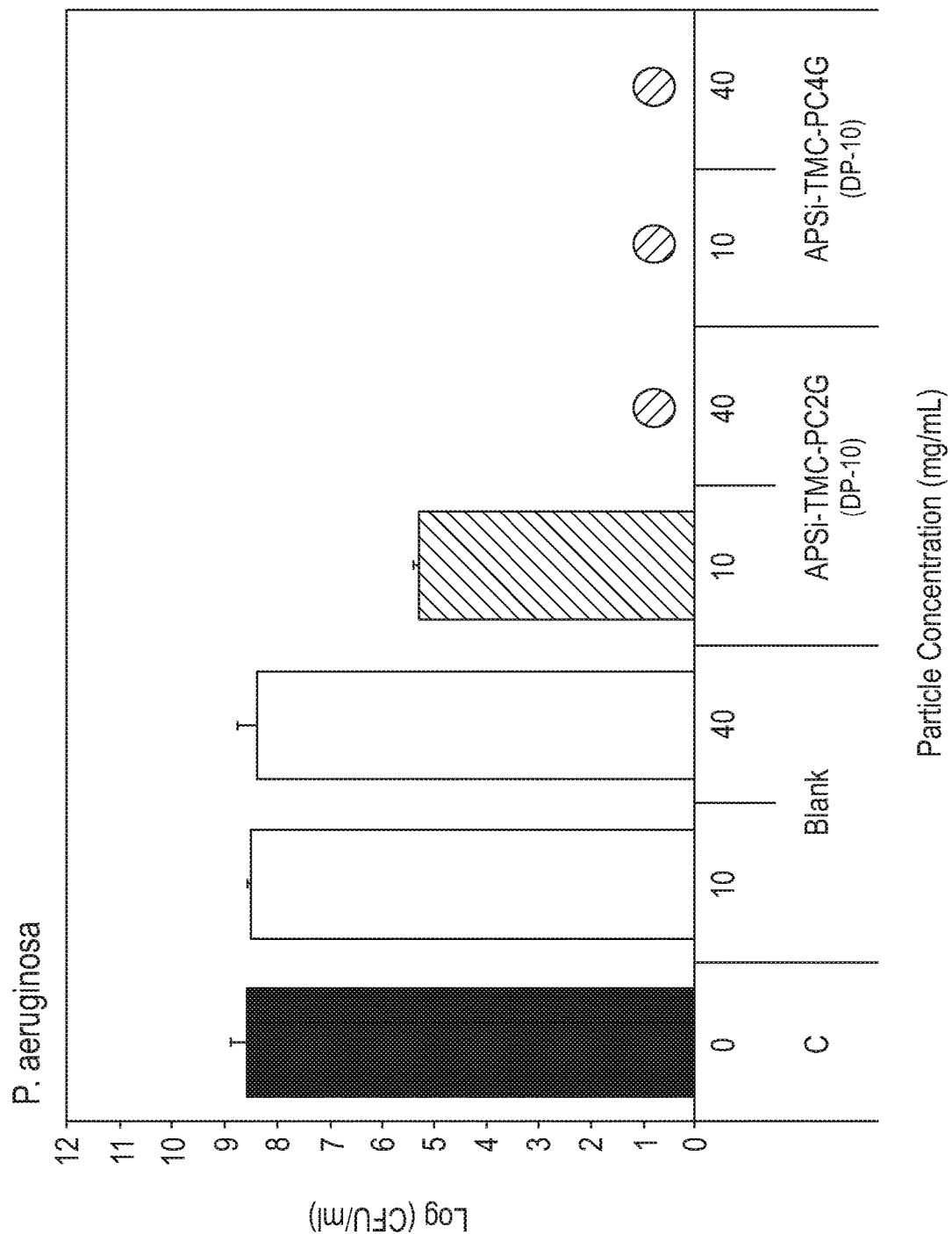
FIG. 13 is a bar graph showing the antibacterial activity of the guanidinium polymer-modified silica particles APSi-TMS-PC2G and APSi-TMS-PC4G against P. aeruginosa. The control experiment (black column) was conducted by having a cell suspension without silica particles. Patterned circle indicates no colony observed. The data correspond to mean±standard deviation (n=3).

FIG. 11 to 13 are bar graphs showing the antibacterial activity of the guanidinium polymer-modified silica particles APSi-TMS-PC2G (Example 35) and APSi-TMS-PC4G (Example 36) against S. aureus, E. coli and P. aeruginosa, respectively. Each of the polymer-coated silica particles eradicated S. aureus and E. coli completely at 10 mg/mL (FIGS. 11 and 12, respectively). Moreover, the APSi-TMS-PC2G particles achieved more than three-logarithm reduction (99.9% kill) in P. aeruginosa colonies at 10 mg/mL, while eliminating the colonies at a higher particle concentration of 40 mg/mL (FIG. 13). However, the surface-grafted polymer with the butyl spacer APSi-TMS-PC4G eradicated P. aeruginosa colonies completely at a low particle concentration of 10 mg/mL. Overall, the APSi-TMS-PC4G particles exhibited higher antibacterial efficacy than APSi-TMS-PC2G particles, possibly due to the higher hydrophobicity of the butyl spacer compared to the ethyl spacer in the surface-grafted polymer. Also, the polymer-coated silica particles had greater antibacterial efficacy against the bacteria compared to the monomer-coated silica particles.

Figure 14:
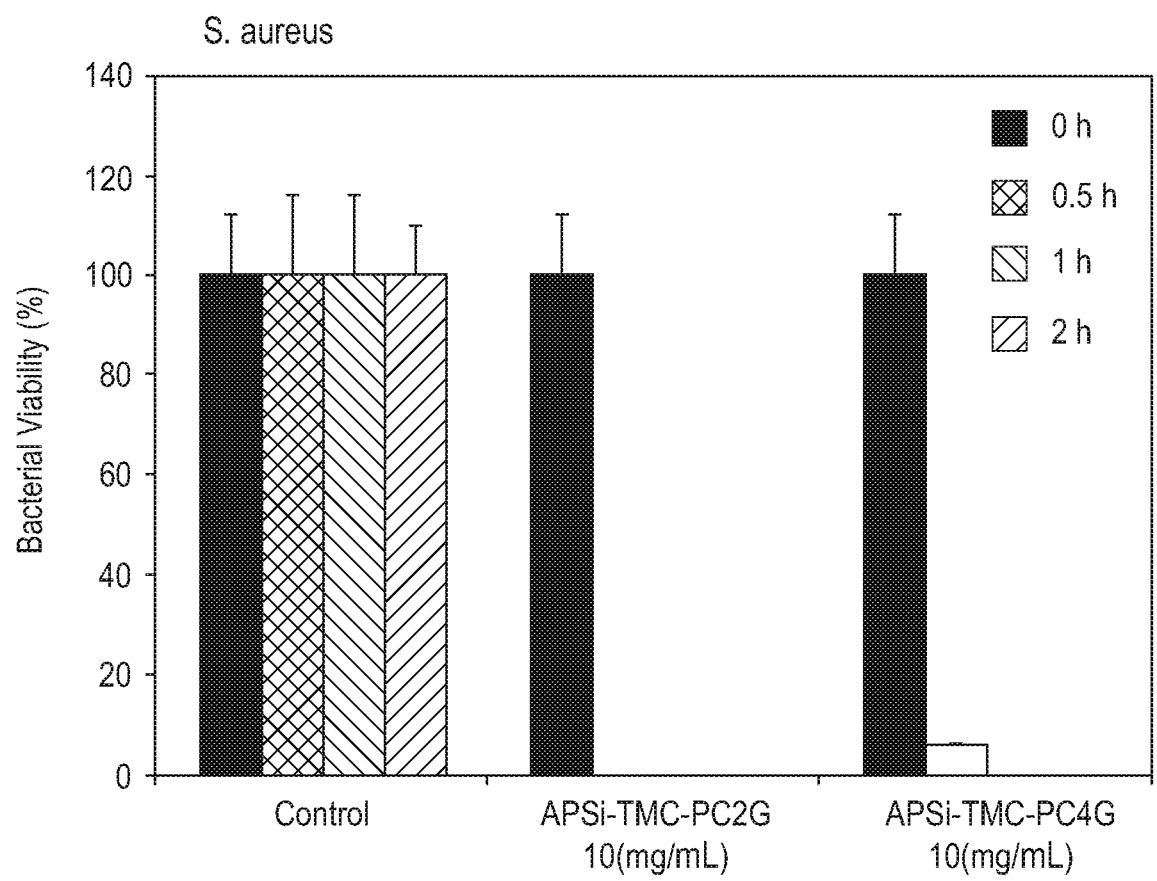
FIG. 14 is a bar graph showing the killing kinetics of APSi-TMS-PC2G and APSi-TMS-PC4G against S. aureus. At various time points, an aliquot of the medium serially diluted was plated onto agar plates to assess microorganism survival. The bacterial viability of cells incubated with polymer-coated silica particles was normalized with respect to the control at the respective time points. The data correspond to mean±standard deviation (n=3).
Figure 15:
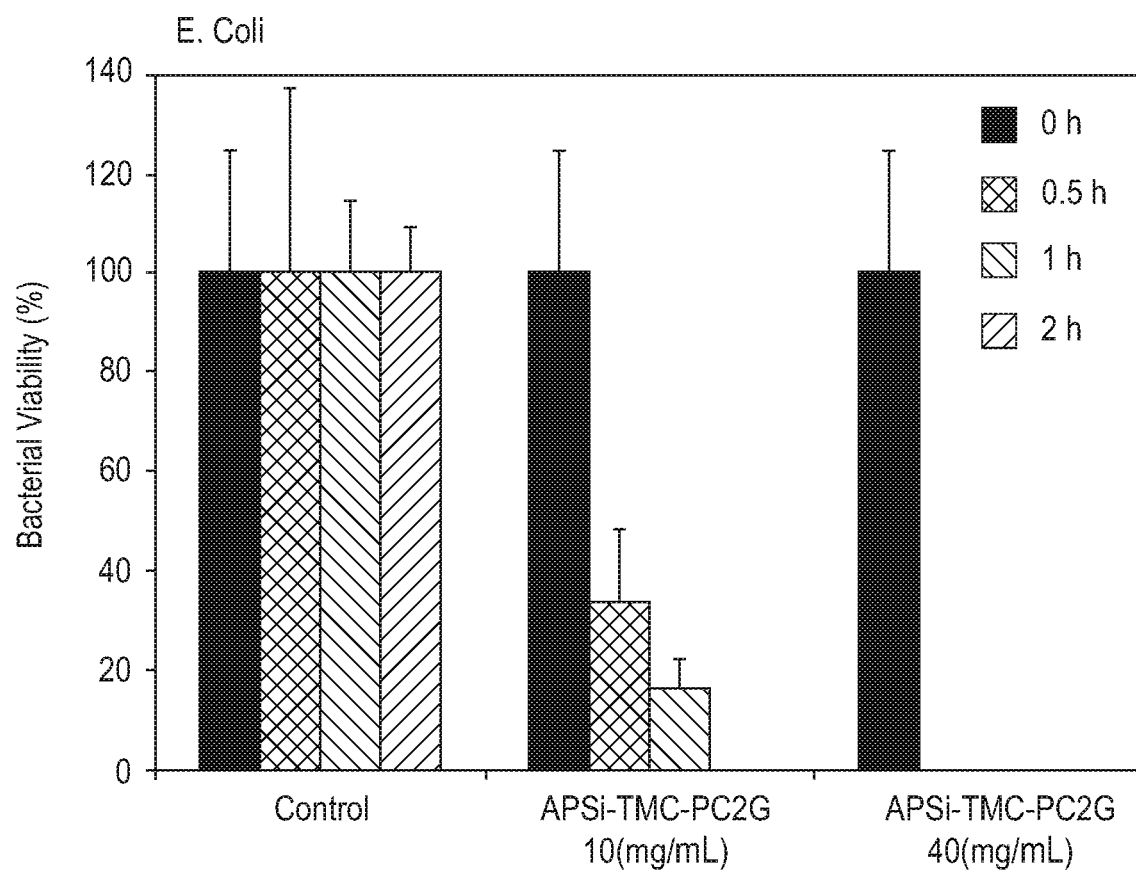
FIG. 15 is a bar graph showing the killing kinetics of APSi-TMS-PC2G against E. coli. At various time points, an aliquot of the medium serially diluted was plated onto agar plates to assess microorganism survival. The bacterial viability of cells incubated with polymer-coated silica particles was normalized with respect to the control at the respective time points. The data correspond to mean±standard deviation (n=3).
Figure 16:
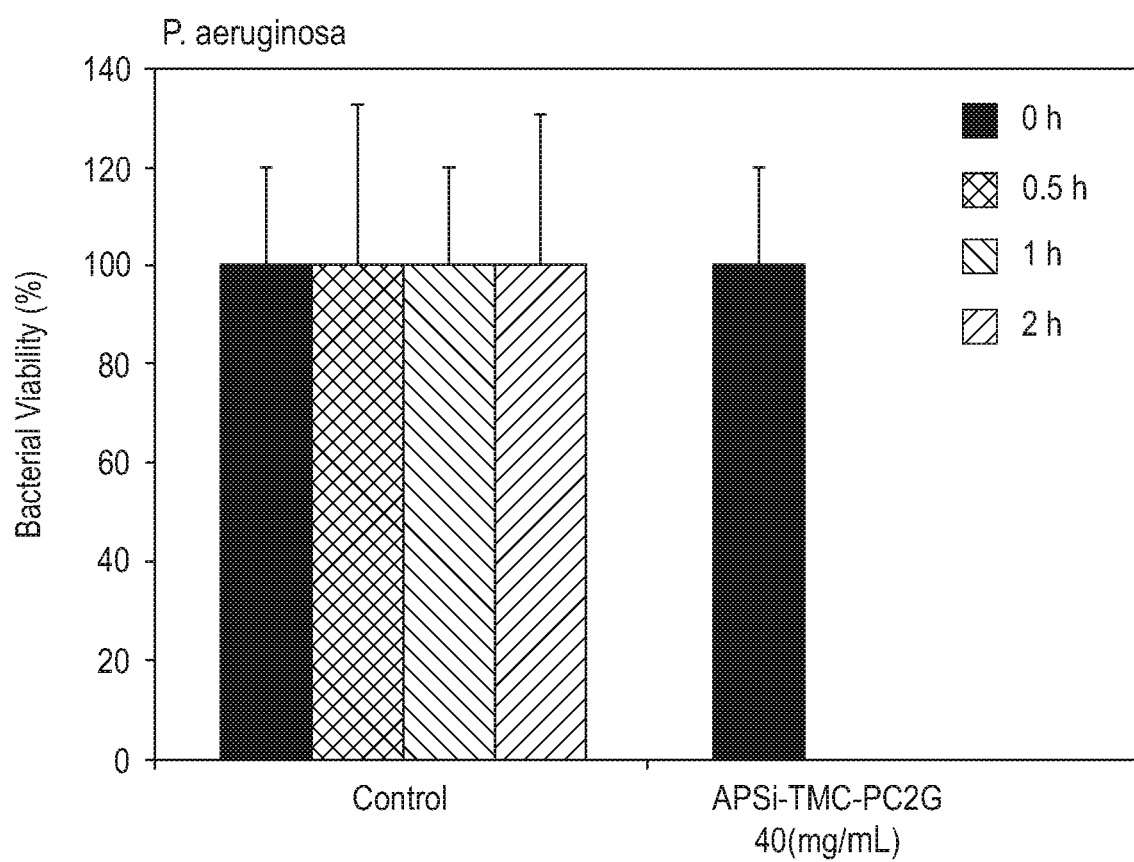
FIG. 16 is a bar graph showing the killing kinetics of APSi-TMS-PC2G against P. aeruginosa. At various time points, an aliquot of the medium serially diluted was plated onto agar plates to assess microorganism survival. The bacterial viability of cells incubated with polymer-coated silica particles was normalized with respect to the control at the respective time points. The data correspond to mean±standard deviation (n=3).

FIG. 14-17 (bar graphs) characterize the killing kinetics of guanidinium polymer-modified silica particles APSi-TMS-PC2G (Example 35) and/or APSi-TMS-PC4G (Example 36) incubated with (a) S. aureus, (b) E. coli and (c) P. aeruginosa suspension ($3 \times 10^5$ CFU/mL), respectively. At various time points, an aliquot of the medium serially diluted was plated onto agar plates to assess microorganism survival. The bacterial viability of cells incubated with polymer-coated silica particles was normalized with respect to the control at the respective time points. The data correspond to mean±standard deviation (n=3). In FIG. 14, at a particle concentration of 10 mg/mL, APSi-TMS-PC2G and APSi-TMS-PC4G showed similar killing kinetics against *S. aureus*, eradicating the bacterial colonies almost completely within 30 minutes. In FIG. 15 shows the killing kinetics of APSi-TMS-PC2G against *E. coli*. At a particle concentration of 10 mg/mL, APSi-TMS-PC2G eradicating the *E. coli* colonies almost completely after 1 hour. At a particle concentration of 40 mg/mL, APSi-TMS-PC2G eradicated *E. coli* completely within 30 minutes. FIG. 16 shows the killing kinetics of APSi-TMS-PC2G against *P. aeruginosa*. At a particle concentration of 40 mg/mL, APSi-TMS-PC2G eradicated *P. aeruginosa* completely within 30 minutes.

Figure 17:
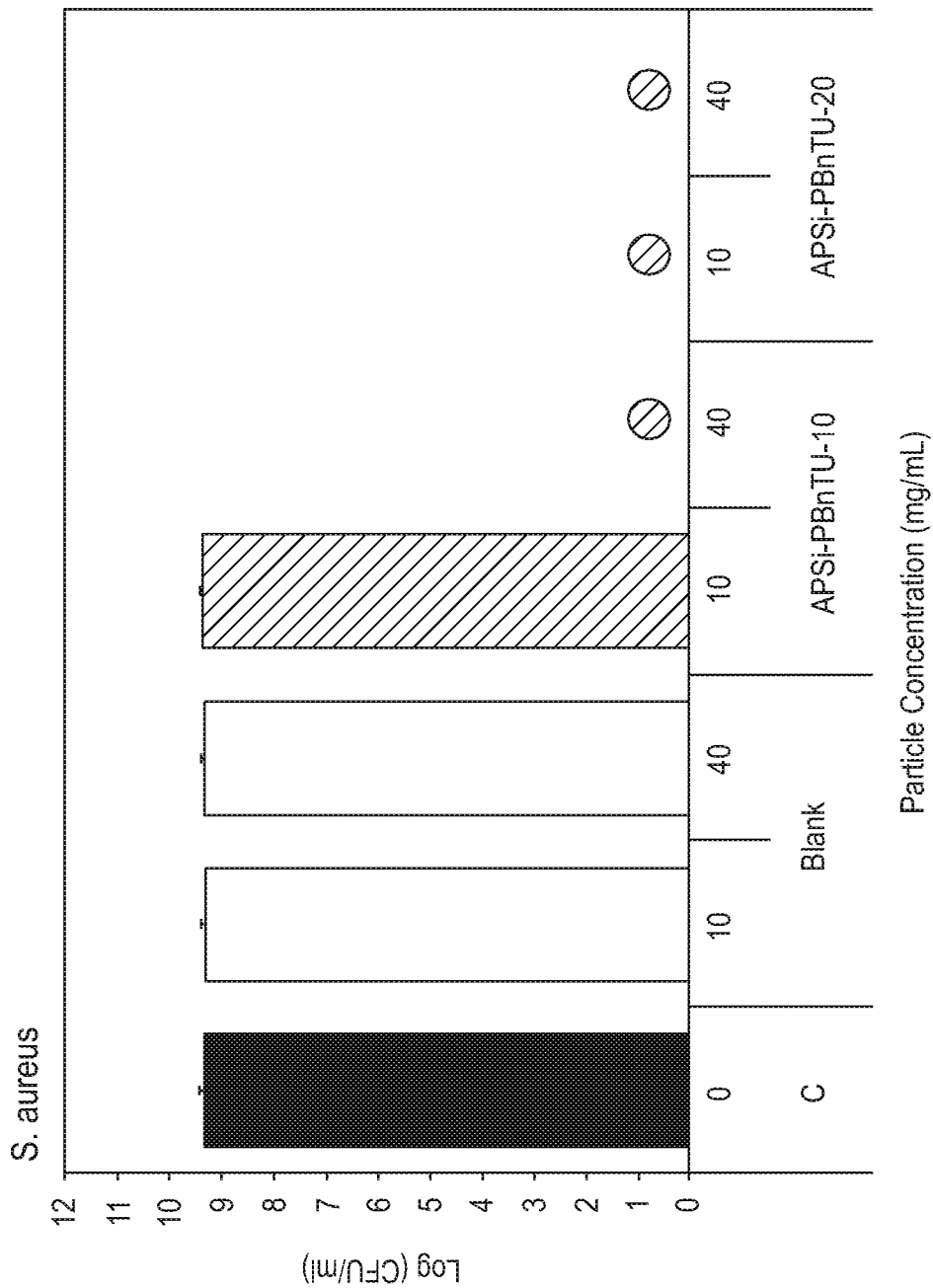
FIG. 17 is a bar graph showing the antibacterial efficacy of various amounts APSi-PBnTU-10 and APSi-PBnTu-20 particles incubated with a suspension of S. aureus ($3 \times 10^5$ CFU/mL) at 37° C. for 18 hours. The control experiment (black column) was conducted by having a cell suspension without silica particles. Patterned circle indicates no colony observed. The data correspond to mean±standard deviation (n=3).
Figure 18:
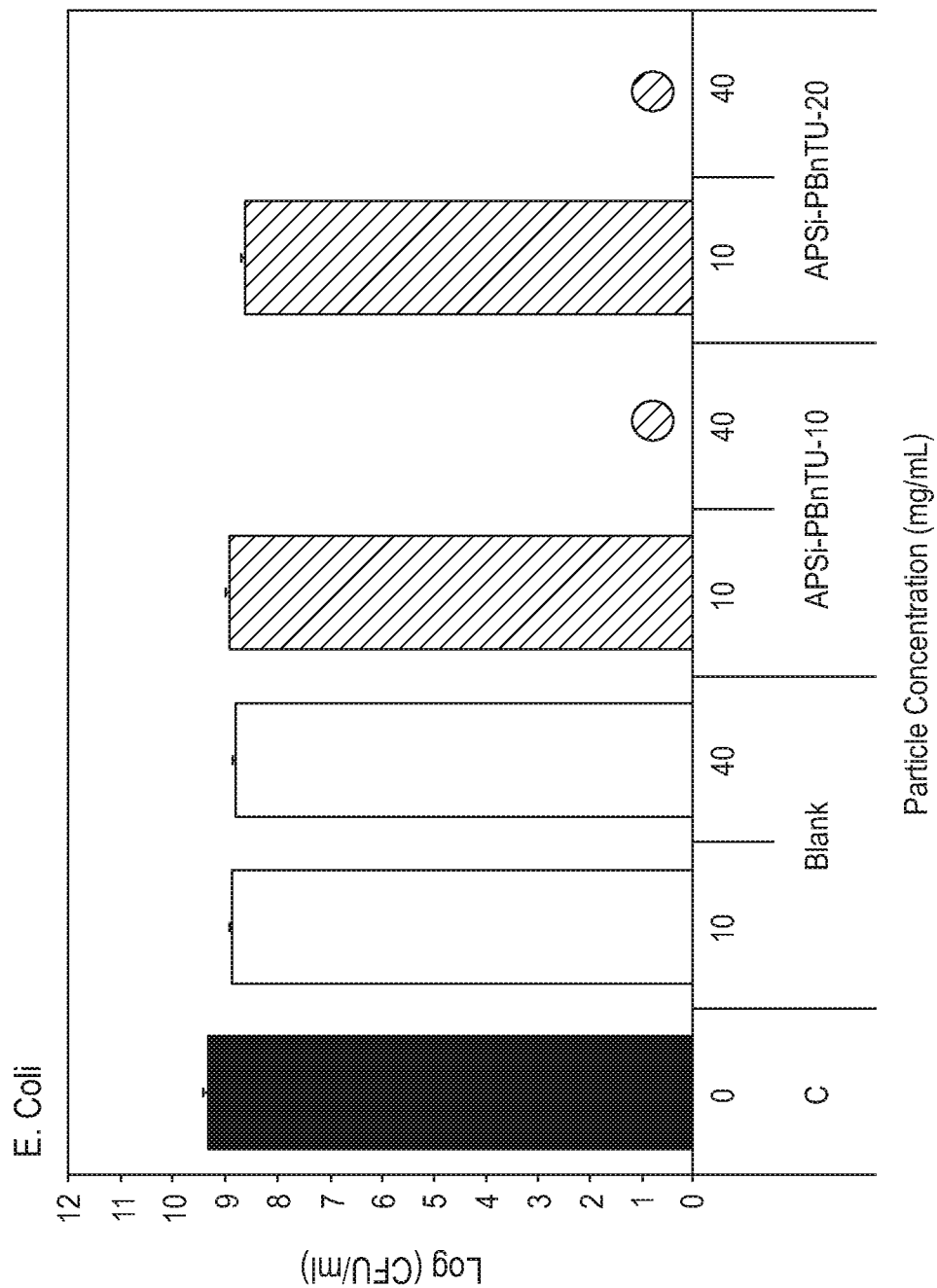
FIG. 18 is a bar graph showing the antibacterial efficacy of various amounts APSi-PBnTU-10 and APSi-PBnTu-20 particles incubated with a suspension of E. coli ($3 \times 10^5$ CFU/mL) at 37° C. for 18 hours. The control experiment (black column) was conducted by having a cell suspension without silica particles. Patterned circle indicates no colony observed. The data correspond to mean±standard deviation (n=3).
Figure 19:
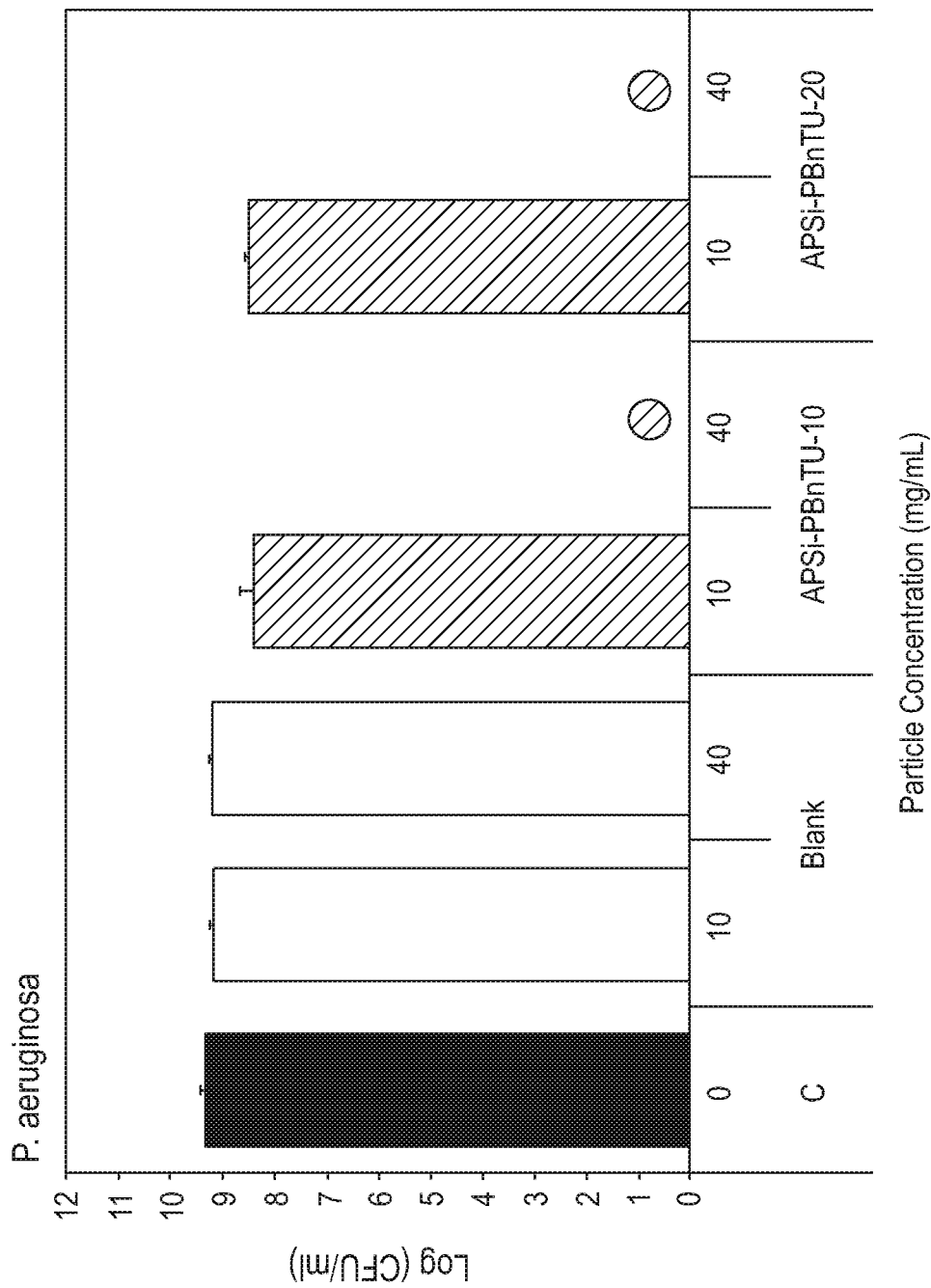
FIG. 19 is a bar graph showing the antibacterial efficacy of various amounts APSi-PBnTU-10 and APSi-PBnTu-20 particles incubated with a suspension of P. aeruginosa ($3 \times 10^5$ CFU/mL) at 37° C. for 18 hours. The control experiment (black column) was conducted by having a cell suspension without silica particles. Patterned circle indicates no colony observed. The data correspond to mean±standard deviation (n=3).
Figure 20:
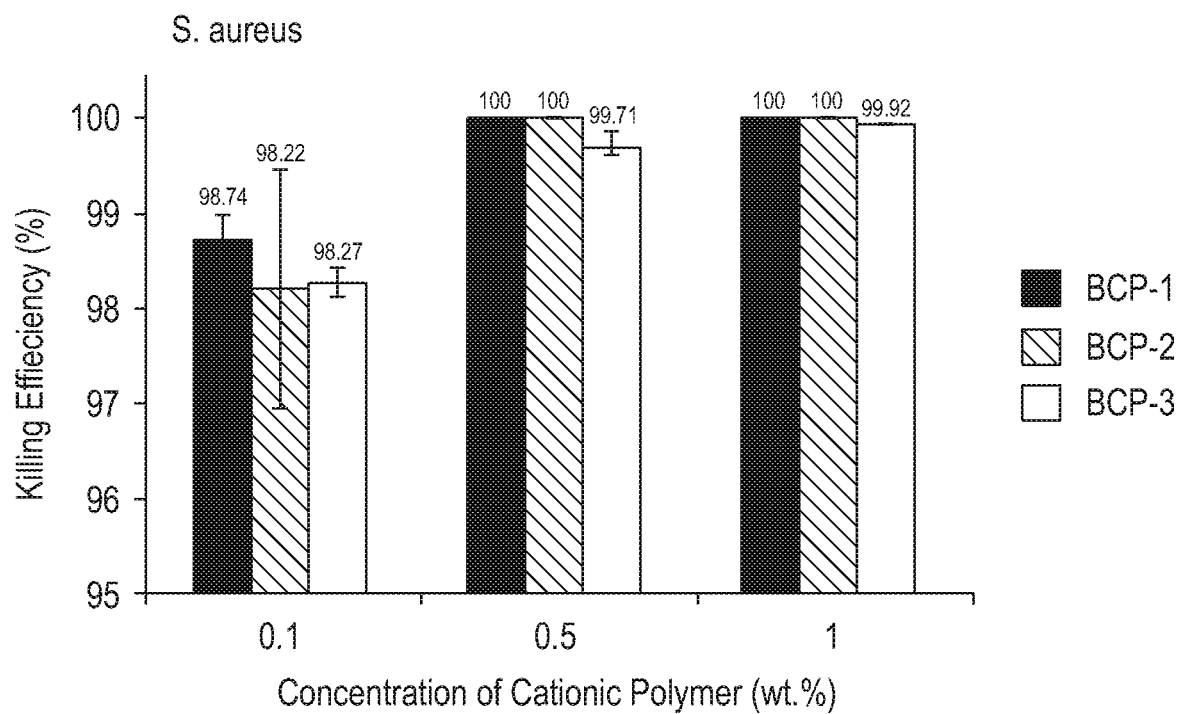
FIG. 20 is a bar graph showing the killing efficiency against S. aureus of block copolymer hydrogels containing a mixture of antimicrobial block copolymer BCP-1, BCP-2, or BCP-3 and triblock copolymer TBP-1.
Figure 21:
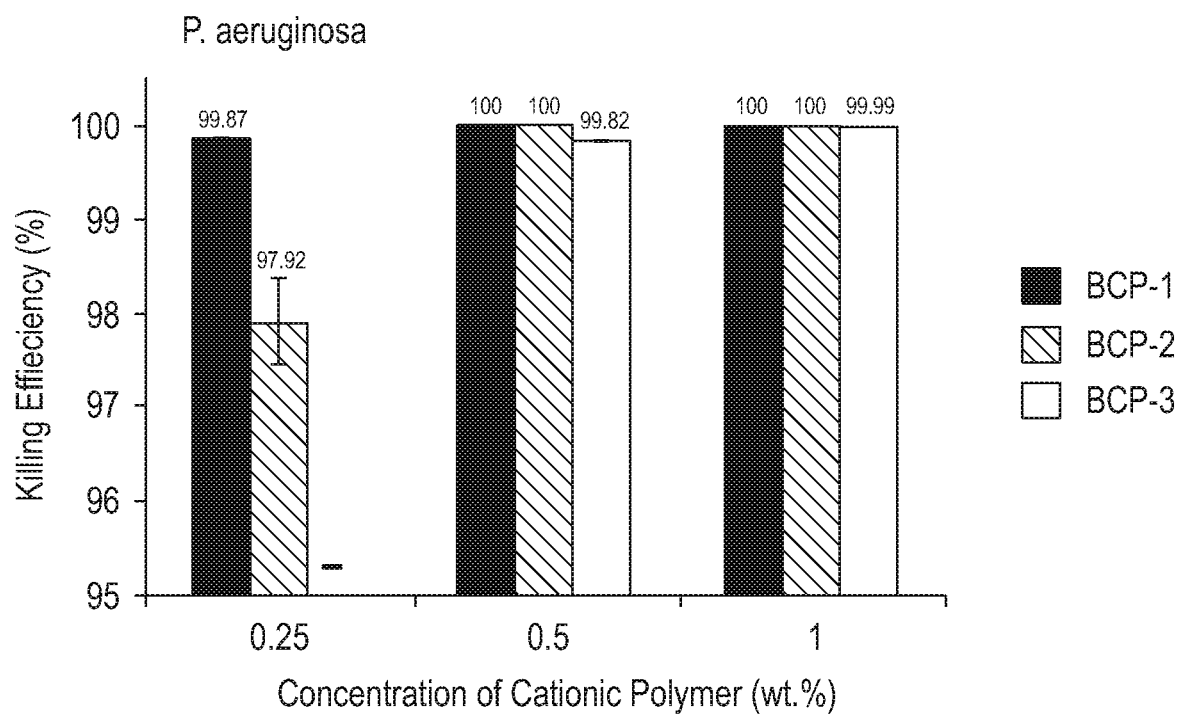
FIG. 21 is a bar graph showing the killing efficiency against P. aeruginosa of block copolymer hydrogels containing a mixture of antimicrobial block copolymer BCP-1, BCP-2, or BCP-3 and triblock copolymer TBP-1.
Figure 22:
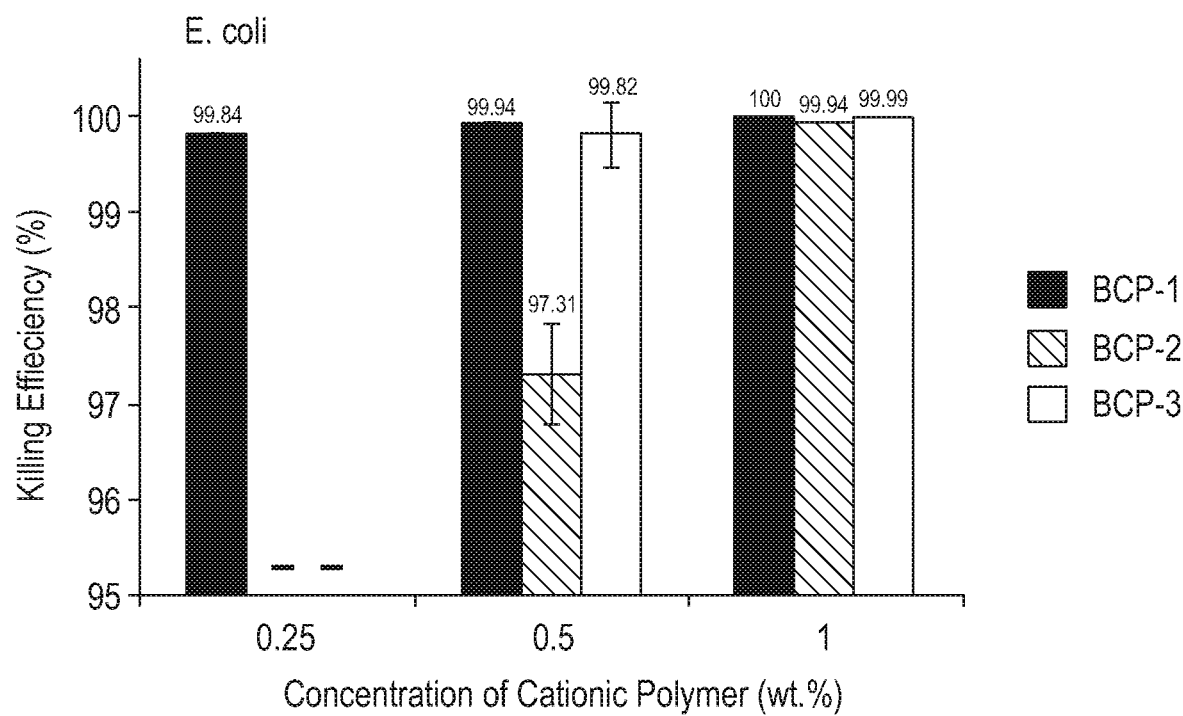
FIG. 22 is a bar graph showing the killing efficiency against E. coli of block copolymer hydrogels containing a mixture of antimicrobial block copolymer BCP-1, BCP-2, or BCP-3 and triblock copolymer TBP-1.
Figure 23:
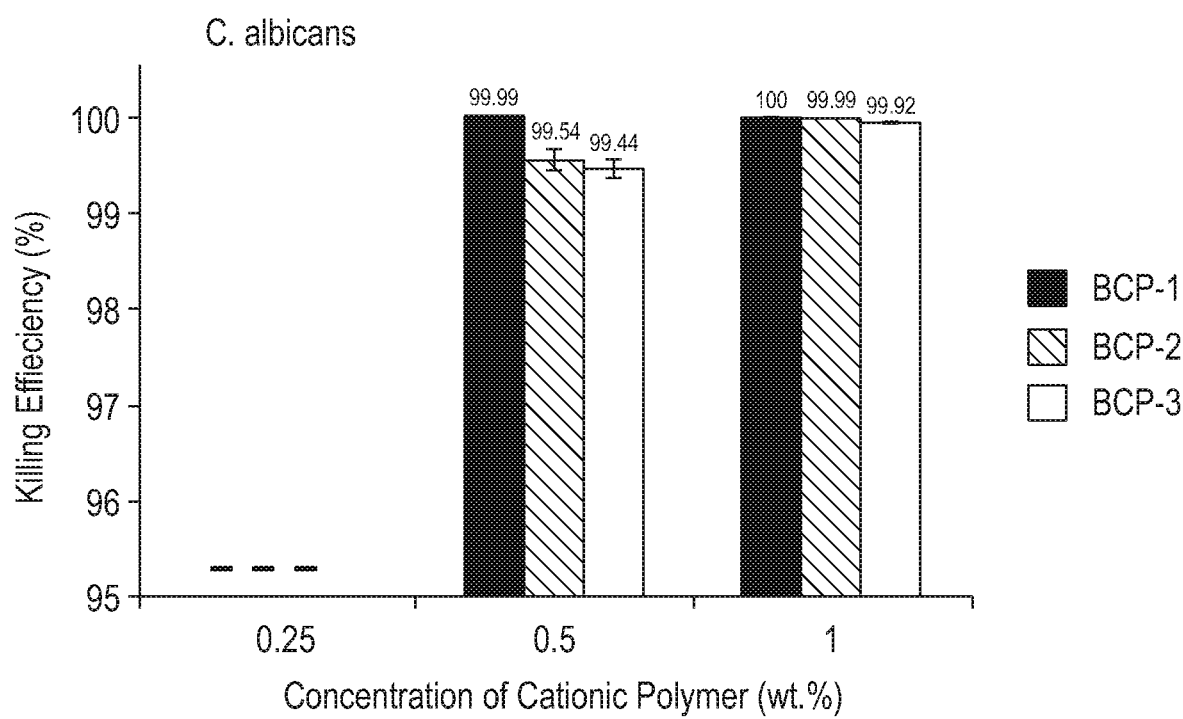
FIG. 23 is a bar graph showing the killing efficiency against C. albicans of block copolymer hydrogels containing a mixture of antimicrobial block copolymer BCP-1, BCP-2, or BCP-3 and triblock copolymer TBP-1.

FIG. 17-19 (bar graphs) show the antibacterial efficacy of different amounts of polymer-grafted silica particles APSi-PBnTU-10 (Example 37) and APSi-PBnTU-20 (Example 38) incubated at 37° C. for 18 hours with (a) *S. aureus*, (b) *E. coli* and (c) *P. aeruginosa* suspension ($3\times10^5$ CFU/mL), respectively. An aliquot of the medium serially diluted was plated onto agar plates to assess microorganism survival. The control experiment (black column) was conducted by having a cell suspension without silica particles. A patterned circle indicates that no colony was observed. The data correspond to mean±standard deviation (n=3). FIG. 17 is a bar graph showing the number of remaining viable *S. aureus* colonies after incubation with varying amounts of polymer-grafted silica particles APSi-PBnTU-10 (Example 37) and APSi-PBnTU-20 (Example 38). While APSi-PBnTU-10 could eradicate S. aureus colonies completely at 40 mg/mL, APSi-PBnTU-20 could eliminate them at a lower particle concentration of 10 mg/m, indicating a higher antimicrobial efficacy presented by the longer surface-grafted polymer chain. However, both surface-coated samples exhibited similar antibacterial efficacy against *E. coli* (FIG. 18) and *P. aeruginosa* (FIG. 19) in which they could eliminate the colonies completely at a particle concentration of 40 mg/mL. Overall, the surface-grafted polymer APSi-PBnTU-20 had greater antibacterial efficacy than APSi-PBnTU-10, possibly due to the greater number of thiouronium groups presented in the longer surface-grafted polymer chain.

Metal Ion Sequestration

The removal of undesirable heavy metal ionic impurities from industrial wastewaters or process streams is an ongoing need. Thiouronium-functionalized silica particles, which are antimicrobial and also capable of chelating metals for wastewater purification systems, are desirable.

The metal sequestration properties of APSi-PBnTU-10 and APSiPBnTU-20 were measured as follows. One milligram of thiouronium-functionalized silica particles was added into a microcentrifuge tube containing 1.4 mL aqueous solutions of $Hg(NO_3)_2$, $Pd(NO_3)_2$, $Rh(NO_3)_3$, $P^b(NO_3)_2$ and $CdSO_4$ in $NaH_2PO_4/Na_2HPO_4$ buffer (pH=6.8). The mixture was left to shake continuously at room temperature for 18 hours, and then was filtered through a 0.45 micrometer membrane filter, and the filtrates were analyzed using inductively coupled plasma mass spectrometry (ICP-MS) to determine the metal ion concentration.

Table 4 shows the concentrations of various metal ions before and after treatment with APSi-PBnTU-10 and APSiPBnTU-20 particles.

TABLE 4

| | Concentration (ppm) | | | | |
|---|---|---|---|---|---|
| | Hg(II) | Pd(II) | Rh(III) | Pb(II) | Cd(II) |
| Before Treatment | 1.26 | 0.69 | 0.96 | 0.89 | 1.07 |
| After treatment with APSi-PBnTU-10 | 0.13 | 0.016 | 0.75 | 0.87 | 1.06 |
| After treatment with APSiPBnTU-20 | 0.49 | 0.021 | 0.92 | 0.86 | 1.08 |

The surface-grafted polymer APSi-PBnTU-10 had a high selectivity for Hg(II) and Pd(II) with 90% and 98% removal, respectively. The adsorption capacity of the surface-grafted polymer APSi-PBnTU-20 was lower, removing 62% and 97% of Hg(II) and Pd(II), respectively. The high effectiveness of mercury and palladium removal from aqueous solution may be attributed to the highly accessible thiouronium groups arising from the surface-grafted polymer.

Hydrogel Preparation and Properties

To prepare the antimicrobial hydrogels, cationic polymer was first dissolved in filtered HPLC water at 25° C. in a bio-hood. The resultant solution was then added to solid triblock copolymer TBP-1 for dissolution and left to stand at room temperature.

Cationic polymer BCP-1, BCP-2, or BCP-3 was dissolved in sterile HPLC grade water (1 mL) to form a solution having a concentration of 0.1 to 1 wt. %. This solution (1 mL) was then added to TBP-1 (130 mg) and allowed to stand 4 hours at ambient temperature, to form a cationic polymer loaded hydrogel (13 wt % TBP-1 and 0.1 to 1 wt. % BCP-1, BCP-2, or BCP-3.

For antimicrobial treatment, 50 microliters of the hydrogels incorporated with various contents of cationic polymers was placed into each well of a 96-well microplate. The concentration of bacterial solution was adjusted to give an initial optical density (O.D.) reading of approximately 0.07 at 600 nm wavelength on a microplate reader (TECAN, Switzerland), which corresponds to the concentration of McFarland 1 solution ($3\times10^8$ CFU/mL). The bacterial solution was then diluted and an equal volume of bacterial suspension ($3\times10^5$) was added into each well. The 96-well plate was kept in an incubator at 37° C. under constant shaking of 300 rpm for 18 hours for *E. coli, P. aeruginosa, S. aureus* and *C. albicans*. After treatment, the samples were taken for a series of tenfold dilution, and plated onto agar plates. The plates were incubated for 24 hours at 37° C. and the number of colony-forming units (CFU) was counted. Bacteria treated in hydrogel without cationic polycarbonates were used as negative control, and each test was carried out in 3 replicates. Minimum bactericidal concentration (MBC) is defined herein as the lowest concentration of the antimicrobial composition that eliminates >99.9% of the microbes. Table 5 summarizes the MBC results.

TABLE 5

| | MBC (wt %) | | | |
|---|---|---|---|---|
| | S. aureus | E. coli | P. aeruginosa | C. albicans |
| BCP-1 | 0.5 | 0.5 | 0.5 | 0.5 |
| BCP-2 | 0.5 | 1.0 | 0.5 | 1.0 |
| BCP-3 | 1.0 | 0.5 | 1.0 | 1.0 |

The hydrogels were challenged with an inoculum of $3\times10^5$ CFU/mL and proliferation capacity of the survived cells was then assessed 24 hours later via the spread plate technique. The results show that the cationic polymers are broadly antimicrobial towards bacteria and fungi. The bar graphs of FIG. 20-23 show the killing efficiency of the loaded hydrogels against *S. aureus*, *P. aeruginosa*, *E. coli*, and *C. albicans*, respectively, where a "–" in the figure indicates no observable effect. Hydrogels formed with BCP-1 and BCP-2 were highly effective against *S. aureus* and *P. aeruginosa* at 0.5 wt % concentration, and highly effective against *E. coli* and *C. albicans* at 1.0 wt % concentration.

Guanidinium- and Thiouronium-Functionalized Polyurethanes

Example 41

Preparation of Boc-protected guanidine 1,3-propanediol, DBHG.

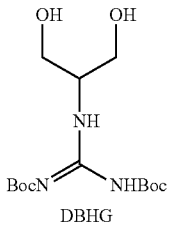

DBHG was prepared by the procedure of Example 1 using 2-amino-1,3-propanediol. Yield: 70%; $^1$H-NMR (400 MHz, CDCl$_3$, 22° C.): δ 11.42 (s, 1H, NH), 8.86 (d, J=6.6 Hz, 1H, NH), 4.05 (dt, J=6.5, 4.8 Hz, 1H, —CH—), 3.79-3.70 (m, 4H, —CH$_2$—), 1.45 (d, J=8.9 Hz, 18H, Boc —CH$_3$).

Example 42

Preparation of guanidinium-functionalized polyurethane, GuaPU-1 (x is the degree of polymerization DP >1).

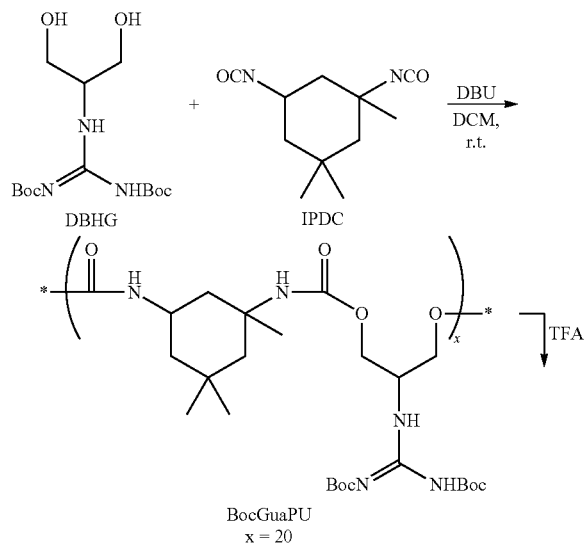

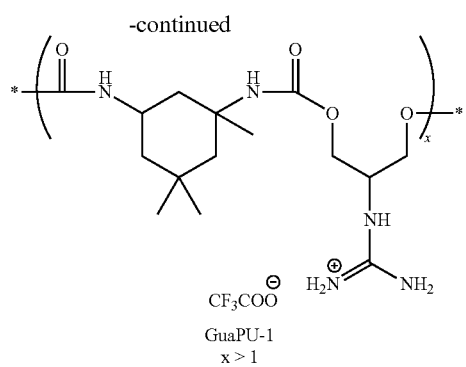

The precursor polyurethane, BocGuaPU, was synthesized by dissolving the Boc-protected guanidine 1,3-propanediol (DBHG, 333 mg, 1.0 mmol, 1.0 equivalents) and isophorone diisocyanate (IPDC, 233 microliters, 1.1 mmol, 1.1 equivalents) in 1 mL of anhydrous dichloromethane. Polymerization was subsequently initiated by adding DBU (7.4 microliters, 0.05 mmol) and the solution was allowed to stir at room temperature for 0.5 hours. Upon completion of the polymerization as verified by gel-permeation chromatography, the reaction was quenched by addition of benzoic acid and further purified via preparative size exclusion chromatography to yield BocGuaPU as a crystalline, transparent solid. Yield: 82%. $^1$-H NMR (400 MHz, CDCl$_3$, 22° C.): δ 11.52 (bs, —NH), 8.59 (bs, —NH), 4.71 (m, —CH), 4.19 (bs, —CH$_2$), 3.00-2.85 (bs, —CH), 1.73-0.84 (m, OCONHCH$_2$CH$_2$, OCONHCHCH$_2$, Boc —CH$_3$ and —CH$_3$).

The resultant guanidinium-functionalized polyurethane, GuaPU-1, was synthesized by dissolving BocGuaPU in 4 mL of dichloromethane and subsequently adding trifluoroacetic acid (TFA, 1 mL, 20% v/v). The solution was allowed to stir at room temperature for 18 hours. Upon completion of the reaction, the solvent was removed by purging with a stream of nitrogen gas for 0.5 hours. The polymer was then purified by re-dissolving the crude polymer in methanol and precipitated in cold diethyl ether with multiple washes to yield Gua-PU-1 as a waxy white solid. Yield: 78%. $^1$H NMR (400 MHz, DMSO, 22° C.): δ 7.93-6.81 (m, —NH and —CONH), 4.04 (m, —CH and —CH$_2$), 2.76 (bs, —CH), 1.70-0.69 (m, OCONHCH2CH$_2$, OCONHCHCH$_2$ and —CH$_3$).

Example 43

Preparation of Guanidinium-Functionalized Polyurethane, GuaPU-2.

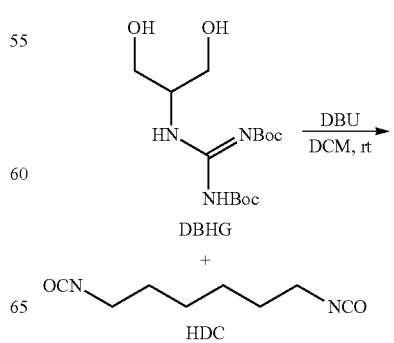

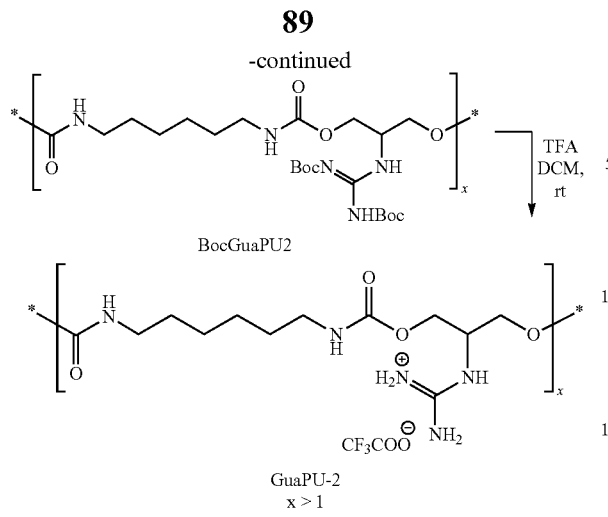

BocGuaPU2

GuaPU-2
x > 1

The precursor polyurethane, BocGuaPU2, was synthesized by dissolving the Boc-protected guanidine 1,3-propanediol (DBHG, 333 mg, 1.0 mmol, 1.0 equivalents), and hexane diisocyanate (HDC, 177 microliters, 1.1 mmol, 1.1 equivalents) in anhydrous dichloromethane (DCM, 1 mL). Polymerization was subsequently initiated by adding DBU (7.4 microliters, 0.05 mmol) and the solution was allowed to stir at room temperature for 0.5 hours. Upon completion of the polymerization as verified by gel-permeation chromatography, the reaction was quenched by addition of benzoic acid and further purified via precipitation in cold ether to yield BocGuaPU2 as a crystalline, transparent solid. Yield: 86%. $^1$H NMR (400 MHz, CDCl$_3$, 22° C.): δ 11.52 (s, —NH), 8.59 (m, —NH), 4.97 (bs, —CH), 4.18 (bs, —CH$_2$), 3.17 (m, —CH$_2$), 1.51 (bs, —CH$_2$ and Boc —CH$_3$), 1.35 (bs, —CH$_2$).

The resultant guanidinium-functionalized polyurethane, GuaPU-2, was synthesized by dissolving BocGuaPU2 in 4 mL of dichloromethane and subsequently added with trifluoroacetic acid (1 mL, 20% v/v). The solution was allowed to stir at room temperature for 18 hours. Upon completion of the reaction, the solvent was removed by purging with a stream of nitrogen gas for 0.5 hours. The polymer was then purified by re-dissolving the crude polymer in methanol and precipitated in cold diethyl ether with multiple washes to yield Gua-PU-2 as a waxy white solid. Yield: 75% $^1$H NMR (400 MHz, DMSO, 22° C.): δ 8.00-6.92 (m, —NH— and —CONH—), 4.26-3.71 (m, —CH and —CH$_2$—), 2.96 (d, —CH$_2$—), 1.30 (d, Example 44

Preparation of guanidinium-functionalized PEG-polyurethane, GuaPEG-PU1.

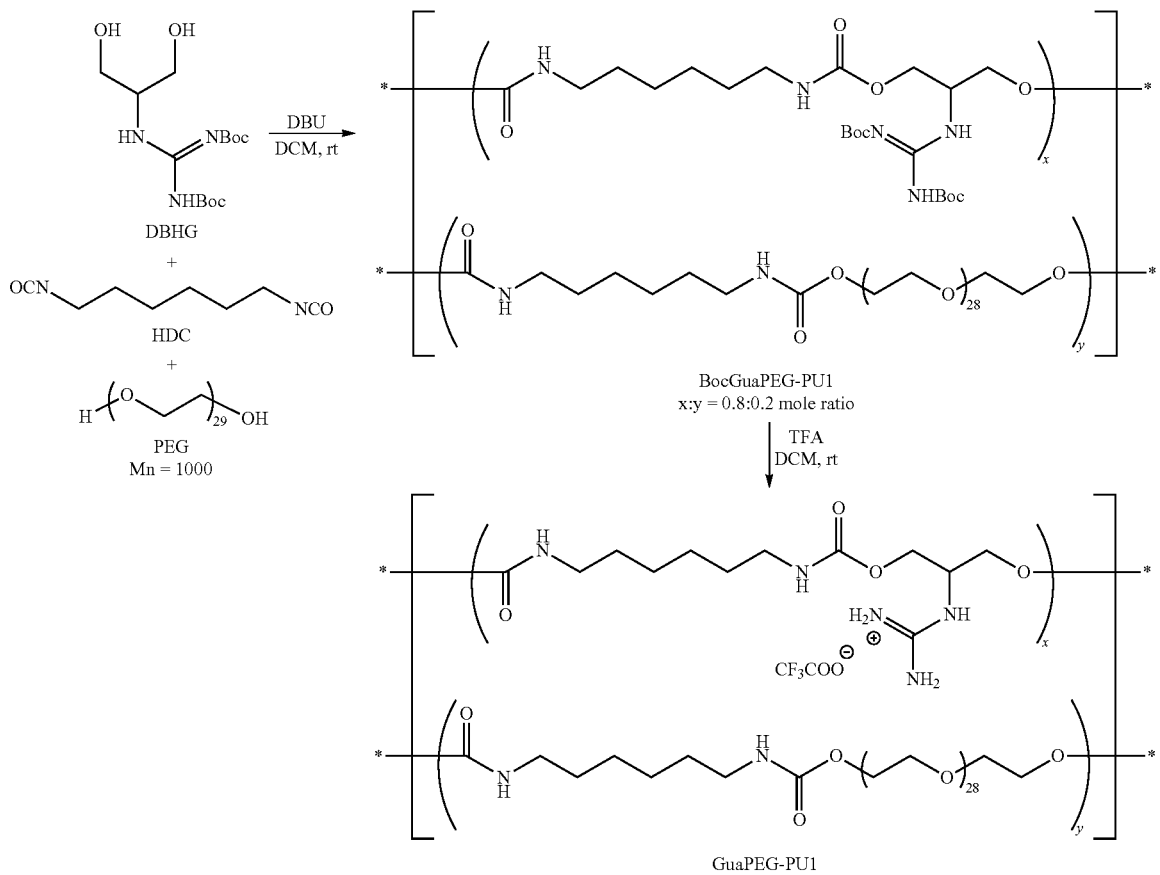

BocGuaPEG-PU1
x:y = 0.8:0.2 mole ratio

GuaPEG-PU1

In the above notation, vertical stacking of the parenthesized repeat units within the square brackets indicates a random distribution of the repeat units in the polymer chain.

The ratio x:y represents molar ratio of the repeat units. Polymer chain end groups are not specified.

The precursor polyurethane, BocGuaPEG-PU1, was synthesized by dissolving the Boc-protected guanidine 1,3-propanediol (DBHG, 266 mg, 0.8 mmol, 0.8 equivalents), polyethylene glycol (PEG, 200 mg, 0.2 mmol, 0.2 equivalents, Mn=1000) and hexane diisocyanate (HDC, 177 microliters, 1.1 mmol, 1.1 equivalents) in anhydrous dichloromethane (DCM,1 mL). Polymerization was subsequently initiated by adding DBU (7.4 microliters, 0.05 mmol) and the solution was allowed to stir at room temperature for 0.5 hours. Upon completion of the polymerization as verified by gel-permeation chromatography, the reaction was quenched by addition of benzoic acid and further purified via precipitation in cold ether to yield BocGuaPEG-PU1 as a crystalline, transparent solid. Yield: 80%. $^1$H NMR (400 MHz, DMSO, 22° C.): δ 11.52 (m, NH), 8.32 (m, NH), 7.31-7.19 (m, —CONH—), 4.43 (m, —CH—), 4.06 (m, —CH$_2$—), 3.51 (bs, PEG —CH$_2$—), 2.94 (m, —CH$_2$—), 1.36 (m, —CH$_2$—and Boc —CH$_3$).

The resultant guanidinium-functionalized polyurethane, GuaPEG-PU1, was synthesized by dissolving BocGuaPEG-PU1 in dichloromethane (4 mL) and subsequently adding trifluoroacetic acid (1 mL, 20% v/v). The solution was allowed to stir at room temperature for 18 hours. Upon completion of the reaction, the solvent was removed by purging with a stream of nitrogen gas for 0.5 hours. The polymer was then purified by re-dissolving the crude polymer in methanol and precipitated in cold diethyl ether with multiple washes to yield GuaPEG-PU1 as a waxy white solid. Yield: 72% $^1$H NMR (400 MHz, DMSO, 22° C.): δ 7.91-6.88 (m, NH and —CONH—), 4.18-3.88 (m, —CH— and —CH$_2$—), 3.57-3.40 (bs, PEG —CH$_2$—), 3.04-2.90 (bs, —CH$_2$—), 1.46-1.16 (m, —CH$_2$—).

Table 6 summarizes the antimicrobial activity (MIC) of the guanidinium-functionalized polyurethane.

TABLE 6

| Example | Polymer Name | MIC (mg/L) | | | |
|---|---|---|---|---|---|
| | | S. aureus | E. coli | P. aeruginosa | C. albicans |
| 43 | GuaPU-2 | 125 | 125 | 250 | 125 |
| 44 | GuaPEG-PU1 | 31.3 | 31.3 | 31.3 | 125 |

The Table 6 results demonstrate broad-spectrum high activity against Gram-positive and Gram-negative bacteria. The guanidinium-functionalized polyurethane with PEG (GuaPEG-PU1) showed better MIC values than the polymer without PEG (GuaPU-2). In particular, GuaPEG-PU1 showed a MIC value of 31.3 mg/L against S. aureus, E. coli and P. aeruginosa. Moreover, a higher MIC value of 125 mg/L was needed to be effective against C. albicans.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. An antimicrobial cationic polymer, comprising a cationic subunit of formula (A-1):

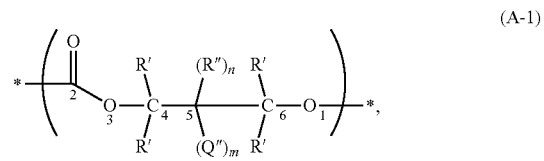

wherein atoms 1-6 are backbone atoms of the cationic polymer, m is 1 or 2, n is 0 or 1, wherein when m is 2, n is 0, each R' is an independent monovalent radical selected from the group consisting of hydrogen and alkyl groups comprising 1 to 6 carbons, R" is a monovalent radical selected from the group consisting of hydrogen and alkyl groups comprising 1 to 6 carbons, and each Q" is an independent group comprising an isothiouronium group.

2. The cationic polymer of claim 1, wherein the cationic polymer is selected from the group consisting of polycarbonates and polyurethanes.

3. The cationic polymer of claim 1, wherein the cationic polymer is capable of killing a Gram-positive bacterium, a Gram-negative bacterium, and/or a fungus.

4. The cationic polymer of claim 1, wherein m is 1 and n is 1.

5. The cationic polymer of claim 1, wherein the cationic subunit has a structure according to formula (A-2):

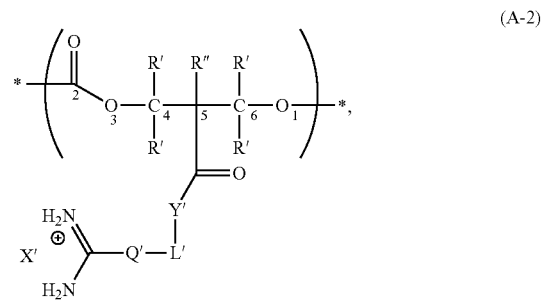

wherein
- atoms 1-6 are backbone atoms of the cationic polymer,
- L' is a divalent hydrocarbon radical comprising 2 to 30 carbons,
- Q' is *—S—*,
- each R' is an independent monovalent radical selected from the group consisting of hydrogen and alkyl groups comprising 1 to 6 carbons,
- R" is a monovalent radical selected from the group consisting of hydrogen and alkyl groups comprising 1 to 6 carbons,
- X' is a negative-charged counterion, and
- Y' is *—O—* or *—N(H)—*.

6. The cationic polymer of claim 5, wherein L' is selected from the group consisting of 1,2-ethylene, 1,3-propylene, 1,4-butylene, 1,5-pentylene, 1,4-cyclohexylene, and 1,4-phenylene.

7. The cationic polymer of claim 5, wherein Y' is *—O—*.

8. The cationic polymer of claim 5, wherein Y' is *—N(H)—*.

9. The cationic polymer of claim 5, wherein R" is methyl or ethyl.

10. The cationic polymer of claim 5, wherein X' is a negative-charged counterion selected from the group consisting of chloride, bromide, iodide, acetate, benzoate, trifluoroacetate, hydrogen carbonate, methansulfonate, hydrogen sulfate, and dihydrogen phosphate.

11. The cationic polymer of claim 1, wherein the cationic polymer has a structure in accordance with formula (B-1):

$$Z'\text{—}P'\text{—}Z'' \tag{B-1}$$

wherein
- Z' is a monovalent first end group comprising 1 to 40 carbons,
- Z" is a monovalent second end group selected from the group consisting of hydrogen and groups comprising 1 to 40 carbons, and
- P' is a polymer chain comprising the cationic subunit of formula (A-1).

12. The cationic polymer of claim 11, wherein P' is a polycarbonate.

13. The cationic polymer of claim 11, wherein P' is a polyurethane.

14. The cationic polymer of claim 1, wherein the cationic polymer has a structure in accordance with formula (B-2):

$$Z^b\text{—}P^b\text{—}C'\text{—}P^b\text{—}Z^b \tag{B-2}$$

wherein
- each $P^b$ is an independent polymer chain comprising the cationic subunit,
- C' is a divalent linking group (core group) comprising 2 to 25 carbons, wherein C' comprises two heteroatoms independently selected from the group consisting of nitrogen, oxygen, and sulfur, wherein the heteroatoms are covalently linked to respective polymer chains $P^b$, and
- each $Z^b$ is an independent monovalent end group selected from the group consisting of hydrogen and groups comprising 1 to 40 carbons.

15. A method of killing a microbe, comprising contacting the microbe with the cationic polymer of claim 1.

16. An antimicrobial composition comprising the cationic polymer of claim 1 and at least one other chemical component bound by non-covalent interactions.

17. The antimicrobial composition of claim 16, wherein the antimicrobial composition is an aqueous mixture.

18. The antimicrobial composition of claim 16, wherein said at least one other component is a drug.

19. The antimicrobial composition of claim 16, wherein said at least one other chemical component is a gene.

20. The antimicrobial composition of claim 16, wherein said at least one other component is an amphiphilic block copolymer and the antimicrobial composition is a hydrogel in water.

21. The antimicrobial composition of claim 16, wherein the antimicrobial composition is a nanoparticle in water.

22. The antimicrobial composition of claim 21, wherein the nanoparticle has an average circular cross sectional diameter between 10 nm and 500 nm.

23. The antimicrobial composition of claim 16, wherein the antimicrobial composition is selected from the group consisting of soaps, shampoos, skin lotions, skin creams, cosmetics, mouthwashes, wound care agents, deodorants, surface cleaning agents, and laundry detergents.

* * * * *